US008532936B2

(12) United States Patent
Rava

(10) Patent No.: US 8,532,936 B2
(45) Date of Patent: *Sep. 10, 2013

(54) NORMALIZING CHROMOSOMES FOR THE DETERMINATION AND VERIFICATION OF COMMON AND RARE CHROMOSOMAL ANEUPLOIDIES

(75) Inventor: Richard P. Rava, Redwood City, CA (US)

(73) Assignee: Verinata Health, Inc., Redwood City, CA (US)

( * ) Notice: Subject to any disclaimer, the term of this patent is extended or adjusted under 35 U.S.C. 154(b) by 15 days.

This patent is subject to a terminal disclaimer.

(21) Appl. No.: 13/087,842

(22) Filed: Apr. 15, 2011

(65) Prior Publication Data

US 2012/0264115 A1 Oct. 18, 2012

(30) Foreign Application Priority Data

Apr. 14, 2011 (GB) .................... 1106394.8

(51) Int. Cl.
*G06F 19/00* (2011.01)
*C12Q 1/68* (2006.01)

(52) U.S. Cl.
USPC .............................................. 702/20; 435/6.1

(58) Field of Classification Search
None
See application file for complete search history.

(56) References Cited

U.S. PATENT DOCUMENTS

| | | | |
|---|---|---|---|
| 5,994,057 | A | 11/1999 | Mansfield |
| 6,440,706 | B1 | 8/2002 | Vogelstein et al. |
| 7,252,946 | B2 | 8/2007 | Szasz |
| 7,332,277 | B2 | 2/2008 | Dhallan |
| 7,645,576 | B2 | 1/2010 | Lo et al. |
| 7,888,017 | B2 | 2/2011 | Quake et al. |
| 2002/0142324 | A1 | 10/2002 | Wang et al. |
| 2003/0194704 | A1 | 10/2003 | Penn et al. |
| 2005/0221341 | A1 | 10/2005 | Shimkets et al. |
| 2006/0046258 | A1 | 3/2006 | Lapidus et al. |
| 2006/0257895 | A1 | 11/2006 | Pinkel et al. |
| 2006/0286558 | A1 | 12/2006 | Novoradovskaya et al. |
| 2007/0134658 | A1 | 6/2007 | Bohmer et al. |
| 2007/0207466 | A1 | 9/2007 | Cantor et al. |
| 2008/0020390 | A1 | 1/2008 | Mitchell et al. |
| 2008/0050739 | A1 | 2/2008 | Stoughton et al. |
| 2008/0064098 | A1 | 3/2008 | Allickson |
| 2008/0070792 | A1 | 3/2008 | Stoughton et al. |
| 2008/0138809 | A1 | 6/2008 | Kapur et al. |
| 2008/0220422 | A1 | 9/2008 | Shoemaker et al. |
| 2008/0299562 | A1 | 12/2008 | Oeth et al. |
| 2009/0029377 | A1 | 1/2009 | Lo et al. |
| 2009/0087847 | A1 | 4/2009 | Lo et al. |
| 2009/0270601 | A1 | 10/2009 | Benner et al. |
| 2009/0299645 | A1 | 12/2009 | Colby et al. |
| 2009/0317817 | A1 | 12/2009 | Oeth et al. |
| 2009/0317818 | A1 | 12/2009 | Ehrich et al. |
| 2010/0068711 | A1 | 3/2010 | Umansky et al. |
| 2010/0112575 | A1 | 5/2010 | Fan et al. |
| 2010/0112590 | A1 | 5/2010 | Lo et al. |
| 2010/0138165 | A1 | 6/2010 | Fan et al. |
| 2010/0167954 | A1 | 7/2010 | Earnshaw et al. |
| 2010/0184075 | A1 | 7/2010 | Cantor et al. |
| 2010/0216151 | A1 | 8/2010 | Lapidus et al. |
| 2010/0216153 | A1 | 8/2010 | Lapidus et al. |
| 2011/0105353 | A1 | 5/2011 | Lo et al. |
| 2011/0245085 | A1 | 10/2011 | Rava et al. |
| 2012/0034603 | A1 | 2/2012 | Oliphant et al. |
| 2012/0034685 | A1 | 2/2012 | Sparks et al. |
| 2012/0040859 | A1 | 2/2012 | Sparks et al. |

FOREIGN PATENT DOCUMENTS

| | | |
|---|---|---|
| EP | 2334812 A2 | 6/2011 |
| GB | 2479476 A | 10/2011 |
| GB | 2479080 B | 1/2012 |
| GB | 2479471 B | 2/2012 |
| GB | 2484764 B | 9/2012 |
| WO | WO 98/44151 A1 | 10/1998 |
| WO | WO 00/18957 A1 | 4/2000 |
| WO | WO 2007/100911 A2 | 9/2007 |
| WO | WO 2011/051283 A1 | 5/2011 |
| WO | WO 2012/019187 | 8/2011 |
| WO | WO 2012/019193 | 8/2011 |
| WO | WO 2012/019198 | 8/2011 |
| WO | WO 2012/019200 | 8/2011 |
| WO | WO 2012/141712 | 10/2012 |

OTHER PUBLICATIONS

U.S. Appl. No. 13/009,718, filed Jan. 19, 2010, Rava.
U.S. Appl. No. 13/012,222, filed Jan. 24, 2010, Chuu et al.
U.S. Appl. No. 61/371,605, filed Aug. 6, 2010, Oliphant et al.
U.S. Appl. No. 12/958,347, filed Dec. 1, 2010, Rava et al.
U.S. Appl. No. 12/958,353, filed Dec. 1, 2010, Rava et al.
U.S. Appl. No. 12/958,356, filed Dec. 1, 2010, Quake et al.
U.S. Appl. No. 13/191,366, filed Jul. 26, 2011, Rava et al.
U.S. Appl. No. 13/333,832, filed Dec. 21, 2011, Rava et al.
U.S. Appl. No. 13/365,134, filed Feb. 2, 2012, Rava et al.

(Continued)

*Primary Examiner* — John S Brusca

(74) *Attorney, Agent, or Firm* — Elena E. Quertermous

(57) ABSTRACT

The present invention provides a method capable of detecting single or multiple fetal chromosomal aneuploidies in a maternal sample comprising fetal and maternal nucleic acids, and verifying that the correct determination has been made. The method is applicable to determining copy number variations (CNV) of any sequence of interest in samples comprising mixtures of genomic nucleic acids derived from two different genomes, and which are known or are suspected to differ in the amount of one or more sequence of interest. The method is applicable at least to the practice of noninvasive prenatal diagnostics, and to the diagnosis and monitoring of conditions associated with a difference in sequence representation in healthy versus diseased individuals.

35 Claims, 9 Drawing Sheets

(56) References Cited

OTHER PUBLICATIONS

U.S. Appl. No. 13/364,809, filed Feb. 2, 2012, Rava et al.
U.S. Appl. No. 13/365,240, filed Feb. 2, 2012, Quake et al.
U.S. Appl. No. 13/400,028, filed Feb. 17, 2012, Rava et al.
Bentley et al., Accurate whole genome sequencing using reversible terminator chemistry. Nature Nov. 6, 2008; 456(7218)53-9.
Botezatu et al., Genetic analysis of DNA excreted in urine: a new approach for detecting specific genomic DNA sequences from cells dying in an organism. Clin Chem. Aug. 2000; 46(8 Pt 1):1078-84.
Butler et al., Short tandem repeat typing technologies used in human identity testing. Biotechniques. Oct. 2007; 43(4):ii-v.
Butler et al., The development of reduced size STR amplicons as tools for analysis of degraded DNA. J Forensic Sci. Sep. 2003; 48(5):1054-64.
Chan et al., Size distributions of maternal and fetal DNA in maternal plasma Clin Chem. Jan. 2004; 50(1):88-92.
Chen et al., Microsatellite alterations in plasma DNA of small cell lung cancer patients. Nat. Med. Sep. 1996; 2(9):1033-5.
Chiu et al., Maternal plasma DNA analysis with massively parallel sequencing by ligation for noninvasive prenatal diagnosis of trisomy 21. Clin Chem. Mar. 2010; 56(3):459-63.
Chiu et al., Non-invasive prenatal assessment of trisomy 21 by multiplexed maternal plasma DNA sequencing: large scale validity study. BMJ. Jan. 11, 2011; 342:c7401.
Chiu et al., Non-invasive prenatal diagnosis by single molecule counting technologies. Trends Genet. Jul. 2009; 25(7):324-31.
Chiu et al., Noninvasive prenatal diagnosis of fetal chromosomal aneuploidy by massively parallel genomic sequencing of DNA in maternal plasma. Proc Natl Acad Sci USA. Dec. 23, 2008; 105(51):20458-63.
Chu et al., Statistical model for whole genome sequencing and its application to minimally invasive diagnosis of fetal genetic disease. Bioinformatics. May 15, 2009; 25(10):1244-50.
Coble et al., Characterization of new miniSTR loci to aid analysis of degraded DNA, J Forensic Sci. Jan. 2005; 50(1):43-53.
Dhallan et al., A non-invasive test for prenatal diagnosis based on fetal DNA present in maternal blood: a preliminary study. Lancet. Feb. 10, 2007; 369(9560):474-81.
Dixon et al., Analysis of artificially degraded DNA using STRs and SNPs—results of a collaborative European (EDNAP) exercise. Forensic Sci Int. Dec. 1, 2006; 164(1):33-44.
Ehrich et al., Noninvasive detection of fetal trisomy 21 by sequencing of DNA in maternal blood: a study in a clinical setting. Am J Obstet Gynecol. Mar. 2011; 204(3):20.e1-11.
European Search Report dated Feb. 22, 2012 in EP Patent Application 10825822.9.
European Search Report dated Feb. 22, 2012 in EP Patent Application 10830939.4.
European Search Report dated Feb. 22, 2012 in EP Patent Application 10830938.6.
Examination Report dated Jun. 24, 2011 in U.K. Patent Application No. 1106394.8.
Examination Report dated Jul. 15, 2011 in U.K. Patent Application No. 1107268.3.
Examination Report dated Jul. 15, 2011 in U.K. Patent Application No. 1108795.4.
Examination Report dated Jul. 15, 2011 in U.K. Patent Application No. 1108794.7.
Examination Report dated Nov. 15, 2011 in U.K. Patent Application No. 1107268.3.
Examination Report dated Dec. 7, 2011 in U.K. Patent Application No. 1114713.9.
Examination Report dated Dec. 16, 2011 in U.K. Patent Application No. 1108795.4.
Fan et al., Analysis of the size distributions of fetal and maternal cell-free DNA by paired-end sequencing. Clin Chem. Aug. 2010; 56(8):1279-86.
Fan et al., Detection of aneuploidy with digital polymerase chain reaction. Anal Chem. Oct. 1, 2007; 79(19):7576-9.
Fan et al., In principle method for noninvasive determination of the fetal genome. Nature Precedings 10.1038/npre.2010.5373.1. 2010.
Fan et al., Microfluidic digital PCR enables rapid prenatal diagnosis of fetal aneuploidy. Am J Obstet Gynecol, May 2009; 200(5):543.e1-7.
Fan et al., Noninvasive diagnosis of fetal aneuploidy by shotgun sequencing DNA from maternal blood. Proc Natl Acad Sci USA. Oct. 21, 2008; 105(42):16266-71.
Fan et al., Senstitvity of noninvasive prenatal detection of fetal aneuploidy from maternal plasma using shotgun sequencing in limited only by counting statistics. PLoS One. May 3, 2010; 5(5):e10439.
Fan et al., Whole Genome Molecular Haplotyping of Single Cells. Nat Biotechnol. Jan. 2011; 29(1):51-7.
Ghanta et al., Non-invasive prenatal detection of trisomy 21 using tandem single nucleotide polymorphisms. PLoS One. Oct. 8, 2010;5(10):e13184.
Grubwieser et al., A new "miniSTR-multiplex" displaying reduced amplicon lengths for the analysis of degraded DNA. Int J Legal Med. Mar. 2006; 120(2):115-20.
Hanson et al., Whole genome amplification strategy for forensic genetic analysis using single or few cell equivalents of genomic DNA. Anal Biochem. Nov. 15, 2005; 346(2):246-57.
Harris et al., Single-molecule DNA sequencing of a viral genome. Science. Apr. 4, 2008; 320(5872):106-9.
Harrison et al., Polymer-stimulated ligation: enhanced ligation of oglio- and-polynucleotides by T4 RNA ligase in polymer solutions. Nucleic Acids Res. Nov. 12, 1984; 12(21):8235-51.
Hayashi et al., Regulation of inter- and intramolecular ligation with T4 DNA ligase in the presence of polyethylene glycol. Nucleic Acids Res. Oct. 10, 1986; 14(19):7617-31.
Hill et al., "Characterization of 26 new miniSTR loci" Poster π44-17$^{th}$ International Symposium on Human Identification, Nashville, TN Oct. 10-12, 2006.
Huang et al., Isolation of cell-free DNA from maternal plasma using manual and automated systems. Methods Mol Biol. 2008; 444:203-8.
Hung et al., Detection of cirulating fetal nucleic acids: a review of methods and applications. J Clin Pathol. Apr. 2009; 62(4):308-13.
Illumina, Preparing samples for CHIP sequencing of DNA. E-pub at grcf.jhmi.edu/hts/protocols/11257047_ChIP_Sample_Prep.pdf. 2007.
International Search Report and Written Opinion dated Feb. 8, 2011 for PCT Application No. PCT/US2010/058606.
International Search Report and Written Opinion dated Mar. 1, 2011 for PCT Application No. PCT/US2010/058614.
International Search Report and Written Opinion dated Apr. 4, 2011 for PCT Application No. PCT/US2010/058609.
International Search Report and Written Opinion dated Apr. 11, 2011 for PCT Application No. PCT/US2011/021729.
International Search Report and Written Opinion dated May 19, 2011 for PCT Application No. PCT/US2010/058612.
International, The International HapMap Project, Nature. 2003;426:789-96.
Jama et al., Quantification of Cell-Free Fetal DNA Levels in Maternal Plasma by STR Analysis. ACMG Annual Clincial Genetics Meeting Poster 398; Mar. 24-28, 2010. Available online at http://acmg.omnibooksonline.com/2010/data/papers/398.pdf and http://acmg.omnibooksonline.com/2010/index/html.
Jorgez et al., Improving enrichment of circulating fetal DNA for genetic testing: size fractionation followed by whole genome amplification. Fetal Diagn Ther. 2009; 25(3):314-9.
Ju, et al., Four-color DNA sequencing by synthesis using cleavable fluorescent nucleotide reversible terminators. Proc Natl Acad Sci USA, 2006; 103(52):19635-19640.
Kidd et al., Developing a SNP panel for forensic identification of individuals. Forensic Sci Int. Dec. 1, 2006; 164(1):20-32.
Koide et al., Fragmentation of cell-free fetal DNA in plasma and urine of pregnant women. Prenat. Diagn. Jul. 2005; 25(7):604-7.
Kozarewa et al., Amplification-free Illumina sequencing-library preparation facilitates improved mapping and assembly of GC-biased genomes. Nat Methods. Apr. 2009; 6(4):291-5.

Lazinski & Camilli, Modified protocol for Illumina paired-end library construction. Available online at http://genomics.med.tufts.edu/documents/htseq_protocol_for_illumina_paired.pdf Accessed Jun. 21, 2011.

Leon et al., Free DNA in the serum of cancer patients and the effect of therapy. Cancer Res. Mar. 1977: 37(3):646-50.

Levy et al., The Diploid Genome Sequence of an Individual Human. PLoS Biol. Sep. 4, 2007; 5(10):e254.

Li et al., Size separation of circulatory DNA in maternal plasma permits ready detection of fetal DNA polymorphisms. Clin Chem. Jun. 2004; 50(6):1002-11.

Liao et al., Targeted massively parallel sequencing of maternal plasma DNA permits efficient and unbiased detection of fetal alleles. Clin Chem. Jan. 2011; 57(1):92-101.

Liu et al., Feasibility study of using fetal DNA in maternal plasma for non-invasive prenatal diagnosis. Acta Obstet Gynecol Scand. 2007; 86(5):535-41.

Lo et al., Digital PCR for the molecular detection of fetal chromosomal aneuploidy. Proc Natl Acad Sci USA. Aug. 7, 2007; 104(32):13116-21.

Lo et al., Increased fetal DNA concentrations in the plasma of pregnant women carrying fetuses with trisomy 21. Clin Chem. Oct. 1999; 45(10):1747-51.

Lo et al., Maternal plasma DNA sequencing reveals the genome-wide genetic and mutational profile of the fetus. Sci Transl Med. Dec. 8, 2010; 2(61):61ra91.

Lo et al., Presence of fetal DNA in maternal plasma. Lancet. Aug. 16, 1997; 350(9076):485-7.

Lo et al., Quantitative analysis of fetal DNA in maternal plasma and serum: implications for noninvasive prenatal diagnosis. Am J Hum Genet. Apr. 1998; 62(4):768-75.

Lo et al., Rapid clearance of fetal DNA from maternal plasma. Am J Hum Genet. 1999. 64(1):218-24.

Lo, Y. M., Noninvasive prenatal detection of fetal chromosomal aneuploidies by maternal plasma nucleic acid analysis: a review of the current state of the art. BJOG, 2009, vol. 116, 152-157.

Lo, Y.M., Noninvasive prenatal detection of fetal chromosomal aneuploidies by maternal plasma nucleic acid analysis. Clin Chem. Jan. 2008; 54(3):461-466.

Lun et al., Microfluidics Digital PCR Reveals a Higher than Expected Fraction of Fetal DNA in Maternal Plasma. Clinical Chemistry, 2008, vol. 54, No. 10, 1664-1672.

McKernan et al., Sequence and structural variation in a human genome uncovered by short-read, massively parallel ligation sequencing using two-base encoding. Genome Res. Sep. 2009; 19(9):1527-41.

Metzker, Sequencing technologies—the next generation. Nat Rev Genet. Jan. 2010; 11(1):31-46.

Nakamoto et al., Detection of microsatellite alterations in plasma DNA of malignant mucosal melanoma using whole genome amplification. Bull Tokyo Dent Coll. May 2008; 49(2):77-87.

Nicklas et al., A real-time multiplex SNP melting assay to discriminate individuals. J. Forensic Sci. Nov. 2008; 53(6):1316-24.

Pakstis et al., Candidate SNPs for a universal individual identification panel. Hum Genet. May 2007; 121(3-4):305-17.

Pakstis et al., SNPs for a universal individual identification panel. Hum Genet. Mar. 2010; 127(3):315-24.

Pathak et al., Circulating cell-free DNA in plasma/serum of lung cancer patients as a potential screening and prognostic tool. Clin Chem. Oct. 2006; 52(10):1833-42.

Pertl et al., Detection of male and female DNA in maternal plasma by multiplex florescent polymerase chain reaction amplification of short tandem repeats. Hum Genet. Jan. 2000; 106(1):45-9.

Pheiffer et al., Polymer-stimulated ligation: enhanced blunt- or cohesive-end ligation of DNA or deoxyribooligoncleotides by T4 DNA ligase in polymer solutions. Nucleic Acids Res. Nov. 25, 1983; 11(22):7853-71.

Pushkarev et al., Single-molecule sequencing of an individual human genome. Nat Biotechnol. Sep. 2009; 27(9):847-50.

Quail et al., A large genome center's improvements to the illumina sequencing system. Nat Methods, Dec. 2008; 5(12):1005-10.

Schwartzenbach et al., Cell-free tumor DNA in blood plasma as a marker for circulating tumor cells in prostate cancer. Clin Cancer Res. Feb. 1, 2009; 15(3):1032-8.

Schwartzenbach et al., Comparative evaluation of cell-free tumor DNA in blood and disseminated tumor cells in bone marrow of patients with primary breast cancer. Breast Cancer Res. 2009; 11(5):R71.

Sehnert, et al., Optimal Detection of Fetal Chromosomal Abnormalities by Massively Parallel DNA Sequencing of Cell-Free Fetal DNA from Maternal Blood. Clinical Chemistry, Jul. 2011, vol. 57 No. 7:1042-1049. E-pub on Apr. 25, 2011 as doi:10.1373/clinchem.2011.165910.

Su et al., Human urine contains small, 153-250 nucleotide-sized, soluble DNA derived from the circulation and may be useful in the detection of colorectal cancer. J Mol Diagn. May 2004; 6(2):101-7.

Tong et al., Noninvasive prenatal detection of trisomy 21 by an epigenetic-genetic chromosome-dosage approach. Clin Chem. Jan. 2010; 56(1):90-8.

Vallone et al., Demonstration of rapid multiplex OCR amplification involving 16 genetic loci. Forensic Sci Int Genet. Dec. 2008; 3(1):42-5.

Voelkerding et al., Digital Fetal Aneuploidy Diagnosis by Next-Generation Sequencing. Clin Chem. Mar. 2010; 56(3):336-8.

Voelkerding et al., Next generation sequencing: from basic research to diagnostics. Clin Chem Apr. 2009; 55(4):641-58.

Vogelstein & Kinzler, Digital PCR. Proc Natl Acad Sci Aug. 1999; 96:9236-9241.

Wheeler et al., The complete genome of an individual by massively parallel DNA sequencing. Nature. Apr. 17, 2008; 452(7189):872-6.

Wright et al., The use of cell-free nucleic acids in maternal blood for non-invasive prenatal diagnosis. Hum Reprod Update. Jan.-Feb. 2009; 15(1):139-51.

Zimmerman & Pheiffer, Macromolecular crowding allows blunt-end ligation by DNA ligase from rat liver or *Escheridia coli*. Proc Natl Acas Sci USA. Oct. 1983; 80(19)5852-6.

Examination Report dated Feb. 24, 2012 in U.K. Patent Application No. 1106394.8.

International Search Report and Written Opinion dated Sep. 17, 2012 for International Application No. PCT/US2011/032554.

Office Action dated May 23, 2012 in U.S. Appl. No. 13/333,832.

Office Action dated Nov. 1, 2012 in U.S. Appl. No. 13/333,832.

Final Office Action dated Jan. 22, 2013 in U.S. Appl. No. 13/333,832.

Office Action dated Oct. 10, 2012 in U.S. Appl. No. 12/958,352.

Office Action dated Dec. 20, 2012 in U.S. Appl. No. 12/958,353.

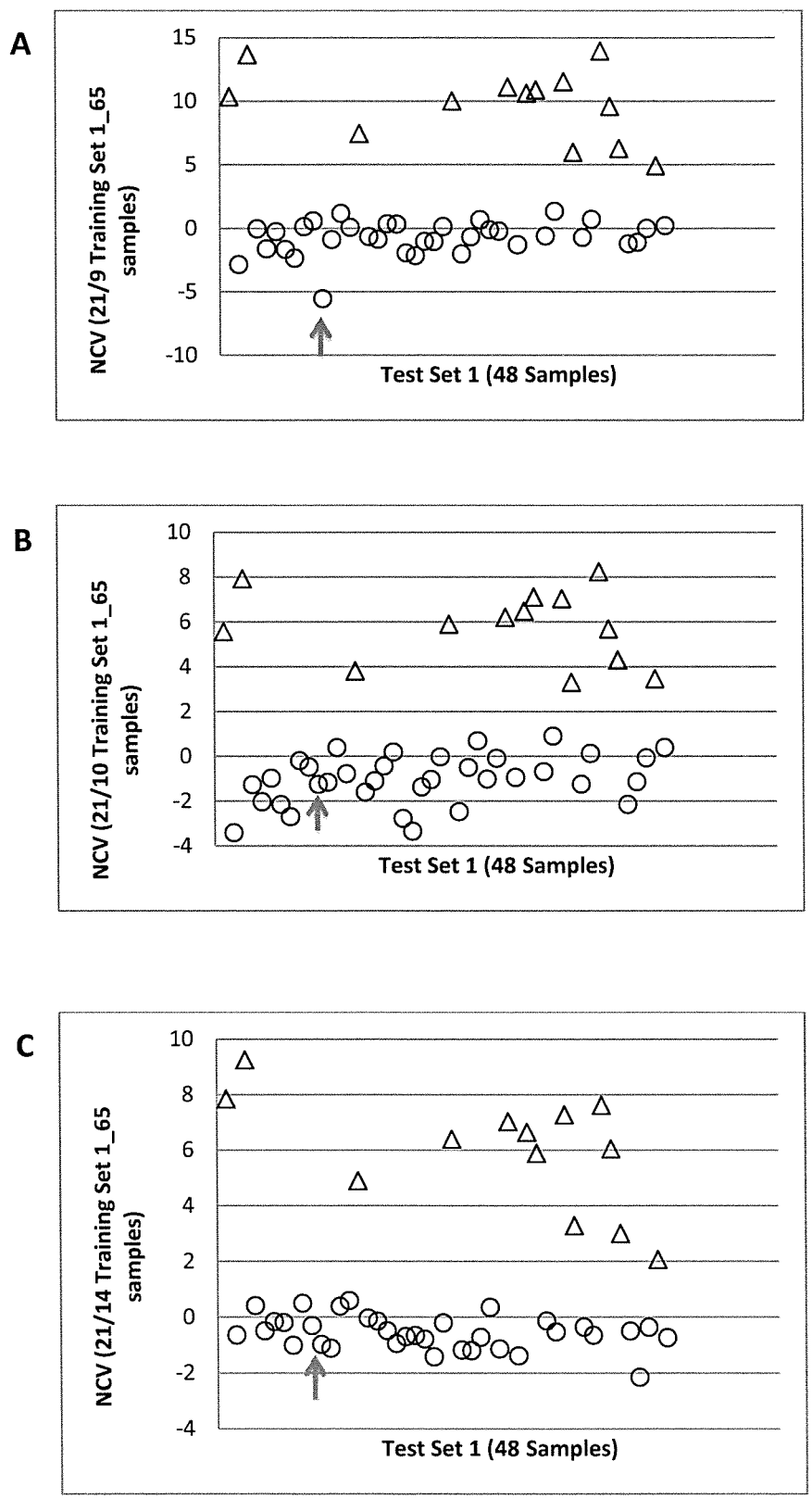
FIGURE 8 A-C

A
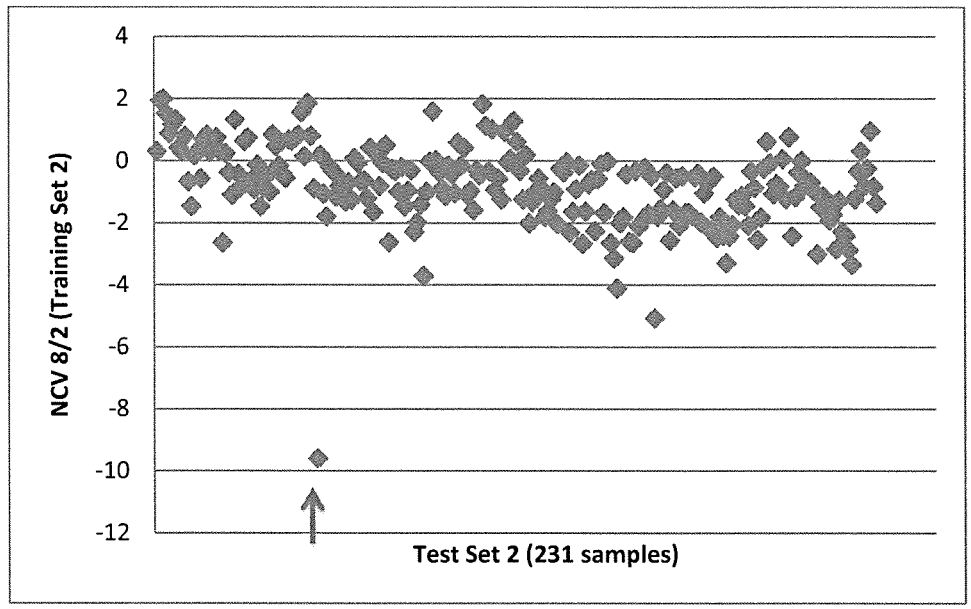
B
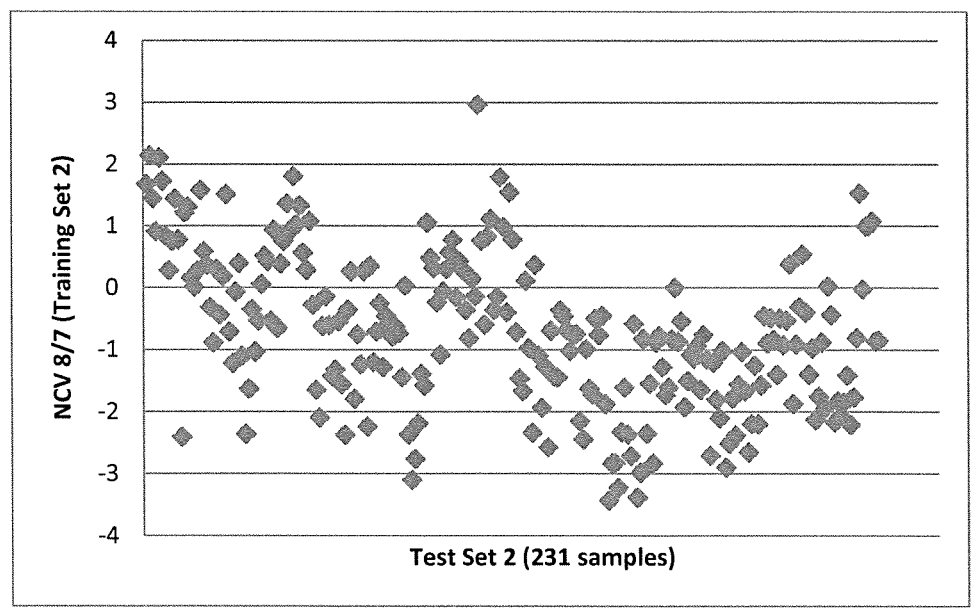
FIGURE 9 A-B

US 8,532,936 B2

NORMALIZING CHROMOSOMES FOR THE DETERMINATION AND VERIFICATION OF COMMON AND RARE CHROMOSOMAL ANEUPLOIDIES

CROSS-REFERENCE TO RELATED APPLICATION

This application claims the benefit of United Kingdom Patent Application Number 1106394.8 filed on Apr. 14, 2011, which is herein incorporated by reference in its entirety.

FIELD OF THE INVENTION

The present invention provides a method capable of determining single or multiple fetal chromosomal aneuploidies in a maternal sample comprising fetal and maternal nucleic acids, and verifying that the correct determination has been made. The method is applicable at least to the practice of noninvasive prenatal diagnostics, and to the diagnosis and monitoring of conditions associated with a difference in sequence representation in healthy versus diseased individuals.

BACKGROUND OF THE INVENTION

The American College of Obstetrics and Gynecology (ACOG) Practice Bulletin Number 77 published in 2007 supports that first trimester aneuploidy risk assessment, based on nuchal translucency measurement and surrogate biochemical markers to screen for Down syndrome, for all pregnant women (ACOG Practice Bulletin No. 77, Obstet Gynecol 109:217-227 [2007]). These screening tests can only provide a risk determination that is inconclusive and has non-optimal determination and high false positive rates. Today, only invasive methods including chorionic villus sampling (CVS), amniocentesis or cordocentesis provide definite genetic information about the fetus, but these procedures are associated with risks to both mother and fetus (Odibo et al., Obstet Gynecol 112:813-819 [2008]; Odibo et al., Obstet Gynecol 111:589-595 [2008]; Evans and Wapner, Semin Perinatol 29:215-218 [2005]). Therefore, a non-invasive means to obtain definite information on fetal chromosomal status is desirable.

Massively parallel DNA sequencing of cfDNA obtained from the maternal plasma yields millions of short sequence tags that can be aligned and uniquely mapped to sites from a reference human genome, and the counting of the mapped tags can be used to determine the over- or under-representation of a chromosome (Fan et al., Proc Natl Acad Sci USA 105:16266-16271 [2008]; Voelkerding and Lyon, Clin Chem 56:336-338 [2010]). However, the depth of sequencing and subsequent counting statistics determines the sensitivity of determination for fetal aneuploidy. The requirement for an optimized algorithm to determine chromosomal aneuploidies in maternal plasma samples is underscored by the apparent inability to determine more than one type of trisomy in a population of test samples (Chiu et al., BMJ 342, c7401 [2011]; Ehrich et al., Am J Obstet Gynecol 2014:205 e1 [2011]).

The limitations of the existing methods underlie the need for optimal noninvasive methods that would provide any or all of the specificity, sensitivity, and applicability to reliably diagnose chromosomal aneuploidies for prenatal diagnoses and for the diagnoses and monitoring of medical conditions associated with copy number changes.

The present invention fulfills some of the above needs and in particular offers an advantage in providing a reliable method having sufficient sensitivity to determine single or multiple chromosomal aneuploidies, and which verifies that the correct determination is made.

SUMMARY OF THE INVENTION

The present invention provides a method capable of determining single or multiple fetal chromosomal aneuploidies in a maternal sample comprising fetal and maternal nucleic acids, and verifying that the correct determination has been made. The method is applicable to determining copy number variations (CNV) of any sequence of interest in samples comprising mixtures of genomic nucleic acids derived from two different genomes, and which are known or are suspected to differ in the amount of one or more sequence of interest. The method is applicable at least to the practice of noninvasive prenatal diagnostics, and to the diagnosis and monitoring of conditions associated with a difference in sequence representation in healthy versus diseased individuals.

In one embodiment, the method determines the presence or absence of a fetal chromosomal aneuploidy in a maternal test sample comprising fetal and maternal nucleic acid molecules by: (a) obtaining sequence information for the fetal and maternal nucleic acids in the maternal sample to identify a number of sequence tags for a chromosome of interest and a number of sequence tags for at least two normalizing chromosomes; (b) using the number of sequence tags to calculate a first and a second normalizing value for the chromosome of interest; and (c) comparing the first normalizing value for the chromosome of interest to a first threshold value and comparing the second normalizing value for the chromosome of interest to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said chromosome of interest to a threshold value verifies the determination of the presence or absence of an aneuploidy for the chromosome of interest. In some embodiments, the first normalizing value is a first chromosome dose, which is a ratio of the number of sequence tags for the chromosome of interest and a first normalizing chromosome, and the second normalizing value is a second chromosome dose, which is a ratio of the number of sequence tags for the chromosome of interest and a second normalizing chromosome. Optionally, the first and second normalizing values can be expressed as normalized chromosome values (NCV) as described below.

In the above and all subsequent embodiments, the step of obtaining sequencing information comprises next generation sequencing (NGS). NGS can be sequencing-by-synthesis using reversible dye terminators. Alternatively, NGS can be sequencing sequencing-by-ligation. NGS can also be single molecule sequencing.

Similarly, in the above and all subsequent embodiments, the normalizing chromosomes for chromosome 21 are selected from chromosomes 9, 11, 14, and 1. In some embodiments, the normalizing chromosomes for chromosome 18 are selected from chromosomes 8, 3, 2, and 6. In some embodiments, the normalizing chromosomes for chromosome 13 are selected from chromosome 4, the group of chromosomes 2-6, chromosome 5, and chromosome 6. In some embodiments, the normalizing chromosomes for chromosome X are selected from chromosomes 6, 5, 13, and 3. In some embodiments, the normalizing chromosomes for chromosome 1 are selected from chromosomes 10, 11, 9 and 15. In some embodiments, the normalizing chromosomes for chromosome 2 are selected from chromosomes 8, 7, 12, and 14. In some embodiments, the normalizing chromosomes for chromosome 3 are selected from chromosomes 6, 5, 8, and 18. In some embodiments, the normalizing chromosomes for chromosome 4 are selected from chromosomes 3, 5, 6, and 13. In some embodiments, the normalizing chromosomes for chromosome 5 are selected from chromosomes 6, 3, 8, and 18. In some embodiments, the normalizing chromosomes for chromosome 6 are selected from chromosomes 5, 3, 8, and 18. In some embodiments, the normalizing chromosomes for chromosome 7 are selected from chromosomes 12, 2, 14 and 8. In some embodiments, the normalizing chromosomes for chromosome 8 are selected from chromosomes 2, 7, 12, and 3. In some embodiments, the normalizing chromosomes for chromosome 9 are selected from chromosomes 11, 10, 1, and 14. In some embodiments, the normalizing chromosomes for chromosome 10 are selected from chromosomes 1, 11, 9, and 15. In some embodiments, the normalizing chromosomes for chromosome 11 are selected from chromosomes 1, 10, 9, and 15. In some embodiments, the normalizing chromosomes for chromosome 12 are selected from chromosomes 7, 14, 2, and 8. In some embodiments, the d normalizing chromosomes for chromosome 14 are selected from chromosomes 12, 7, 2, and 9. In some embodiments, the normalizing chromosomes for chromosome 15 are selected from chromosomes 1, 10, 11, and 9. In some embodiments, the normalizing chromosomes for chromosome 16 are selected from chromosomes 20, 17, 15, and 1. In some embodiments, the normalizing chromosomes for chromosome 17 are selected from chromosomes 16, 20, 19 and 22. In some embodiments, the normalizing chromosomes for chromosome 19 are selected from 22, 17, 16, and 20. In some embodiments, the normalizing chromosomes for chromosome 20 are selected from chromosomes 16, 17, 15, and 1. In some embodiments, the normalizing chromosomes for chromosome 22 are selected from chromosomes 19, 17, 16, and 20.

In another embodiment, the method determines the presence or absence of a fetal chromosomal aneuploidy in a maternal test sample comprising fetal and maternal nucleic acid molecules by: (a) obtaining sequence information for the fetal and maternal nucleic acids in the maternal sample to identify a number of sequence tags for a chromosome of interest and a number of sequence tags for at least two normalizing chromosomes; (b) using the number of sequence tags to calculate a first and a second normalizing value for the chromosome of interest; and (c) comparing the first normalizing value for the chromosome of interest to a first threshold value and comparing the second normalizing value for the chromosome of interest to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said chromosome of interest to a threshold value verifies the determination of the presence or absence of an aneuploidy for the chromosome of interest. In some embodiments, the first normalizing value is a first chromosome dose, which is a ratio of the number of sequence tags for the chromosome of interest and a first normalizing chromosome, and the second normalizing value is a second chromosome dose, which is a ratio of the number of sequence tags for the chromosome of interest and a second normalizing chromosome. Optionally, the first and second normalizing values can be expressed as normalized chromosome values (NCV) as described below. The fetal chromosomal aneuploidy can be a partial or a complete chromosomal aneuploidy. In these embodiments, the fetal chromosomal aneuploidy can be selected from trisomy 21 (T21), trisomy 18 (T18), trisomy 13 (T13), monosomy X. In some embodiments, the maternal sample is obtained from a pregnant woman. In some embodiments, the maternal sample is a biological fluid sample e.g. a blood sample or the plasma fraction derived therefrom. In some embodiments, the maternal sample is a plasma sample. In some embodiments, the nucleic acids in the maternal sample are cfDNA molecules. In some other embodiments, the maternal test sample is a plasma sample obtained from a pregnant woman and the nucleic acid molecules are cfDNA molecules.

In another embodiment, the method determines the presence or absence of at least two different chromosomal aneuploidies. In one embodiment, the method determines the presence or absence of at least two different fetal chromosomal aneuploidies in a maternal test sample comprising fetal and maternal nucleic acid molecules by repeating the steps (a)-(c) for at least two chromosomes of interest, wherein the steps comprise (a) obtaining sequence information for the fetal and maternal nucleic acids in the maternal sample to identify a number of sequence tags for a chromosome of interest and a number of sequence tags for at least two normalizing chromosomes; (b) using the number of sequence tags to calculate a first and a second normalizing value for the chromosome of interest; and (c) comparing the first normalizing value for the chromosome of interest to a first threshold value and comparing the second normalizing value for the chromosome of interest to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said chromosome of interest to a threshold value verifies the determination of the presence or absence of an aneuploidy for the chromosome of interest. In some embodiments, the first normalizing value is a first chromosome dose, which is a ratio of the number of sequence tags for the chromosome of interest and a first normalizing chromosome, and the second normalizing value is a second chromosome dose, which is a ratio of the number of sequence tags for the chromosome of interest and a second normalizing chromosome. Optionally, the first and second normalizing values can be expressed as normalized chromosome values (NCV) as described herein. In some embodiments, the method comprises repeating the method for all chromosomes to determine the presence or absence of at least two different fetal chromosomal aneuploidies.

In another embodiment, the method determines the presence or absence of at least two different chromosomal aneuploidies. In one embodiment, the method determines the presence or absence of at least two different fetal chromosomal aneuploidies in a maternal test sample comprising fetal and maternal nucleic acid molecules by repeating the steps (a)-(c) for at least two chromosomes of interest, wherein the steps comprise (a) obtaining sequence information for the fetal and maternal nucleic acids in the maternal sample to identify a number of sequence tags for a chromosome of interest and a number of sequence tags for at least two normalizing chromosomes; (b) using the number of sequence tags to calculate a first and a second normalizing value for the chromosome of interest; and (c) comparing the first normalizing value for the chromosome of interest to a first threshold value and comparing the second normalizing value for the chromosome of interest to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said chromosome of interest to a threshold value verifies the determination of the presence or absence of an aneuploidy for the chromosome of interest. In some embodiments, the first normalizing value is a first chromosome dose, which is a ratio of the number of sequence tags for the chromosome of interest and a first normalizing chromosome, and the second normalizing value is a second chromosome dose, which is a ratio of the number of sequence tags for the chromosome of interest and a second normalizing chromosome. Optionally, the first and second normalizing values can be expressed as normalized chromosome values (NCV) as described herein. In some embodiments, the method comprises repeating the method for all chromosomes to determine the presence or absence of at least two different fetal chromosomal aneuploidies. The at least two different fetal chromosomal aneuploidies can be selected from T21, T18, T13, and monosomy X. In some embodiments, the maternal sample is obtained from a pregnant woman. In some embodiments, the maternal sample is a biological fluid sample e.g. a blood sample or the plasma fraction derived therefrom. In some embodiments, the maternal sample is a plasma sample. In some embodiments, the nucleic acids in the maternal sample are cfDNA molecules. In some other embodiments, the maternal test sample is a plasma sample obtained from a pregnant woman and the nucleic acid molecules are cfDNA molecules.

In another embodiment, the method verifies the determination of the presence or absence of an aneuploidy of a chromosome of interest in a maternal test sample comprising fetal and maternal nucleic acid molecules by: (a) obtaining sequence information for the fetal and maternal nucleic acids in the sample to identify a number of mapped sequence tags for a chromosome of interest and a number of sequence tags for at least two normalizing chromosomes; (b) using the number of tags for the chromosome of interest and the number of tags for a first normalizing chromosome to determine a first normalizing value for the chromosome of interest, and using the number of sequence tags for the first normalizing chromosome and the number of sequence tags for a second normalizing chromosome to determine a second normalizing value for the first normalizing chromosome; and (c) comparing the first normalizing value for the chromosome of interest to a first threshold value and comparing the second normalizing value for the first normalizing chromosome to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said first normalizing chromosome to a threshold value verifies the determination of the presence or absence of an aneuploidy for the chromosome of interest. In some embodiments, the first normalizing value is a first chromosome dose, which is a ratio of the number of sequence tags for said chromosome of interest and a first normalizing chromosome, and the second normalizing value a second chromosome dose, which is a ratio of the number of sequence tags for the first normalizing chromosome and a second normalizing chromosome. Optionally, the first and second normalizing values can be expressed as normalized chromosome values (NCV) calculated as described below.

In another embodiment, the method verifies the determination of the presence or absence of an aneuploidy of a chromosome of interest in a maternal test sample comprising fetal and maternal nucleic acid molecules by: (a) obtaining sequence information for the fetal and maternal nucleic acids in the sample to identify a number of mapped sequence tags for a chromosome of interest and a number of sequence tags for at least two normalizing chromosomes; (b) using the number of tags for the chromosome of interest and the number of tags for a first normalizing chromosome to determine a first normalizing value for the chromosome of interest, and using the number of sequence tags for the first normalizing chromosome and the number of sequence tags for a second normalizing chromosome to determine a second normalizing value for the first normalizing chromosome; and (c) comparing the first normalizing value for the chromosome of interest to a first threshold value and comparing the second normalizing value for the first normalizing chromosome to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said first normalizing chromosome to a threshold value verifies the determination of the presence or absence of an aneuploidy for the chromosome of interest. In some embodiments, the first normalizing value is a first chromosome dose, which is a ratio of the number of sequence tags for said chromosome of interest and a first normalizing chromosome, and the second normalizing value a second chromosome dose, which is a ratio of the number of sequence tags for the first normalizing chromosome and a second normalizing chromosome. Optionally, the first and second normalizing values can be expressed as normalized chromosome values (NCV) calculated as described below. The fetal chromosomal aneuploidy can be a partial or a complete chromosomal aneuploidy. In these embodiments, the fetal chromosomal aneuploidy can be selected from T21, T13, T18, and Monosomy X. In some embodiments, the maternal sample is obtained from a pregnant woman. In some embodiments, the maternal sample is a biological fluid sample e.g. a blood sample or the plasma fraction derived therefrom. In some embodiments, the maternal sample is a plasma sample. In some embodiments, the nucleic acids in the maternal sample are ctDNA molecules. In some other embodiments, the maternal test sample is a plasma sample obtained from a pregnant woman and the nucleic acid molecules are cfDNA molecules.

In another embodiment, the method determines the presence or absence of at least two different fetal chromosomal aneuploidies in a maternal test sample comprising fetal and maternal nucleic acid molecules by repeating the steps (a)-(c) for at least two chromosomes of interest, wherein steps (a)-(c) for each of the at least two chromosomes of interest comprise (a) obtaining sequence information for the fetal and maternal nucleic acids in the sample to identify a number of mapped sequence tags for a chromosome of interest and a number of sequence tags for at least two normalizing chromosomes; (b) using the number of tags for the chromosome of interest and the number of tags for a first normalizing chromosome to determine a first normalizing value for the chromosome of interest, and using the number of sequence tags for the first normalizing chromosome and the number of sequence tags for a second normalizing chromosome to determine a second normalizing value for the first normalizing chromosome; and (c) comparing the first normalizing value for the chromosome of interest to a first threshold value and comparing the second normalizing value for the first normalizing chromosome to a second threshold value to determine the presence or absence of a fetal aneuploidy in the sample. The first and second threshold values can be the same or they can be different. In step (c) of this method, for each of the at least two chromosomes of interest, the comparison of the first normalizing value for said chromosome of interest to a threshold value indicates the presence or absence of an aneuploidy for said chromosome of interest, and the comparison of the second normalizing value for said first normalizing chromosome to a threshold value verifies the determination of the presence or absence of an aneuploidy for the chromosome of interest. In some embodiments, the first normalizing value is a first chromosome dose, which is a ratio of the number of sequence tags for said chromosome of interest and a first normalizing chromosome, and the second normalizing value a second chromosome dose, which is a ratio of the number of sequence tags for the first normalizing chromosome and a second normalizing chromosome. Optionally, the first and second normalizing values can be expressed as normalized chromosome values (NCV) as described herein. In some embodiments, the method comprises repeating the method for all chromosomes to determine the presence or absence of at least two different fetal chromosomal aneuploidies.

In another embodiment, the method determines the presence or absence of at least two different fetal chromosomal aneuploidies in a maternal test sample comprising fetal and maternal nucleic acid molecules by repeating the steps (a)-(c) for at least two chromosomes of interest, wherein steps (a)-(c) for each of the at least two chromosomes of interest comprise (a) obtaining sequence information for the fetal and maternal nucleic acids in the sample to identify a number of mapped sequence tags for a chromosome of interest and a number of sequence tags for at least two normalizing chromosomes; (b) using the number of tags for the chromosome of interest and the number of tags for a first normalizing chromosome to determine a first normalizing value for the chromosome of interest, and using the number of sequence tags for the first normalizing chromosome and the number of sequence tags for a second normalizing chromosome to determine a second normalizing value for the first normalizing chromosome; and (c) comparing the first normalizing value for the chromosome of interest to a first threshold value and comparing the second normalizing value for the first normalizing chromosome to a second threshold value to determine the presence or absence of a fetal aneuploidy in the sample. The first and second threshold values can be the same or they can be different. In step (c) of this method, for each of the at least two chromosomes of interest, the comparison of the first normalizing value for said chromosome of interest to a threshold value indicates the presence or absence of an aneuploidy for said chromosome of interest, and the comparison of the second normalizing value for said first normalizing chromosome to a threshold value verifies the determination of the presence or absence of an aneuploidy for the chromosome of interest. In some embodiments, the first normalizing value is a first chromosome dose, which is a ratio of the number of sequence tags for said chromosome of interest and a first normalizing chromosome, and the second normalizing value a second chromosome dose, which is a ratio of the number of sequence tags for the first normalizing chromosome and a second normalizing chromosome. Optionally, the first and second normalizing values can be expressed as normalized chromosome values (NCV) as described herein. In some embodiments, the method comprises repeating the method for all chromosomes to determine the presence or absence of at least two different fetal chromosomal aneuploidies. The at least two different fetal chromosomal aneuploidies can be selected from T21, T18, T13, and monosomy X. In some embodiments, the maternal sample is obtained from a pregnant woman. In some embodiments, the maternal sample is a biological fluid sample e.g. a blood sample or the plasma fraction derived therefrom. In some embodiments, the maternal sample is a plasma sample. In some embodiments, the nucleic acids in the maternal sample are cfDNA molecules. In some other embodiments, the maternal test sample is a plasma sample obtained from a pregnant woman and the nucleic acid molecules are cfDNA molecules.

In another embodiment, the method determines the presence or absence of a fetal chromosomal aneuploidy selected from trisomy 21, trisomy 18, trisomy 13, and monosomy X, in a maternal plasma test sample comprising fetal and maternal nucleic acid molecules e.g. cfDNA, by: (a) obtaining sequence information for the fetal and maternal nucleic acids in the maternal sample to identify a number of sequence tags for a chromosome of interest and a number of sequence tags for at least two normalizing chromosomes, wherein obtaining the sequence information comprises massively parallel sequencing-by-synthesis using reversible dye terminators; (b) using the number of sequence tags to calculate a first and a second normalizing value for the chromosome of interest; and (c) comparing the first normalizing value for the chromosome of interest to a first threshold value and comparing the second normalizing value for the chromosome of interest to a second threshold value to determine the presence or absence of a fetal aneuploidy in the sample. In some embodiments, the first normalizing value is a first chromosome dose, which is a ratio of the number of sequence tags for the chromosome of interest and a first normalizing chromosome, and the second normalizing value is a second chromosome dose, which is a ratio of the number of sequence tags for the chromosome of interest and a second normalizing chromosome. Optionally, the first and second normalizing values can be expressed as normalized chromosome values 3.0 (NCV) as described herein. In some embodiments, the method determines the presence or absence of at least two different chromosomal aneuploidies selected from trisomy 21, trisomy 18, trisomy 13, and monosomy X, in a maternal plasma test sample comprising fetal and maternal nucleic acid molecules e.g. cfDNA, by repeating steps (a)-(c) for at least two chromosomes of interest. The method can further comprise repeating the steps (a)-(c) for all chromosomes to determine the presence or absence of at least two fetal chromosomal aneuploidies. In some embodiments, the maternal sample is obtained from a pregnant woman. In some embodiments, the maternal sample is a biological fluid sample e.g. a blood sample or the plasma fraction derived therefrom. In some embodiments, the maternal sample is a plasma sample. In some embodiments, the nucleic acids in the maternal sample are cfDNA molecules. In some other embodiments, the maternal test sample is a plasma sample obtained from a pregnant woman and the nucleic acid molecules are cfDNA molecules.

In another embodiment, the method determines the presence or absence of a fetal chromosomal aneuploidy selected from trisomy 21, trisomy 18, trisomy 13, and monosomy X, in a maternal plasma test sample comprising fetal and maternal nucleic acid molecules e.g. cfDNA, by: (a) obtaining sequence information for the fetal and maternal nucleic acids in the sample to identify a number of mapped sequence tags for a chromosome of interest and a number of sequence tags for at least two normalizing chromosomes, wherein obtaining the sequence information comprises massively parallel sequencing-by-synthesis using reversible dye terminators; (b) using the number of tags for the chromosome of interest and the number of tags for a first normalizing chromosome to determine a first normalizing value for the chromosome of interest, and using the number of sequence tags for the first normalizing chromosome and the number of sequence tags for a second normalizing chromosome to determine a second normalizing value for the first normalizing chromosome; and (c) comparing the first normalizing value for the chromosome of interest to a first threshold value and comparing the second normalizing value for the first normalizing chromosome to a second threshold value to determine the presence or absence of a fetal aneuploidy in the sample. In some embodiments, the first normalizing value is a first chromosome dose, which is a ratio of the number of sequence tags for said chromosome of interest and a first normalizing chromosome, and the second normalizing value a second chromosome dose, which is a ratio of the number of sequence tags for the first normalizing chromosome and a second normalizing chromosome. Optionally, the first and second normalizing values can be expressed as normalized chromosome values (NCV) as described herein. In some embodiments, the method determines the presence or absence of at least two different chromosomal aneuploidies selected from trisomy 21, trisomy 18, trisomy 13, and monosomy X, in a maternal plasma test sample comprising fetal and maternal nucleic acid molecules e.g. cfDNA, by repeating steps (a)-(c) for at least two chromosomes of interest. The method can further comprise repeating the steps (a)-(c) for all chromosomes to determine the presence or absence of at least two fetal chromosomal aneuploidies. In some embodiments, the maternal sample is obtained from a pregnant woman. In some embodiments, the maternal sample is a biological fluid sample e.g. a blood sample or the plasma fraction derived therefrom. In some embodiments, the maternal sample is a plasma sample. In some embodiments, the nucleic acids in the maternal sample are cfDNA molecules. In some other embodiments, the maternal test sample is a plasma sample obtained from a pregnant woman and the nucleic acid molecules are cfDNA molecules.

In some of the above and some of the subsequent embodiments, obtaining sequence information for the fetal and maternal nucleic acids in the sample comprises sequencing fetal and maternal nucleic acid molecules in the sample.

INCORPORATION BY REFERENCE

All patents, patent applications, and other publications, including all sequences disclosed within these references, referred to herein are expressly incorporated by reference, to the same extent as if each individual publication, patent or patent application was specifically and individually indicated to be incorporated by reference. The citation of any document is not to be construed as an admission that it is prior art with respect to the present invention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 shows a plot of Normalized Chromosome Values for doses of chromosome 21 determined in 48 samples in Test set 1 comprising unaffected (○) and affected (Δ) i.e. trisomy 21 samples, using chromosome 9 (A), chromosome 10 (B), and chromosome 14 (C), respectively.

FIG. 9 shows a plot of Normalized Chromosome Values for doses of chromosome 8 determined in Test Set 2 (Example 4) using chromosome 2 as the normalizing chromosome (A), and using chromosome 7 as the normalizing chromosome (B).

DETAILED DESCRIPTION OF THE INVENTION

Figure 1:
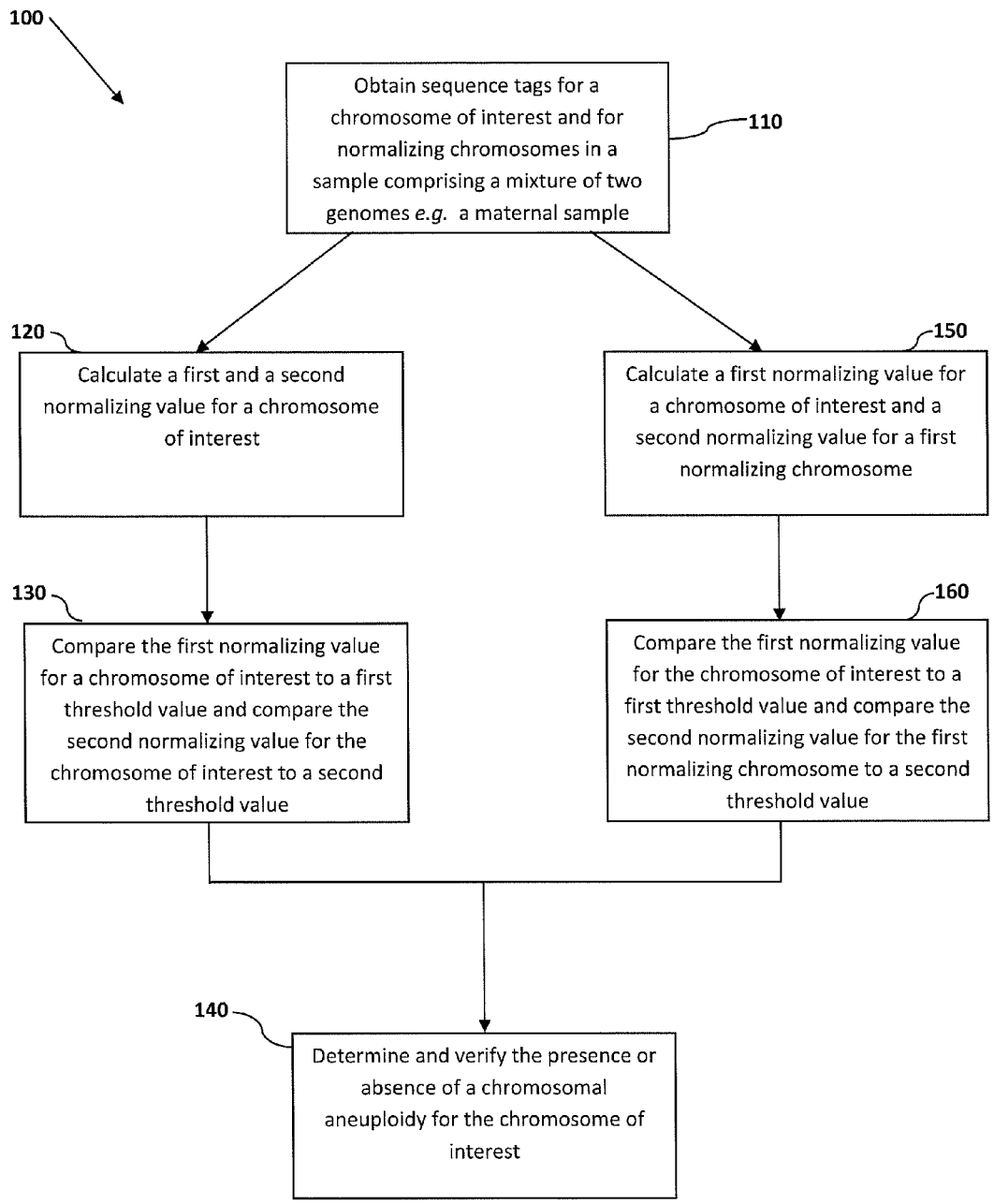
FIG. 1 provides a flowchart showing two alternate embodiments of the method that determines and verifies the presence or absence of an aneuploidy.

The present invention provides a method capable of determining single or multiple fetal chromosomal aneuploidies in a maternal sample comprising fetal and maternal nucleic acids, and verifying that the correct determination has been made. The method is applicable to determining copy number variations (CNV) of any sequence of interest in samples comprising mixtures of genomic nucleic acids derived from two different genomes, and which are known or are suspected to differ in the amount of one or more sequence of interest. The method is applicable at least to the practice of noninvasive prenatal diagnostics, and to the diagnosis and monitoring of conditions associated with a difference in sequence representation in healthy versus diseased individuals.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and reagents described, as these may vary, depending upon the context they are used by those of skill in the art.

DEFINITIONS

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation.

The term "obtaining sequence information" herein refers to sequencing nucleic acids to obtain sequence information in the form of sequence reads, which when uniquely mapped to a reference genome are identified as sequence tags.

The term "normalizing value" herein refers to a numerical value that is determined for a chromosome of interest and that relates the number of sequence tags for the chromosome of interest to the number of sequence tags for a normalizing chromosome. For example, a "normalizing value" can be a chromosome dose as described elsewhere herein, or it can be an NCV (Normalized Chromosome Value) as described elsewhere herein.

The term "chromosome of interest" herein refers to a chromosome for which a determination of the presence or absence of an aneuploidy is made. Examples of chromosomes of interest include chromosomes that are involved in common aneuploidies such as trisomy 21, and chromosomes that are involved in rare aneuploidies such as trisomy 2. Any one of chromosomes 1-22, X and Y can be chromosomes of interest.

The terms "multiple" and "plurality" when used in reference to a number of chromosomal aneuploidies and/or a number of chromosomes, herein refers to two or more aneuploidies and/or chromosomes.

The term "threshold value" herein refers to any number that is calculated using a training data set and serves as a limit of diagnosis of a copy number variation e.g. an aneuploidy, in an organism. If a threshold is exceeded by results obtained from practicing the invention, a subject can be diagnosed with a copy number variation e.g. trisomy 21. Appropriate threshold values for the methods described herein can be identified by analyzing normalizing values e.g. chromosome doses, or NCVs (normalized chromosome values) calculated for a training set of samples comprising qualified samples i.e. unaffected samples. Threshold values can be set using qualified samples and samples identified as having chromosomal aneuploidies i.e. affected samples (see the Examples herein). In some embodiments, the training set used to identify appropriate threshold values comprises at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, or more qualified samples. It may advantageous to use larger sets of qualified samples to improve the diagnostic utility of the threshold values.

The term "Next Generation Sequencing (NGS)" herein refers to sequencing methods that allow for massively parallel sequencing of clonally amplified and of single nucleic acid molecules. Non-limiting examples of NGS include sequencing-by-synthesis using reversible dye terminators, and sequencing-by-ligation.

The term "read" refers to a DNA sequence of sufficient length (e.g., at least about 30 bp) that can be used to identify a larger sequence or region, e.g. that can be aligned and specifically assigned to a chromosome or genomic region or gene.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags that can be mapped to more than one location on a reference genome i.e. tags that do not map uniquely, are not included in the analysis.

The term "number of sequence tags" when used in reference to the number of tags for a chromosome of interest and/or normalizing chromosome(s) herein refers to the sequence tags that map to the chromosome of interest and/or normalizing chromosome(s) that are a subset of the plurality of tags obtained for all chromosomes in the sample. The number of tags obtained for a sample can be at least about $1 \times 10^6$ sequence tags, at least about $2 \times 10^6$ sequence tags, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags, or at least about $60 \times 10^6$ sequence tags, or at least about $70 \times 10^6$ sequence tags, or at least about $80 \times 10^6$ sequence tags, comprising between 20 and 40 bp reads e.g. 36 bp, are obtained from mapping the reads to the reference genome per sample. The number of tags mapped to any one chromosome will depend on the size of the chromosome and the copy number of the chromosome. For example, the number of tags that map to chromosome 21 in a trisomy 21 sample will be different i.e. greater than the number of tags mapped to a chromosome 21 in an unaffected sample. Similarly, the number of tags mapped to chromosome 19 will be less than the number of tags that map to chromosome 1, which is about four times the size of chromosome 19. The number of tags mapped to a sequence of interest e.g. a chromosome, is also known as "sequence tag density".

The term "sequence tag density" herein refers to the number of sequence reads that are mapped to a reference genome sequence e.g. the sequence tag density for chromosome 21 is the number of sequence reads generated by the sequencing method that are mapped to chromosome 21 of the reference genome. Sequence tag density can be determined for whole chromosomes, or for portions of chromosomes.

As used herein, the terms "aligned", "alignment", or "aligning" refer to one or more sequences that are identified as a match in terms of the order of their nucleic acid molecules to a known sequence from a reference genome. Such alignment can be done manually or by a computer algorithm, examples including the Efficient Local Alignment of Nucleotide Data (ELAND) computer program distributed as part of the Illumina Genomics Analysis pipeline. The matching of a sequence read in aligning can be a 100% sequence match or less than 100% (non-perfect match).

As used herein, the term "reference genome" refers to any particular known genome sequence, whether partial or complete, of any organism or virus which may be used to reference identified sequences from a subject. For example, a reference genome used for human subjects as well as many other organisms is found on the world wide web at the National Center for Biotechnology Information.

A "genome" refers to the complete genetic information of an organism or virus, expressed in nucleic acid sequences.

The term "maternal sample" herein refers to a biological sample obtained from a pregnant subject e.g. a woman.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

The term "subject" herein refers to a human subject as well as a non-human subject such as a mammal, an invertebrate, a vertebrate, a fungus, a yeast, a bacteria, and a virus. Although the examples herein concern humans and the language is primarily directed to human concerns, the concept of this invention is applicable to genomes from any plant or animal, and is useful in the fields of veterinary medicine, animal sciences, and research laboratories and such.

The term "normalizing sequence" herein refers to a sequence that displays a variability in the number of sequence tags that are mapped to it among samples and sequencing runs that best approximates that of the sequence of interest for which it is used as a normalizing parameter, and that can best differentiate an affected sample from one or more unaffected samples. A "normalizing chromosome" is an example of a "normalizing sequence".

The term "sequence dose" herein refers to a parameter that relates the sequence tag density of a sequence of interest to the tag density of a normalizing sequence. A "chromosome dose", which is a ratio of the number of sequence tags mapped to a chromosome e.g. a chromosome of interest, and the number of sequence tags mapped to a normalizing chromosome is an example of a sequence dose. A "test sequence dose" is a parameter that relates the sequence tag density of a sequence of interest e.g. chromosome 21, to that of a normalizing sequence e.g. chromosome 9, determined in a test sample. Similarly, a "qualified sequence dose" is a parameter that relates the sequence tag density of a sequence of interest to that of a normalizing sequence determined in a qualified sample.

The term "chromosome dose" herein refers to a ratio of the number of sequence tags mapped to a chromosome e.g. a chromosome of interest, and the number of sequence tags mapped to a normalizing chromosome.

The term "normalizing chromosome" herein refers to a chromosome that displays a variability in the number of sequence tags that are mapped to it among samples and sequencing runs that best approximates that of the chromosome of interest for which it is used to obtain a normalizing value, and that can best differentiate an affected sample from one or more unaffected samples.

The term "sequence of interest" herein refers to a nucleic acid sequence that is associated with a difference in sequence representation in healthy versus diseased individuals. A sequence of interest can be a sequence on a chromosome that is misrepresented i.e. over- or under-represented, in a disease or genetic condition. A sequence of interest may also be a portion of a chromosome, or a chromosome i.e. chromosome of interest. For example, a sequence of interest can be a chromosome that is over-represented in an aneuploidy condition e.g. chromosomes 13, 18, 21, and X, or a gene encoding a tumor-suppressor that is under-represented in a cancer. Sequences of interest include sequences that are over- or under-represented in the total population, or a subpopulation of cells of a subject. A "qualified sequence of interest" is a sequence of interest in a qualified sample. A "test sequence of interest" is a sequence of interest in a test sample.

The term "qualified sample" herein refers to a sample comprising a mixture of nucleic acids that are present in a known copy number to which the nucleic acids in a test sample are compared, and it is a sample that is normal i.e. not aneuploid, for the sequence of interest e.g. a qualified sample used for identifying a normalizing chromosome for chromosome 21 is a sample that is not a trisomy 21 sample.

The terms "training set" and "training samples" are used herein to refer to samples comprising nucleic acids that are present in a known copy number to which the nucleic acids in a test sample are compared. Unless otherwise specified, a training set comprises qualified and affected samples.

The term "test sample" herein refers to a sample comprising a mixture of nucleic acids comprising at least one nucleic acid sequence whose copy number is suspected of having undergone variation. Nucleic acids present in a test sample are referred to as "test nucleic acids".

The term "aneuploidy" herein refers to an imbalance of genetic material caused by a loss or gain of a whole chromosome, or part of a chromosome.

The term "chromosomal aneuploidy" herein refers to an imbalance of genetic material caused by a loss or gain of a whole chromosome, and includes germline aneuploidy and mosaic aneuploidy.

The terms "partial aneuploidy" and "partial chromosomal aneuploidy" herein refer to an imbalance of genetic material caused by a loss or gain of part of a chromosome e.g. partial monosomy and partial trisomy, and encompasses imbalances resulting from translocations, deletions and insertions.

The terms "nucleic acid molecules", "polynucleotide", and "nucleic acids" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next, include sequences of any form of nucleic acid, including, but not limited to RNA, DNA and cfDNA molecules. The term "polynucleotide" includes, without limitation, single- and double-stranded polynucleotide.

The term "copy number variation (CNV)" herein refers to variation in the number of copies of a nucleic acid sequence that is present in a test sample in comparison with the copy number of the nucleic acid sequence present in a qualified sample i.e. normal sample. Copy number variations include deletions, including microdeletions, insertions, including microinsertions, duplications, multiplications, inversions, translocations and complex multi-site variants. CNV encompass complete chromosomal aneuploidies and partial aneuplodies.

DESCRIPTION

The present invention provides a method capable of determining single or multiple fetal chromosomal aneuploidies in a maternal sample comprising fetal and maternal nucleic acids, and verifying that the correct determination has been made. The method is applicable to determining copy number variations (CNV) of any sequence of interest in samples comprising mixtures of genomic nucleic acids derived from at least two different genomes and which are known or are suspected to differ in the amount of one or more sequence of interest. Sequences of interest include genomic sequences ranging from hundreds of bases to tens of megabases to entire chromosomes that are known or are suspected to be associated with a genetic or a disease condition. Examples of sequences of interest include chromosomes associated with well known aneuploidies e.g. trisomy 21, and segments of chromosomes that are multiplied in diseases such as cancer e.g. partial trisomy 8 in acute myeloid leukemia.

The present method comprises obtaining sequencing information to calculate chromosome doses for sequences of interest e.g. chromosomes, to determine the presence or absence of a single or multiple chromosomal aneuploidies in one or more maternal test samples, and comprises verifying that the correct determination of the aneuploidy is made. The accuracy required for correctly determining whether a CNV e.g. aneuploidy, is present or absent in a sample, is predicated on the variation of the number of sequence tags that map to the reference genome among samples within a sequencing run (intra-run sequencing variation), and the variation of the number of sequence tags that map to the reference genome in different sequencing runs (inter-run sequencing variation), which can obscure the effects of fetal chromosomal aneuploidies on the distribution of mapped sequence tags. For example, the variation can be particularly pronounced for tags that map to GC-rich or GC-poor reference sequences. To correct for such variation, the present method uses chromosome doses based on the knowledge of normalizing chromosomes (or groups of normalizing chromosomes), to intrinsically account for the accrued sequencing variability.

Normalizing Chromosomes and Chromosome Doses

Normalizing chromosomes are identified using sequence information from a set of qualified samples obtained from subjects known to comprise cells having a normal copy number for any one sequence of interest e.g. diploid for chromosome 21. The sequence information obtained from the qualified samples is also used for determining statistically meaningful identification of chromosomal aneuploidies in test samples (see Examples). In one embodiment, the qualified samples are obtained from mothers pregnant with a fetus that has been confirmed using cytogenetic means to have a normal copy number of chromosomes e.g. diploid for chromosome 21. The biological qualified samples may be a biological fluid e.g. plasma, or any suitable sample as described below. In some embodiments, the qualified sample contains a mixture of nucleic acid molecules e.g. cfDNA molecules. In some embodiments, the qualified sample is a maternal plasma sample that contains a mixture of fetal and maternal cfDNA molecules.

Sequence information for normalizing chromosomes is obtained by sequencing at least a portion of the nucleic acids e.g. fetal and maternal nucleic acids, using any known sequencing method. Preferably, any one of the Next Generation Sequencing (NGS) methods described elsewhere herein is used to sequence the fetal and maternal nucleic acids as single or clonally amplified molecules. Millions of sequence reads of a predetermined length e.g. 36 bp, are generated by the NGS technology, and are mapped to a reference genome to be counted as sequence tags. At least a portion of the nucleic acids of each of the qualified samples is sequenced and the number of sequence tags mapped to each chromosome is counted. In some embodiments, the number of sequence tags mapped to a chromosome can be normalized to the length of the qualified sequence of interest to which they are mapped. Sequence tag densities that are determined as a ratio of the tag density relative to the length of the sequence of interest are herein referred to as tag density ratios. Normalization to the length of the sequence of interest is not required, and may be included as a step to reduce the number of digits in a number to simplify it for human interpretation. As all qualified sequence tags are mapped and counted in each of the qualified samples, the qualified sequence tag density for a sequence of interest e.g. a clinically-relevant sequence, in the qualified samples is determined, as are the sequence tag densities for additional sequences from which normalizing sequences are identified subsequently.

Based on the calculated qualified tag densities, qualified sequence doses e.g. a chromosome doses, for a sequence of interest e.g. chromosome 21, are determined each as the ratio of the sequence tag density for the sequence of interest and the qualified sequence tag density for additional sequences from which normalizing sequences are identified subsequently. For example, chromosome doses for the chromosome of interest e.g. chromosome 21, are determined as a ratio of the sequence tag density of chromosome 21 and the sequence tag density for each of all the remaining chromosomes i.e. chromosomes 1-20, chromosome 22, chromosome X, and chromosome Y. Qualified sequence doses can be determined for all chromosomes.

Subsequently, at least two normalizing sequences for a sequence of interest e.g. chromosome 21, are identified in the qualified samples based on the calculated sequence doses. For example, the qualified normalizing sequences for chromosome 21 are identified as the sequences in qualified samples that have variation in sequence tag density that best approximate that of chromosome 21. For example, qualified normalizing sequences are sequences that have the smallest variability. In some embodiments, more than two normalizing sequences are identified. For example, normalizing chromosomes having the lowest variability for each of all chromosomes 1-22, chromosome X, and chromosome Y are determined. Table 9 in Example 5 provides the four normalizing chromosomes that were determined to have the four lowest variabilities for each of chromosomes 1-22, chromosome X, and chromosome Y. Variability can be represented numerically as a coefficient of variation (% CV) as is shown in the Examples. The normalizing sequences can also be sequences that best distinguish one or more qualified samples from one or more affected samples i.e. the normalizing sequences are sequences that have the greatest differentiability. The level of differentiability can be determined as a statistical difference between the chromosome doses in a population of qualified samples and the chromosome dose(s) in one or more test samples. For example, differentiability can be represented numerically as a T-test value, which represents the statistical difference between the chromosome doses in a population of qualified samples and the chromosome dose(s) in one or more test samples. Alternatively, differentiability can be represented numerically as a Normalized Chromosome Value (NCV), which is a z-score for chromosome doses as long as the distribution for the NCV is normal. In determining the z-score, the mean and standard deviation of chromosome doses in a set of qualified samples can be used. Alternatively, the mean and standard deviation of chromosome doses in a training set comprising qualified samples and affected samples can be used. In other embodiments, the normalizing sequence is a sequence that has the smallest variability and the greatest differentiability.

The method identifies sequences that inherently have similar characteristics and that are prone to similar variations among samples and sequencing runs, and which are useful for determining sequence doses in test samples.

Based on the identification of the normalizing sequence(s) in qualified samples, one or more sequence doses e.g. chromosome doses, are determined for a sequence of interest e.g. chromosome 21, in a test sample using the sequence information that is obtained for the nucleic acids in the test sample. In some embodiments, at least two sequence doses e.g. chromosome doses, are determined for a sequence of interest. For example, a first chromosome dose is determined for chromosome 21 using chromosome 9 as a first normalizing chromosome, and a second chromosome dose is determined for chromosome 21 using chromosome 11 as the second normalizing chromosome. The test sequence doses can be further expressed as NCVs, as described below. In some embodiments, classification of the test sample can be made by directly comparing the first test sequence dose for the chromosome of interest to a first threshold value and comparing the second test sequence dose to a second threshold value to determine the presence or absence of a chromosomal aneuploidy in the test sample. Comparison of two chromosome doses for a chromosome of interest verifies the determination of the sample classification. Threshold values are chosen according to a user-defined threshold of reliability to classify the sample as a "normal", an "affected" or a "no call" sample. In other embodiments, a first chromosome dose is determined for a chromosome of interest using a first normalizing chromosome, and a second chromosome dose is determined for the first normalizing chromosome using a second normalizing chromosome. Classification of the test sample can be made by comparing the first chromosome dose to a first threshold value and comparing the second chromosome dose to a second threshold value to determine the presence or absence of a chromosomal aneuploidy in the test sample. Comparison of a chromosome dose for a chromosome of interest to a first threshold determines the presence or absence of aneuploidy for the chromosome of interest in the test sample, and comparison of the second chromosome dose for the normalizing chromosome to a second threshold verifies the determination of the sample classification. The test chromosome doses can be further expressed as NCVs, as described below, where the first and second chromosome doses are expressed as first and second NCVs; and classification of test samples is made by comparing the first NCV to a first threshold and the second NCV to a second threshold.

Although the examples herein concern complete chromosomal aneuploidies, the concept of this invention is applicable to partial aneuploidies. In one embodiment, the sequence of interest is a segment of a chromosome associated with a partial aneuploidy, e.g. a chromosomal deletion or insertion, or unbalanced chromosomal translocation, and the at least two normalizing sequences are chromosomal segments that are not associated with the partial aneuploidy and whose variation in sequence tag density best approximates that of the chromosome segment associated with the partial aneuploidy. Partial aneuploidies can be determined using chromosome doses (see International Application PCT/US2010/058609 filed on Dec. 1, 2010, and U.S. patent application Ser. No. 12/958,352, entitled "Method for Determining Copy Number Variations", which were filed on Dec. 1, 2010, which are herein incorporated by reference in their entirety). The presence or absence of a partial aneuploidy can be verified using at least two normalizing sequences according to the present method.

FIG. 1 provides a flow chart of two exemplary embodiments of the method 100, which determines and verifies the presence or absence of a chromosomal aneuploidy in a sample comprising a mixture of two genomes e.g. a maternal sample.

In a first embodiment, the method determines the presence or absence of a fetal chromosomal aneuploidy in a maternal test sample comprising fetal and maternal nucleic acids by: (a) obtaining sequence information for the fetal and maternal nucleic acids in the maternal sample to identify a number of sequence tags for a chromosome of interest and a number of sequence tags for at least two normalizing chromosomes; (b) using the number of sequence tags to calculate a first and a second normalizing value for the chromosome of interest; and (c) comparing the first normalizing value for the chromosome of interest to a first threshold value and comparing the second normalizing value for the chromosome of interest to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said chromosome of interest to a threshold value verifies the determination of the presence or absence of an aneuploidy for the chromosome of interest. In some embodiments, the first normalizing value is a first chromosome dose, which is a ratio of the number of sequence tags for the chromosome of interest and a first normalizing chromosome, and the second normalizing value is a second chromosome dose, which is a ratio of the number of sequence tags for the chromosome of interest and a second normalizing chromosome. Optionally, the first and second normalizing values can be expressed as normalized chromosome values (NCV) as described below.

The first embodiment is depicted according to steps 110, 120, 130, and 140 of the method as shown in FIG. 1. Fetal and maternal nucleic acids obtained from a maternal sample are sequenced to provide a number of sequence tags (110). The sequence tags mapped to a chromosome of interest e.g. chromosome 21, and the sequence tags mapped to two normalizing chromosomes e.g. chromosome 9 and chromosome 11, are counted and used to calculate a corresponding first and second normalizing values e.g. chromosome doses, for the chromosome of interest. In one embodiment, at least two chromosome doses are the normalizing values that are determined for each chromosome of interest. In one embodiment, the first normalizing value for the chromosome of interest is a first chromosome dose, which is a ratio of the number of sequence tags for the chromosome of interest and a first normalizing chromosome, and the second normalizing value for the chromosome of interest is a second chromosome dose, which is a ratio of the number of sequence tags for the chromosome of interest and a second normalizing chromosome (120). The first normalizing value for the chromosome of interest i.e. first chromosome dose, is compared to a first threshold value and the second normalizing value for the chromosome of interest i.e. second chromosome dose, is compared to a second threshold value (130), and the determination and verification of the presence or absence of a chromosomal aneuploidy is made (140). Alternatively, the at least two chromosome doses are expressed as a first and second normalized chromosome values (NCVs), which first NCV relates the first chromosome dose to the mean of the corresponding first chromosome dose in a set of qualified samples, and the second NCV relates the second chromosome dose to the mean of the corresponding chromosome dose in the same set of qualified samples as:

$$NCV_{ij} = \frac{x_{ij} - \hat{\mu}_j}{\hat{\sigma}_j}$$

where $\hat{\mu}_j$ AND $\hat{\sigma}_j$ are the estimated mean and standard deviation, respectively, for the j-th chromosome dose in a set of qualified samples, and $x_{ij}$ is the observed j-th chromosome dose for test sample i. The first and second normalizing values i.e. NCVs are each compared to a first and a second threshold, respectively (130), and the determination and verification of the presence or absence of a chromosomal aneuploidy is made (140). The method is capable of identifying very rare e.g. trisomy 9, and more common chromosomal aneuploidies, e.g. trisomy 21, and can identify multiple chromosomal aneuploidies from sequencing information obtained from a single sequencing run on a test sample nucleic acid e.g. cfDNA. As is shown in the Examples, sequence information obtained for a sample to determine the presence or absence of trisomy 21, revealed that while a trisomy 21 was absent, the sample contained a trisomy 9. In some embodiments, chromosomal aneuploidies are identified in any of chromosomes 1-22, chromosome X and chromosome Y. The chromosomal aneuploidy can be identified in the chromosome of interest and/or in the first or second normalizing chromosome. In some embodiments, the method identifies multiple chromosomal aneuploidies selected from trisomy 21, trisomy 13, trisomy 18 and monosomy X.

In a second embodiment, the method verifies the determination of the presence or absence of an aneuploidy of a chromosome of interest in a maternal test sample comprising fetal and maternal nucleic acid molecules by: (a) obtaining sequence information for the fetal and maternal nucleic acids in the sample to identify a number of mapped sequence tags for a chromosome of interest and a number of sequence tags for at least two normalizing chromosomes; (b) using the number of tags for the chromosome of interest and the number of tags for a first normalizing chromosome to determine a first normalizing value for the chromosome of interest, and using the number of sequence tags for the first normalizing chromosome and the number of sequence tags for a second normalizing chromosome to determine a second normalizing value for the first normalizing chromosome; and (c) comparing the first normalizing value for the chromosome of interest to a first threshold value and comparing the second normalizing value for the first normalizing chromosome to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said first normalizing chromosome to a threshold value verifies the determination of the presence or absence of an aneuploidy for the chromosome of interest. In some embodiments, the first normalizing value is a first chromosome dose, which is a ratio of the number of sequence tags for said chromosome of interest and a first normalizing chromosome, and the second normalizing value a second chromosome dose, which is a ratio of the number of sequence tags for the first normalizing chromosome and a second normalizing chromosome. Optionally, the first and second normalizing values can be expressed as normalized chromosome values (NCV) calculated as $$NCV_{ij} = \frac{x_{ij} - \hat{\mu}_j}{\hat{\sigma}_j}$$

as described above.

The second embodiment is depicted according to steps 110, 150, 160, and 140 of the method as shown in FIG. 1. Fetal and maternal nucleic acids obtained from a maternal sample are sequenced to provide a number of sequence tags (110). The sequence tags mapped to a chromosome of interest e.g. chromosome 21, and the sequence tags mapped to a normalizing chromosome e.g. chromosome 9, are counted and used to calculate a corresponding first normalizing value e.g. chromosome dose, for the chromosome of interest, and a second normalizing value e.g. a chromosome dose, is calculated for the first normalizing chromosome as a ratio of the sequence tags mapped to the first normalizing chromosome e.g. chromosome 9, and the number of sequence tags mapped to a second normalizing chromosome e.g. chromosome 11 (150). The first and second normalizing values i.e. chromosome doses are each compared to a first and second threshold, respectively (160), and the determination and verification of the presence or absence of a chromosomal aneuploidy is made (140). Alternatively, the two normalizing values i.e. the two chromosome doses, are expressed as a first and second normalized chromosome values (NCVs), which first NCV relates the first chromosome dose to the mean of the corresponding first chromosome close in a set of qualified samples, and the second NCV relates the second chromosome dose to the mean of the corresponding chromosome dose in the same set of qualified samples as:

$$NCV_{ij} = \frac{x_{ij} - \hat{\mu}_j}{\hat{\sigma}_j}$$

where $\hat{\mu}_j$ AND $\hat{\sigma}_j$ are the estimated mean and standard deviation, respectively, for the j-th chromosome dose in a set of qualified samples, and $x_{ij}$ is the observed j-th chromosome dose for test sample i. The first and second normalizing values i.e. NCVs are each compared to a predetermined threshold (160), and the determination and verification of the presence or absence of a chromosomal aneuploidy is made (140).

As described previously, the method is capable of identifying rare aneuploidies e.g. trisomy 9, and common aneuploidies e.g. trisomy 21, chromosomal aneuploidies, and can identify multiple chromosomal aneuploidies from sequencing information obtained from a single sequencing run on a test sample nucleic acid e.g. cfDNA. In some embodiments, single or multiple chromosomal aneuploidies are identified in any of chromosomes 1-22, chromosome X and chromosome Y. The chromosomal aneuploidy can be identified in the chromosome of interest and/or in the first or second normalizing chromosome. In some embodiments, the method identifies single or multiple chromosomal aneuploidies selected from trisomy 21, trisomy 13, trisomy 18, trisomy 9, and monosomy X.

Normalizing chromosomes can be determined in one or more separate sets of qualified samples. In some embodiments, normalizing chromosomes can be determined in one or more sets of qualified samples for all chromosomes in a genome. Determining normalizing chromosomes for all chromosomes in a genome allows for the determination of chromosomal aneuploidies in each of the chromosomes of the genome using sequencing information obtained from a single sequencing run of nucleic acids from a test sample.

In all embodiments, normalizing chromosomes can be selected as follows.

Normalizing chromosomes for chromosome 1 are selected from chromosomes 10, 11, 9 and 15. In one embodiment, the first and second normalizing chromosomes for chromosome 1 are chromosome 10 and chromosome 11.

Normalizing chromosomes for chromosome 2 are selected from chromosomes 8, 7, 12, and 14. In one embodiment, the first and second chromosome normalizing chromosomes for chromosome 2 are chromosome 8 and chromosome 7.

Normalizing chromosomes for chromosome 3 are selected from chromosomes 6, 5, 8, and 18. In one embodiment, the first and second chromosome normalizing chromosomes for chromosome 3 are chromosome 6 and chromosome 5.

Normalizing chromosomes for chromosome 4 are selected from 3, 5, 6, and 13. In one embodiment, the first and second chromosome normalizing chromosomes for chromosome 4 are chromosome 13 and chromosome 5.

Normalizing chromosomes for chromosome 5 are selected from 6, 3, 8, and 18. In one embodiment, the first and second chromosome normalizing chromosomes for chromosome 5 are chromosome 6 and chromosome 3.

Normalizing chromosomes for chromosome 6 are selected from 5, 3, 8, and 18. In one embodiment, the first and second chromosome normalizing chromosomes for chromosome 6 are chromosome 5 and chromosome 3.

Normalizing chromosomes for chromosome 7 are selected from 12, 2, 14 and 8. In one embodiment, the first and second chromosome normalizing chromosomes for chromosome 7 are chromosome 12 and chromosome 2.

Normalizing chromosomes for chromosome 8 are selected from 2, 7, 12, and 3. In one embodiment, the first and second chromosome normalizing chromosomes for chromosome 8 are chromosome 2 and chromosome 3.

Normalizing chromosomes for chromosome 9 are selected from 11, 10, 1, and 14. In one embodiment, the first and second chromosome normalizing chromosomes for chromosome 9 are chromosome 11 and chromosome 10.

Normalizing chromosomes for chromosome 10 are selected from 1, 11, 9, and 15. In one embodiment, the first and second chromosome normalizing chromosomes for chromosome 10 are chromosome 1 and chromosome 11.

Normalizing chromosomes for chromosome 11 as the chromosome of interest are selected from 1, 10, 9, and 15. In one embodiment, the first and second chromosome normalizing chromosomes for chromosome 11 are chromosome 1 and chromosome 10.

Normalizing chromosomes for chromosome 12 are selected from 7, 14, 2, and 8. In one embodiment, the first and second chromosome normalizing chromosomes for chromosome 12 are chromosome 7 and chromosome 14.

Normalizing chromosomes for chromosome 13 are selected from chromosome 4, the group of chromosomes 2-6, chromosome 5, and chromosome 6. In one embodiment, the first and second chromosome normalizing chromosomes for chromosome 13 are chromosome 4 and the group of chromosomes 2-6, respectively. The group of chromosomes 2-6 can be used as a first or a second normalizing chromosome for chromosome of interest 13, and as a normalizing chromosome for a first normalizing chromosome that is used for chromosome 13. In some embodiments, verification of all chromosomes in the group can be performed. Two groups of chromosomes can be used as first and second normalizing chromosomes for chromosome 13, wherein the chromosomes of the first group are different from the chromosomes of the second group.

Normalizing chromosomes for chromosome 14 are selected from 12, 7, 2, and 9. In one embodiment, the first and second chromosome normalizing chromosomes for chromosome 14 are chromosome 12 and chromosome 7.

Normalizing chromosomes for chromosome 15 are selected from 1, 10, 11, and 9. In one embodiment, the first and second chromosome normalizing chromosomes for chromosome 2 are chromosome 1 and chromosome 10.

Normalizing chromosomes for chromosome 16 are selected from 20, 17, 15, and 1. In one embodiment, the first and second chromosome normalizing chromosomes for chromosome 16 are chromosome 20 and chromosome 17.

Normalizing chromosomes for chromosome 17 are selected from 16, 20, 19 and 22. In one embodiment, the first and second chromosome normalizing chromosomes for chromosome 17 are chromosome 16 and chromosome 20.

Normalizing chromosomes for chromosome 18 are selected from 8, 3, 2, and 6. In one embodiment, the first and second chromosome normalizing chromosomes for chromosome 18 are chromosome 8 and chromosome 3.

Normalizing chromosomes for chromosome 19 are selected from 22, 17, 16, and 20. In one embodiment, the first and second chromosome normalizing chromosomes for chromosome 19 are chromosome 22 and chromosome 17.

Normalizing chromosomes for chromosome 20 are selected from 16, 17, 15, and 1. In one embodiment, the first and second chromosome normalizing chromosomes for chromosome 20 are chromosome 16 and chromosome 17.

Normalizing chromosomes for chromosome 21 are selected from 9, 11, 14 and 1. In one embodiment, the first and second chromosome normalizing chromosomes for chromosome 21 are chromosome 9 and chromosome 11.

Normalizing chromosomes for chromosome 22 are selected from 19, 17, 16, and 20. In one embodiment, the first and second chromosome normalizing chromosomes for chromosome 22 are chromosome 19 and chromosome 17.

Normalizing chromosomes for chromosome X are selected from 6, 5, 13, and 3. In one embodiment, the first and second chromosome normalizing chromosomes for chromosome X are chromosome 6 and chromosome 5.

Normalizing chromosomes for chromosome Y are selected from the group of chromosomes 2-6, chromosome 3, chromosome 4, and chromosome 5. In another embodiment, the first and second chromosome normalizing chromosomes for chromosome Y are chromosome 3 and the group of chromosomes 2-6, respectively. The group of chromosomes 2-6 can be used as a first or second normalizing chromosome for chromosome Y, or as a normalizing chromosome for a first normalizing chromosome that is used for chromosome Y e.g. chromosome 3. In some embodiments, all chromosomes in the group of 2-6 are verified for the absence of aneuploidy. Two groups of chromosomes can be used as first and second normalizing chromosomes for chromosome 13, wherein the chromosomes of the first group are different from the chromosomes of the second group. As exemplified for chromosomes 13 and Y, a normalizing chromosome can be a chromosomes or a group of chromosomes.

In some embodiments, the methods may involve analysis of sequence tags for 3 or 4 normalizing chromosomes, in addition to the chromosome of interest.

Therefore, in some embodiments, the method determines the presence or absence of a fetal chromosomal aneuploidy in a maternal test sample comprising fetal and maternal nucleic acids by: (a) obtaining sequence information for the fetal and maternal nucleic acids in the maternal sample to identify a number of sequence tags for a chromosome of interest and a number of sequence tags for three normalizing chromosomes; (b) using the number of sequence tags to calculate first, second and third normalizing values for the chromosome of interest; and (c) comparing the first, second and third normalizing values for the chromosome of interest to one or more threshold values to determine the presence or absence of a fetal aneuploidy in the maternal sample. In some embodiments, the first normalizing value for the chromosome of interest is a first chromosome dose, which is a ratio of the number of sequence tags for the chromosome of interest and a first normalizing chromosome, and the second normalizing value for the chromosome of interest is a second chromosome dose, which is a ratio of the number of sequence tags for the chromosome of interest and a second normalizing chromosome, and the third normalizing value for the chromosome of interest is a third chromosome dose, which is a ratio of the number of sequence tags for the chromosome of interest and a third normalizing chromosome. Optionally, the first, second and third normalizing values can be expressed as normalized chromosome values (NCV) as described elsewhere herein.

Furthermore, in some embodiments, the method verifies the determination of the presence or absence of an aneuploidy of a chromosome of interest in a maternal test sample comprising fetal and maternal nucleic acid molecules by: (a) obtaining sequence information for the fetal and maternal nucleic acids in the maternal sample to identify a number of sequence tags for a chromosome of interest and a number of sequence tags for three normalizing chromosomes; (b) using the number of mapped tags for the chromosome of interest and the number of tags for a first normalizing chromosome to determine a first normalizing value for the chromosome of interest, (c) using the number of tags for the first normalizing chromosome and the number of tags for a second normalizing chromosome to determine a second normalizing value for the first normalizing chromosome; (d) using the number of tags for the second normalizing chromosome and the number of tags for a third normalizing chromosome to determine a third normalizing value for the second normalizing chromosome, and (e) comparing the first, second and third normalizing values for the chromosome of interest to one or more threshold values to determine the presence or absence of a fetal aneuploidy in the maternal sample. In some embodiments, the first normalizing value is a first chromosome dose, which is a ratio of the number of sequence tags for said chromosome of interest and a first normalizing chromosome, and the second normalizing value is a second chromosome dose, which is a ratio of the number of sequence tags for the first normalizing chromosome and a second normalizing chromosome, and the third normalizing value is a third chromosome dose, which is a ratio of the number of sequence tags for the second normalizing chromosome and a third normalizing chromosome. Optionally, the first, second and third normalizing values can be expressed as normalized chromosome values (NCV) as described elsewhere herein.

In some embodiments, the method determines the presence or absence of a fetal chromosomal aneuploidy in a maternal test sample comprising fetal and maternal nucleic acids by: (a) obtaining sequence information for the fetal and maternal nucleic acids in the maternal sample to identify a number of sequence tags for a chromosome of interest and a number of sequence tags for four normalizing chromosomes; (b) using the number of sequence tags to calculate first, second, third and fourth normalizing values for the chromosome of interest; and (c) comparing the first, second, third and fourth normalizing values for the chromosome of interest to one or more threshold values to determine the presence or absence of a fetal aneuploidy in the maternal sample. In some embodiments, the first normalizing value for the chromosome of interest is a first chromosome dose, which is a ratio of the number of sequence tags for the chromosome of interest and a first normalizing chromosome, and the second normalizing value for the chromosome of interest is a second chromosome dose, which is a ratio of the number of sequence tags for the chromosome of interest and a second normalizing chromosome, and the third normalizing value for the chromosome of interest is a third chromosome dose, which is a ratio of the number of sequence tags for the chromosome of interest and a third normalizing chromosome, and the fourth normalizing value for the chromosome of interest is a fourth chromosome dose, which is a ratio of the number of sequence tags for the chromosome of interest and a fourth normalizing chromosome. Optionally, the first, second, third and fourth normalizing values can be expressed as normalized chromosome values (NCV) as described elsewhere herein.

In some embodiments, the method determines and verifies the presence or absence of an aneuploidy of a chromosome of interest in a maternal test sample comprising fetal and maternal nucleic acid molecules by: (a) obtaining sequence information for the fetal and maternal nucleic acids in the maternal sample to identify a number of sequence tags for a chromosome of interest and a number of sequence tags for four normalizing chromosomes; (b) using the number of mapped tags for the chromosome of interest and the number of tags for a first normalizing chromosome to determine a first normalizing value for the chromosome of interest; (c) using the number of tags for the first normalizing chromosome and the number of tags for a second normalizing chromosome to determine a second normalizing value for the first normalizing chromosome; and (d) using the number of tags for the second normalizing chromosome and the number of tags for a third normalizing chromosome to determine a third normalizing value for the second normalizing chromosome; (e) using the number of tags for the third normalizing chromosome and the number of tags for a fourth normalizing chromosome to determine a fourth normalizing value for the third normalizing chromosome; and (f) comparing the first, second, third, and four the normalizing values for the chromosome of interest to one or more threshold values to determine the presence or absence of a fetal aneuploidy in the maternal sample. In some embodiments, the first normalizing value is a first chromosome dose, which is a ratio of the number of sequence tags for said chromosome of interest and a first normalizing chromosome, and the second normalizing value is a second chromosome dose, which is a ratio of the number of sequence tags for the first normalizing chromosome and a second normalizing chromosome, and the third normalizing value is a third chromosome dose, which is a ratio of the number of sequence tags for the second normalizing chromosome and a third normalizing chromosome, and the fourth normalizing value is a fourth chromosome dose, which is a ratio of the number of sequence tags for the third normalizing chromosome and a fourth normalizing chromosome. Optionally, the first, second, third and fourth normalizing values can be expressed as normalized chromosome values (NCV) as described elsewhere herein.

In these embodiments the first, second, third and fourth normalizing chromosomes can be selected from those set out above. For example, the first, second, third and fourth normalizing chromosomes for chromosome 1 can be selected from chromosomes 10, 11, 9 and 15; the first, second, third and fourth normalizing chromosomes for chromosome 2 can be selected from chromosomes 8, 7, 12, and 14; the first, second, third and fourth normalizing chromosomes for chromosome 3 can be selected from chromosomes 6, 5, 8, and 18; the first, second, third and fourth normalizing chromosomes for chromosome 4 can be selected from chromosomes 3, 5, 6, and 13; the first, second, third and fourth normalizing chromosomes for chromosome 5 can be selected from chromosomes 6, 3, 8, and 18; the first, second, third and fourth normalizing chromosomes for chromosome 6 can be selected from chromosomes 5, 3, 8, and 18. the first, second, third and fourth normalizing chromosomes for chromosome 7 can be selected from chromosomes 12, 2, 14 and 8; the first, second, third and fourth normalizing chromosomes for chromosome 8 can be selected from chromosomes 2, 7, 12, and 3 the first, second, third and fourth normalizing chromosomes for chromosome 9 can be selected from chromosomes 11, 10, 1, and 14; the first, second, third and fourth normalizing chromosomes for chromosome 10 can be selected from 1, 11, 9, and 15; the first, second, third and fourth normalizing chromosomes for chromosome 11 can be selected from chromosomes 1, 10, 9, and 15; the first, second, third and fourth normalizing chromosomes for chromosome 12 can be selected from chromosomes 7, 14, 2, and 8; the first, second, third and fourth normalizing chromosomes for chromosome 13 can be selected from chromosomes 4, group of chromosomes 2-6, 5, and 6; the first, second, third and fourth normalizing chromosomes for chromosome 14 can be selected from chromosomes 12, 7, 2, and 9; the first, second, third and fourth normalizing chromosomes for chromosome 15 can be selected from 1, 10, 11, and 9; the first, second, third and fourth normalizing chromosomes for chromosome 16 can be selected from chromosomes 20, 17, 15, and 1; the first, second, third and fourth normalizing chromosomes for chromosome 17 can be selected from chromosomes 16, 20, 19 and 22; the first, second, third and fourth normalizing chromosomes for chromosome 18 can be selected from chromosomes 8, 3, 2, and 6; the first, second, third and fourth normalizing chromosomes for chromosome 19 can be selected from chromosomes 22, 17, 16, and 20; the first, second, third and fourth normalizing chromosomes for chromosome 20 can be selected from chromosomes 16, 17, 15, and 1; the first, second, third and fourth normalizing chromosomes for chromosome 21 can be selected from chromosomes 9, 11, 14 and 1; the first, second, third and fourth normalizing chromosomes for chromosome 22 can be selected from chromosomes 19, 17, 16, and 20; the first, second, third and fourth normalizing chromosomes for chromosome X can be selected from chromosomes 6, 5, 13, and 3; and the first, second, third and fourth normalizing chromosomes for chromosome Y can be selected from group of chromosomes 2-6, chromosomes 3, 4, and 5.

Sequencing Methods

In some of the methods of the invention, obtaining sequence information for the fetal and maternal nucleic acids in the sample to identify a number of sequence tags comprises sequencing fetal and maternal nucleic acid molecules in the sample.

Sequence information is obtained by sequencing genomic DNA e.g. cell-free DNA in a maternal sample, using any one of the Next Generation Sequencing (NGS) methods in which clonally amplified DNA templates or single DNA molecules, are sequenced in a massively parallel fashion (e.g. as described in Volkerding et al. Clin Chem 55:641-658 [2009]; Metzker M Nature Rev 11:31-46 [2010]). In addition to high-throughput sequence information, NGS provides quantitative information, in that each sequence read is a countable "sequence tag" representing an individual clonal DNA template or a single DNA molecule. The sequencing technologies of NGS include without limitation pyrosequencing, sequencing-by-synthesis with reversible dye terminators, sequencing by oligonucleotide probe ligation and ion semiconductor sequencing. DNA from individual samples can be sequenced individually (i.e. singleplex sequencing) or DNA from multiple samples can be pooled and sequenced as indexed genomic molecules (i.e. multiplex sequencing) on a single sequencing run, to generate up to several hundred million reads of DNA sequences. Examples of sequencing technologies that can be used to obtain the sequence information according to the present method are described below.

Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include the SMRT™ technology of Pacific Biosciences, the Ion Torrent™ technology, and nanopore sequencing being developed for example, by Oxford Nanopore Technologies. While the automated Sanger method is considered as a 'first generation' technology, the present method can be applied to bioassays that use Sanger sequencing, including automated Sanger sequencing. In addition, the present method can be applied to bioassays that use nucleic acid imaging technologies e.g. atomic force microscopy (AFM) or transmission electron microscopy (TEM). Exemplary sequencing technologies are described below.

In one embodiment, the present method comprises obtaining sequence information for the genomic DNA e.g. fetal and maternal cfDNA, using single molecule sequencing technology the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes PCR-based amplification in the preparation of the sequencing libraries, and the directness of sample preparation allows for direct measurement of the sample, rather than measurement of copies of that sample.

In another embodiment, the present method comprises obtaining sequence information for the genomic DNA e.g. fetal and maternal cfDNA, using the 454 sequencing (Roche) (e.g. as described in Margulies, M. et al. Nature 437:376-380 [2005]). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed.

In another embodiment, the present method comprises obtaining sequence information for the genomic DNA e.g. fetal and maternal cfDNA, using the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another embodiment, the present method comprises obtaining sequence information for the genomic DNA e.g. fetal and maternal cfDNA using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength identifiers (ZMW identifiers) that obtain sequence information while phospholinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Identification of the corresponding fluorescence of the dye indicates which base was incorporated. The process is repeated.

In another embodiment, the present method comprises obtaining sequence information for the genomic DNA e.g. fetal and maternal cfDNA, using nanopore sequencing (e.g. as described in Soni G V and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In another embodiment, the present method comprises obtaining sequence information for the genomic DNA e.g. fetal and maternal cfDNA using the chemical-sensitive field effect transistor (chemFET) array (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the present method comprises obtaining sequence information for the genomic DNA e.g. fetal and maternal cfDNA using the Halcyon Molecular's technology, which uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be identified by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct identification allows recordation of nucleotide incorporation in seconds.

In another embodiment, the present method comprises obtaining sequence information for the genomic DNA e.g. fetal and maternal cfDNA by massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments of <300 bp, and maternal cfDNA has been estimated to circulate as fragments of between about 0.5 and 1 Kb (Li et al., Clin Chem, 50: 1002-1011 [2004]). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA e.g. cfDNA, is amplified using PCR before it is subjected to cluster amplification. Alternatively, an amplification-free genomic library preparation is used, and the randomly fragmented genomic DNA e.g. cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence identification is achieved using laser excitation and total internal reflection optics. Short sequence reads of about 20-40 bp e.g. 36 bp, are aligned against a repeat-masked reference genome and genetic differences are called using specially developed data analysis pipeline software. After completion of the first read, the templates can be regenerated in situ to enable a second read from the opposite end of the fragments. Thus, either single-end or paired end sequencing of the DNA fragments can be used. Partial sequencing of DNA fragments present in the sample is performed, and sequence tags comprising reads of predetermined length e.g. 36 bp, are mapped to a known reference genome. The mapped tags can be counted.

In one embodiment, the reference genome sequence is the NCBI36/hg18 sequence, which is available on the world wide web at the UCSC human genome browser. In another embodiment, the reference genome sequence is the GRCh37/hg19, which is available on the world wide web at the UCSC human genome browser. The sequences of other reference genomes from a variety of species are available on the world wide web at the NCBI website. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software.

In some embodiments of the method described herein, the mapped sequence tags comprise sequence reads of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence tags comprise sequence reads that are 36 bp. Mapping of the sequence tags is achieved by comparing the sequence of the tag with the sequence of the reference to determine the chromosomal origin of the sequenced nucleic acid (e.g. cfDNA) molecule, and specific genetic sequence information is not needed. A small degree of mismatch (0-2 mismatches per sequence tag) may be allowed to account for minor polymorphisms that may exist between the reference genome and the genomes in the mixed sample.

A plurality of sequence tags are obtained per sample. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between 20 and 40 bp reads e.g. 36 bp, are obtained from mapping the reads to the reference genome per sample. In one embodiment, all the sequence reads are mapped to all regions of the reference genome. In one embodiment, the tags that have been mapped to all regions e.g. all chromosomes, of the reference genome are counted, and the CNV i.e. the over- or under-representation of a sequence of interest e.g. a chromosome or portion thereof, in the mixed DNA sample is determined. The method does not require differentiation between the two genomes.

In some embodiments, the method determines the presence or absence of a fetal chromosomal aneuploidy in a maternal test sample comprising fetal and maternal nucleic acid molecules by (a) obtaining sequence information for the fetal and maternal nucleic acids in the maternal sample to identify a number of sequence tags for a chromosome of interest and a number of sequence tags for at least two normalizing chromosomes, wherein the sequence information comprises next generation sequencing (NGS); comprises sequencing-by-synthesis using reversible dye terminators; comprises sequencing-by-ligation; or comprises single molecule sequencing; (b) using the number of sequence tags to calculate a first and a second normalizing value for the chromosome of interest; and (c) comparing the first normalizing value for the chromosome of interest to a first threshold value and comparing the second normalizing value for the chromosome of interest to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said chromosome of interest to a threshold value verifies the determination of the presence or absence of an aneuploidy for the chromosome of interest. In some embodiments, the first normalizing value is a first chromosome dose, which is a ratio of the number of sequence tags for the chromosome of interest and a first normalizing chromosome, and the second normalizing value is a second chromosome dose, which is a ratio of the number of sequence tags for the chromosome of interest and a second normalizing chromosome. Optionally, the first and second normalizing values can be expressed as normalized chromosome values (NCV) as described herein.

In some other embodiments, the method verifies the determination of the presence or absence of an aneuploidy of a chromosome of interest in a maternal test sample comprising fetal and maternal nucleic acid molecules by: (a) obtaining sequence information for the fetal and maternal nucleic acids in the sample to identify a number of mapped sequence tags for a chromosome of interest and a number of sequence tags for at least two normalizing chromosomes, wherein obtaining the sequence information comprises next generation sequencing (NGS); comprises sequencing-by-synthesis using reversible dye terminators; comprises sequencing-by-ligation; or comprises single molecule sequencing; (b) using the number of tags for the chromosome of interest and the number of tags for a first normalizing chromosome to determine a first normalizing value for the chromosome of interest, and using the number of sequence tags for the first normalizing chromosome and the number of sequence tags for a second normalizing chromosome to determine a second normalizing value for the first normalizing chromosome; and (c) comparing the first normalizing value for the chromosome of interest to a first threshold value and comparing the second normalizing value for the first normalizing chromosome to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said first normalizing chromosome to a threshold value verifies the determination of the presence or absence of an aneuploidy for the chromosome of interest. In some embodiments, the first normalizing value is a first chromosome dose, which is a ratio of the number of sequence tags for said chromosome of interest and a first normalizing chromosome, and the second normalizing value a second chromosome dose, which is a ratio of the number of sequence tags for the first normalizing chromosome and a second normalizing chromosome. Optionally, the first and second normalizing values can be expressed as normalized chromosome values (NCV) calculated as described herein.

In some embodiments, the first normalizing value is a first chromosome dose, which is a ratio of the number of sequence tags for said chromosome of interest and a first normalizing chromosome, and the second normalizing value a second chromosome dose, which is a ratio of the number of sequence tags for the first normalizing chromosome and a second normalizing chromosome. Optionally, the first and second normalizing values can be expressed as normalized chromosome values (NCV) as described herein.

Samples

The sample comprising the mixture of nucleic acids to which the methods described herein are applied is a biological sample such as a tissue sample, a biological fluid sample, or a cell sample. In some embodiments, the mixture of nucleic acids is purified or isolated from the biological sample by any one of the known methods. A sample can consist of purified or isolated polynucleotide, or it can comprise a biological sample such as a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, amniotic fluid, and leukophoresis samples. In some embodiments, the sample is a sample that is easily obtainable by non-invasive procedures e.g. blood, plasma, serum, sweat, tears, sputum, urine, sputum, ear flow, and saliva. Preferably, the biological sample is a peripheral blood sample, or the plasma and serum fractions. In other embodiments, the biological sample is a swab or smear, a biopsy specimen, or a cell culture. In another embodiment, the sample is a mixture of two or more biological samples e.g. a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In some embodiments, samples can be obtained from sources, including, but not limited to, samples from different individuals, different developmental stages of the same or different individuals, different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, or individuals with predisposition to a pathology, or individuals with exposure to an infectious disease agent (e.g., HIV), and individuals who are recipients of donor cells, tissues and/or organs. In some embodiments, the sample is a sample comprising a mixture of different source samples derived from the same or different subjects. For example, a sample can comprise a mixture of cells derived from two or more individuals, as is often found at crime scenes. In one embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples. In some embodiments, the sample is a sample that is easily obtainable by non-invasive procedures e.g. blood, plasma, serum, sweat, tears, sputum, urine, sputum, ear flow, and saliva. In some embodiments, the biological sample is a peripheral blood sample, or the plasma and serum fractions. In other embodiments, the biological sample is a swab or smear, a biopsy specimen, or a cell culture. In another embodiment, the maternal sample is a mixture of two or more biological samples e.g. a biological sample can comprise two or more of a biological fluid sample, a tissue sample, and a cell culture sample. As disclosed above, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

Samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue or cells.

Methods of isolating nucleic acids from biological sources are well known and will differ depending upon the nature of the source. One of skill in the art can readily isolate nucleic acid from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation. In other embodiments, the sample nucleic acids are obtained as genomic DNA, which is subjected to fragmentation into fragments of approximately 500 or more base pairs, and to which NGS methods can be readily applied.

Samples that are used for determining a CNV e.g. chromosomal and partial aneuploidies, comprise genomic nucleic acids that are present in cells i.e. cellular, or that are "cell-free". Genomic nucleic acids include DNA and RNA. Preferably, genomic nucleic acids are cellular and/or cfDNA. In some embodiments, the genomic nucleic acid of the sample is cellular DNA, which can be derived from whole cells by manually or mechanically extracting the genomic DNA from whole cells of the same or of differing genetic compositions. Cellular DNA can be derived for example, from whole cells of the same genetic composition derived from one subject, from a mixture of whole cells of different subjects, or from a mixture of whole cells that differ in genetic composition that are derived from one subject. Methods for extracting genomic DNA from whole cells are known in the art, and differ depending upon the nature of the source. In some embodiments, it can be advantageous to fragment the cellular genomic DNA. Fragmentation can be random, or it can be specific, as achieved, for example, using restriction endonuclease digestion. Methods for random fragmentation are well known in the art, and include, for example, limited DNAse digestion, alkali treatment, and physical shearing. In some embodiments, sample nucleic acids are obtained as cellular genomic DNA, which is subjected to fragmentation into fragments of approximately 500 or more base pairs, which can be sequenced by next generation sequencing (NGS).

In some embodiments, cellular genomic DNA is obtained to identify chromosomal aneuploidies of a sample comprising a single genome. For example, cellular genomic DNA can be obtained from a sample that contains only cells of a pregnant female i.e. the sample is free of fetal genomic sequences. Identification of chromosomal aneuploidies from a single genome e.g. maternal only genome, can be used in a comparison with chromosomal aneuploidies and/or polymorphisms identified in a mixture of fetal and maternal genomes present in maternal plasma to identify the fetal chromosomal aneuploidies. Similarly, cellular genomic DNA can be obtained from a patient e.g. a cancer patient, at different stages of treatment to assess the efficacy of the therapeutic regimen by analyzing possible changes in chromosomal aneuploidies and/or polymorphisms in the sample DNA In some embodiments, it is advantageous to obtain cell-free nucleic acids e.g. cell-free DNA (cfDNA). Cell-free nucleic acids, including cell-free DNA, can be obtained by various methods known in the art from biological samples including but not limited to plasma, serum and urine (Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J. Mol. Diagn. 6: 101-107 [2004]). To separate cfDNA from cells, fractionation, centrifugation (e.g., density gradient centrifugation), DNA-specific precipitation, or high-throughput cell sorting and/or separation methods can be used. Commercially available kits for manual and automated separation of cfDNA are available (Roche Diagnostics, Indianapolis, Ind., Qiagen, Valencia, Calif., Macherey-Nagel, Duren, Del.). Biological samples comprising cfDNA have been used in assays to determine the presence or absence of chromosomal abnormalities e.g. trisomy 21, by sequencing assays that can determine chromosomal aneuploidies and/or various polymorphisms.

The cfDNA present in the sample can be enriched specifically or non-specifically prior to preparing a sequencing library. Non-specific enrichment of sample DNA refers to the whole genome amplification of the genomic DNA fragments of the sample that can be used to increase the level of the sample DNA prior to preparing a cfDNA sequencing library. Non-specific enrichment can be the selective enrichment of one of the two genomes present in a sample that comprises more than one genome. For example, non-specific enrichment can be selective of the fetal genome in a maternal sample, which can be obtained by known methods to increase the relative proportion of fetal to maternal DNA in a sample. Alternatively, non-specific enrichment can be the non-selective amplification of both genomes present in the sample. For example, non-specific amplification can be of fetal and maternal DNA in a sample comprising a mixture of DNA from the fetal and maternal genomes. Methods for whole genome amplification are known in the art. Degenerate oligonucleotide-primed PCR (DOP), primer extension PCR technique (PEP) and multiple displacement amplification (MDA), are examples of whole genome amplification methods. In some embodiments, the sample comprising the mixture of cfDNA from different genomes is unenriched for cfDNA of the genomes present in the mixture. In other embodiments, the sample comprising the mixture of cfDNA from different genomes is non-specifically enriched for any one of the genomes present in the sample.

Applications

Cell-free fetal DNA and RNA circulating in maternal blood can be used for the early non-invasive prenatal diagnosis (NIPD) of an increasing number of genetic conditions, both for pregnancy management and to aid reproductive decision-making. The presence of cell-free DNA circulating in the bloodstream has been known for over 50 years. More recently, presence of small amounts of circulating fetal DNA was discovered in the maternal bloodstream during pregnancy (Lo et al., Lancet 350:485-487 [1997]). Thought to originate from dying placental cells, cell-free fetal DNA (cfDNA) has been shown to consists of short fragments typically fewer than 200 bp in length Chan et al., Clin Chem 50:88-92 [2004]), which can be discerned as early as 4 weeks gestation (Blanes et al., Early Human Dev 83:563-566 [2007]), and known to be cleared from the maternal circulation within hours of delivery (Lo et al., Am J Hum Genet 64:218-224 [1999]). In addition to cfDNA, fragments of cell-free fetal RNA (cfRNA) can also be discerned in the maternal bloodstream, originating from genes that are transcribed in the fetus or placenta. The extraction and subsequent analysis of these fetal genetic elements from a maternal blood sample offers novel opportunities for NIPD.

The method can be used to determine the presence or absence of a fetal chromosomal aneuploidy in a maternal sample comprising fetal and maternal nucleic acid molecules e.g. cfDNA. The present method is a polymorphism-independent method for use in NIPD and does not require that the fetal cfDNA be distinguished from the maternal cfDNA to enable the determination of a fetal aneuploidy.

In some embodiments, the sample is a biological fluid sample e.g. a blood sample or fractions thereof. Preferably, the biological sample is selected from plasma, serum and urine. In some embodiments, the maternal source sample is a peripheral blood sample. In other embodiments, the maternal source sample is a plasma sample. Sequencing of fetal and maternal nucleic acids can be achieved by any one of the massively parallel NGS sequencing methods. In one embodiment, sequencing is massively parallel sequencing is of clonally amplified cfDNA molecules or of single cfDNA molecules. In another embodiment, sequencing is said massively parallel sequencing is massively parallel sequencing-by-synthesis with reversible dye terminators. In another embodiment, sequencing is massively parallel sequencing is performed using massively parallel sequencing-by-ligation.

In some embodiments, the method can determine or verify the presence or absence of at least two different chromosomal aneuploidies. In one embodiment, the method determines the presence or absence of at least two different fetal chromosomal aneuploidies by repeating the steps (a)-(c) for at least two chromosomes of interest, wherein the steps comprise (a) obtaining sequence information for the fetal and maternal nucleic acids in the maternal sample to identify a number of sequence tags for a chromosome of interest and a number of sequence tags for at least two normalizing chromosomes; (b) using the number of sequence tags to calculate a first and a second normalizing value for the chromosome of interest; and (c) comparing the first normalizing value for the chromosome of interest to a first threshold value and comparing the second normalizing value for the chromosome of interest to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said chromosome of interest to a threshold value verifies the determination of the presence or absence of an aneuploidy for the chromosome of interest. In some embodiments, the first normalizing value is a first chromosome dose, which is a ratio of the number of sequence tags for the chromosome of interest and a first normalizing chromosome, and the second normalizing value is a second chromosome dose, which is a ratio of the number of sequence tags for the chromosome of interest and a second normalizing chromosome. Optionally, the first and second normalizing values can be expressed as normalized chromosome values (NCV) as described herein.

Alternatively, the method determines the presence or absence of at least two different fetal chromosomal aneuploidies by repeating the steps (a)-(c) for at least two chromosomes of interest, wherein the steps comprise (a) obtaining sequence information for the fetal and maternal nucleic acids in the sample to identify a number of mapped sequence tags for a chromosome of interest and a number of sequence tags for at least two normalizing chromosomes; (b) using the number of tags for the chromosome of interest and the number of tags for a first normalizing chromosome to determine a first normalizing value for the chromosome of interest, and using the number of sequence tags for the first normalizing chromosome and the number of sequence tags for a second normalizing chromosome to determine a second normalizing value for the first normalizing chromosome; and (c) comparing the first normalizing value for the chromosome of interest to a first threshold value and comparing the second normalizing value for the first normalizing chromosome to a second threshold value to determine the presence or absence of a fetal aneuploidy in the sample. The first and second threshold values can be the same or they can be different. In step (c) of this method, the comparison of the first normalizing value for said chromosome of interest to a threshold value indicates the presence or absence of an aneuploidy for said chromosome of interest, and the comparison of the second normalizing value for said first normalizing chromosome to a threshold value verifies the determination of the presence or absence of an aneuploidy for the chromosome of interest. In some embodiments, the first normalizing value is a first chromosome dose, which is a ratio of the number of sequence tags for said chromosome of interest and a first normalizing chromosome, and the second normalizing value a second chromosome dose, which is a ratio of the number of sequence tags for the first normalizing chromosome and a second normalizing chromosome. Optionally, the first and second normalizing values can be expressed as normalized chromosome values (NCV) as described herein.

In these embodiments, the method can be repeated for all chromosomes to determine the presence or absence of a fetal chromosomal aneuploidy.

Examples of one or at least two different chromosomal aneuploidies that can be determined include T21, T13, T18, T2, T9, and monosomy X. In some embodiments, the maternal sample is obtained from a pregnant woman. In some embodiments, the maternal sample is a biological fluid sample e.g. a blood sample or the plasma fraction derived therefrom. In some embodiments, the maternal sample is a plasma sample. In some embodiments, the nucleic acids in the maternal sample are cfDNA molecules.

Examples of fetal chromosomal aneuploidies include without limitation complete chromosomal trisomies or monosomies, or partial trisomies or monosomies. Examples of complete fetal trisomies include trisomy 21 (T21; Down Syndrome), trisomy 18 (T18; Edward's Syndrome), trisomy 16 (T16), trisomy 22 (T22; Cat Eye Syndrome), trisomy 15 (T15), trisomy 13 (T13; Patau Syndrome), trisomy 8 (T8; Warkany Syndrome), trisomy 9 (T9), trisomy 2, and the XXY (Kleinefelter Syndrome), XYY, or XXX trisomies. Examples of partial trisomies include 1q32-44, trisomy 9 p with trisomy, trisomy 4 mosaicism, trisomy 17p, partial trisomy 4q26-qter, trisomy 9, partial 2p trisomy, partial trisomy 1q, and/or partial trisomy 6p/monosomy 6q. Examples of fetal monosomies include chromosomal monosomy X, and partial monosomies of chromosome 13, chromosome 15, chromosome 16, chromosome 18, chromosome 21, and chromosome 22, which are known to be involved in pregnancy miscarriage. Partial monosomy of chromosomes typically involved in complete aneuploidy can also be determined by the method of the invention. Monosomy 18p is a rare chromosomal disorder in which all or part of the short arm (p) of chromosome 18 is deleted (monosomic). The disorder is typically characterized by short stature, variable degrees of mental retardation, speech delays, malformations of the skull and facial (craniofacial) region, and/or additional physical abnormalities. Associated craniofacial defects may vary greatly in range and severity from case to case. Conditions caused by changes in the structure or number of copies of chromosome 15 include Angelman Syndrome and Prader-Willi Syndrome, which involve a loss of gene activity in the same part of chromosome 15, the 15q11-q13 region. It will be appreciated that several translocations and microdeletions can be asymptomatic in the carrier parent, yet can cause a major genetic disease in the offspring. For example, a healthy mother who carries the 15q11-q13 microdeletion can give birth to a child with Angelman syndrome, a severe neurodegenerative disorder. Thus, the present invention can be used to identify such a deletion in the fetus. Partial monosomy 13q is a rare chromosomal disorder that results when a piece of the long arm (q) of chromosome 13 is missing (monosomic). Infants born with partial monosomy 13q may exhibit low birth weight, malformations of the head and face (craniofacial region), skeletal abnormalities (especially of the hands and feet), and other physical abnormalities. Mental retardation is characteristic of this condition. The mortality rate during infancy is high among individuals born with this disorder. Almost all cases of partial monosomy 13q occur randomly for no apparent reason (sporadic). 22q11.2 deletion syndrome, also known as DiGeorge syndrome, is a syndrome caused by the deletion of a small piece of chromosome 22. The deletion (22 q11.2) occurs near the middle of the chromosome on the long arm of one of the pair of chromosome. The features of this syndrome vary widely, even among members of the same family, and affect many parts of the body. Characteristic signs and symptoms may include birth defects such as congenital heart disease, defects in the palate, most commonly related to neuromuscular problems with closure (velo-pharyngeal insufficiency), learning disabilities, mild differences in facial features, and recurrent infections. Microdeletions in chromosomal region 22q11.2 are associated with a 20 to 30-fold increased risk of schizophrenia. In one embodiment, the method of the invention is used to determine partial monosomies including but not limited to monosomy 18p, partial monosomy of chromosome 15 (15q11-q13), partial monosomy 13q, and partial monosomy of chromosome 22 can also be determined using the method.

In some embodiments, the chromosomal aneuploidy is a complete chromosomal aneuploidy that occurs in a mosaic state. For example, in some embodiments, the chromosomal aneuploidy is an aneuploidy occurring as a true chromosomal mosaicism, wherein the fetal cells can comprise two different karyotypes. In other embodiments, the chromosomal aneuploidy is associated with a mosaicism confined predominantly to the placental tissues. Confined placental mosaicism (CPM) represents a discrepancy between the chromosomal makeup of the cells in the placenta and the cells in the baby. Most commonly when CPM is found it represents a trisomic cell line in the placenta and a normal diploid chromosome complement in the baby. However, the fetus is involved in about 10% of cases. It is thought that the presence of significant numbers of abnormal cells in the placenta interferes with proper placental function. An impaired placenta cannot support the pregnancy and this may lead to the loss of a chromosomally normal baby (Tyson & Kalousek, 1992). For many of the autosomal trisomies, only mosaic cases survive to term. For example, complete trisomy 2 contributes significantly to first trimester pregnancy losses, occurring in 0.16% of clinically recognized pregnancies. Trisomy 2 seems to only be compatible with life in a mosaic state and if the trisomy is confined predominantly to placental tissues. Mosaic trisomy 2 presents one of the more difficult counseling situations despite that a number of cases of prenatally determined trisomy 2 mosaicism have been identified. Outcome ranges from normal to neonatal death. Oligohydramnios (low amniotic fluid) and poor intrauterine growth were the most common features. Abnormal outcome is probably predominantly a consequence of high levels of trisomy in the placenta as well as possible presence of low level trisomy in the baby itself. Some uncommon trisomies e.g. trisomy 9, can occur in a mosaic or non-mosaic state and present with a distinct clinical picture. The finding of mosaic trisomy 9 on chorionic villus sampling presents a difficult counseling situation. Diagnosis of trisomy 9 on CVS should be followed up with amniocentesis and serial ultrasound to exclude trisomy in the fetus, which result in symptoms including dysmorphisms in the skull, nervous system, and mental retardation. Dysmorphisms in the heart, kidneys, and musculoskeletal system may also occur. In most cases where trisomy is found on CVS but not on amniocentesis, the outcome is normal. However, an abnormal outcome can also occur. Despite that a number of cases of prenatally determined trisomy 9 mosaicism have been identified, outcome ranges from normal to neonatal death. Some trisomies are rare and lethal, while others are viable if confined to the placental cells. In the latter cases determination of a trisomy, can be followed up with additional test e.g. amniocentesis, to rule out that the trisomy is a fetal trisomy.

The present method is also applicable for determining any chromosomal abnormality if one of the parents is a known carrier of such abnormality. These include, but not limited to, mosaic for a small supernumerary marker chromosome (SMC); t(11;14)(p15;p13) translocation; unbalanced translocation t(8;11)(p23.2;p15.5); 11q23 microdeletion; Smith-Magenis syndrome 17p11.2 deletion; 22q13.3 deletion; Xp22.3 microdeletion; 10p14 deletion; 20p microdeletion, DiGeorge syndrome [del(22)(q11.2q11.23)], Williams syndrome (7q11.23 and 7q36 deletions); 1p36 deletion; 2p microdeletion; neurofibromatosis type 1 (17q11.2 microdeletion), Yq deletion; Wolf-Hirschhorn syndrome (WHS, 4p16.3 microdeletion); 1p36.2 microdeletion; 11q14 deletion; 19q13.2 microdeletion; Rubinstein-Taybi (16 p13.3 microdeletion); 7p21 microdeletion; Miller-Dieker syndrome (17p13.3), 17p11.2 deletion; and 2q37 microdeletion.

The method can also be combined with assays for determining other prenatal conditions associated with the mother and/or the fetus. The method is also applicable to determining copy number variations (CNV) of any sequence of interest in samples comprising mixtures of genomic nucleic acids derived from at least two different genomes and which are known or are suspected to differ in the amount of one or more sequence of interest. In some embodiments, the method can be used to determine the presence or absence of a chromosomal aneuploidy in pregnancies with twin fetuses (see Example 1). In pregnancies with non-identical twins, the method can determine the presence or absence of a chromosomal aneuploidy in a twin pregnancy, and determine whether one or both twin fetuses carry the aneuploidy by establishing a fetal fraction for each of the twins and comparing it to the fetal fraction associated with the aneuploidy. A first and a second fetal fraction can be determined for the first and second twin, respectively, by sequencing polymorphic sequences e.g. SNPs in the maternal plasma cfDNA. Each fetal fraction can be calculated as the ratio of the portion of the major allele contributed by the mother and the portion of the minor allele contributed by the fetus. Methods for determining fetal fraction in maternal plasma cfDNA are described in pending U.S. patent application Ser. Nos. 12/958,347 entitled "Methods for Determining Fraction of Fetal Nucleic Acids in Maternal Samples", 12/958,356 entitled "Simultaneous determination of Aneuploidy and Fetal Fraction" both filed on Dec. 1, 2010, and 13/009,718 entitled "Identification of polymorphic sequences in mixtures of genomic DNA by whole genome sequencing" filed Jan. 19, 2011, which are incorporated herein by reference in their entirety). As the non-identical twins will differ at least at some of the SNP sites, two separate fetal fractions (first and second) can be determined. Given the NCV for chromosome 21 for the sample with the twin pregnancy, a fetal fraction associated with the aneuploidy can be estimated as a percent of the difference between the chromosome dose for the aneuploid twin sample and the average of the chromosome 21 dose in the qualified samples of the training set i.e. NCV chromosome 21 dose in test sample-NCV average chromosome 21 dose in qualified samples/NCV chromosome 21 dose in test sample. The fraction associated with the aneuploidy and calculated suing the NCV for chromosome 21, will correspond to one the first or second fetal fractions that were determined using differences in SNP sequences, thereby identifying whether one or both twins carry the aneuploidy.

In addition to the applicability of the method for determining chromosomal aneuploidies indicative of a genetic condition in a fetus, the method can be applied determinations of the presence or absence of chromosomal abnormalities indicative of a disease e.g. cancer, and/or the status of a disease, determinations of the presence or absence of nucleic acids of a pathogen e.g. virus, determination of chromosomal abnormalities associated with graft versus host disease (GVHD), and determinations of the contribution of individuals in forensic analyses.

CNV in the human genome significantly influence human diversity and predisposition to disease (Redon et al., Nature 23:444-454 [2006], Shaikh et al. Genome Res 19:1682-1690 [2009]). CNVs have been known to contribute to genetic disease through different mechanisms, resulting in either imbalance of gene dosage or gene disruption in most cases. In addition to their direct correlation with genetic disorders, CNVs are known to mediate phenotypic changes that can be deleterious. Recently, several studies have reported an increased burden of rare or de novo CNVs in complex disorders such as Autism, ADHD, and schizophrenia as compared to normal controls, highlighting the potential pathogenicity of rare or unique CNVs (Sebat et al., 316:445-449 [2007]; Walsh et al., Science 320:539-543 [2008]). CNV arise from genomic rearrangements, primarily owing to deletion, duplication, insertion, and unbalanced translocation events.

Embodiments of the invention provide for a method to assess copy number variation of a sequence of interest e.g. a clinically-relevant sequence, in a test sample that comprises a mixture of nucleic acids derived from two different genomes, and which are known or are suspected to differ in the amount of one or more sequence of interest. The mixture of nucleic acids is derived from two or more types of cells. In one embodiment, the mixture of nucleic acids is derived from normal and cancerous cells derived from a subject suffering from a medical condition e.g. cancer.

It is believed that many solid tumors, such as breast cancer, progress from initiation to metastasis through the accumulation of several genetic aberrations. [Sato et al., Cancer Res., 50: 7184-7189 [1990]; Jongsma et al., J Clin PAthol: Mol Path 55:305-309 [2002])]. Such genetic aberrations, as they accumulate, may confer proliferative advantages, genetic instability and the attendant ability to evolve drug resistance rapidly, and enhanced angiogenesis, proteolysis and metastasis. The genetic aberrations may affect either recessive "tumor suppressor genes" or dominantly acting oncogenes. Deletions and recombination leading to loss of heterozygosity (LOH) are believed to play a major role in tumor progression by uncovering mutated tumor suppressor alleles.

cfDNA has been found in the circulation of patients diagnosed with malignancies including but not limited to lung cancer (Pathak et al. Clin Chem 52:1833-1842 [2006]), prostate cancer (Schwartzenbach et al. Clin Cancer Res 15:1032-8 [2009]), and breast cancer (Schwartzenbach et al. available online at breast-cancer-research.com/content/11/5/R71 [2009]). Identification of genomic instabilities associated with cancers that can be determined in the circulating cfDNA in cancer patients is a potential diagnostic and prognostic tool. In one embodiment, the method of the invention assesses CNV of a sequence of interest in a sample comprising a mixture of nucleic acids derived from a subject that is suspected or is known to have cancer e.g. carcinoma, sarcoma, lymphoma, leukemia, germ cell tumors and blastoma. In one embodiment, the sample is a plasma sample derived (processes) from peripheral blood and that comprises a mixture of cfDNA derived from normal and cancerous cells. In another embodiment, the biological sample that is needed to determine whether a CNV is present is derived from a mixture of cancerous and non-cancerous cells from other biological fluids including but not limited to serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples, or in tissue biopsies, swabs or smears.

The sequence of interest is a nucleic acid sequence that is known or is suspected to play a role in the development and/or progression of the cancer. Examples of a sequence of interest include nucleic acids sequences that are amplified or deleted in cancerous cells as described in the following.

Dominantly acting genes associated with human solid tumors typically exert their effect by overexpression or altered expression. Gene amplification is a common mechanism leading to upregulation of gene expression. Evidence from cytogenetic studies indicates that significant amplification occurs in over 50% of human breast cancers. Most notably, the amplification of the proto-oncogene human epidermal growth factor receptor 2 (HER2) located on chromosome 17 (17(17q21-q22)), results in overexpression of HER2 receptors on the cell surface leading to excessive and dysregulated signaling in breast cancer and other malignancies (Park et al., Clinical Breast Cancer 8:392-401 [2008]). A variety of oncogenes have been found to be amplified in other human malignancies. Examples of the amplification of cellular oncogenes in human tumors include amplifications of: c-myc in promyelocytic leukemia cell line HL60, and in small-cell lung carcinoma cell lines, N-myc in primary neuroblastomas (stages III and IV), neuroblastoma cell lines, retinoblastoma cell line and primary tumors, and small-cell lung carcinoma lines and tumors, L-myc in small-cell lung carcinoma cell lines and tumors, c-myb in acute myeloid leukemia and in colon carcinoma cell lines, c-erbb in epidermoid carcinoma cell, and primary gliomas, c-K-ras-2 in primary carcinomas of lung, colon, bladder, and rectum, N-ras in mammary carcinoma cell line (Varmus H., Ann Rev Genetics 18: 553-612 (1984) [cited in Watson et al., Molecular Biology of the Gene (4th ed.; Benjamin/Cummings Publishing Co. 1987)].

Chromosomal deletions involving tumor suppressor genes may play an important role in the development and progression of solid tumors. The retinoblastoma tumor suppressor gene (Rb-1), located in chromosome 13q14, is the most extensively characterized tumor suppressor gene. The Rb-1 gene product, a 105 kDa nuclear phosphoprotein, apparently plays an important role in cell cycle regulation (Howe et al., Proc Natl Acad Sci (USA) 87:5883-5887 [1990]). Altered or lost expression of the Rb protein is caused by inactivation of both gene alleles either through a point mutation or a chromosomal deletion. Rb-i gene alterations have been found to be present not only in retinoblastomas but also in other malignancies such as osteosarcomas, small cell lung cancer (Rygaard et al., Cancer Res 50: 5312-5317 [1990])) and breast cancer. Restriction fragment length polymorphism (RFLP) studies have indicated that such tumor types have frequently lost heterozygosity at 13q suggesting that one of the Rb-1 gene alleles has been lost due to a gross chromosomal deletion (Bowcock et al., Am J Hum Genet, 46: 12 [1990]). Chromosome 1 abnormalities including duplications, deletions and unbalanced translocations involving chromosome 6 and other partner chromosomes indicate that regions of chromosome 1, in particular 1q21-1q32 and 1p11-13, might harbor oncogenes or tumor suppressor genes that are pathogenetically relevant to both chronic and advanced phases of myeloproliferative neoplasms (Caramazza et al., Eur J Hematol 84:191-200 [2010]). Myeloproliferative neoplasms are also associated with deletions of chromosome 5. Complete loss or interstitial deletions of chromosome 5 are the most common karyotypic abnormality in myelodysplastic syndromes (MDSs). Isolated del(5q)/5q-MDS patients have a more favorable prognosis than those with additional karyotypic defects, who tend to develop myeloproliferative neoplasms (MPNs) and acute myeloid leukemia. The frequency of unbalanced chromosome 5 deletions has led to the idea that 5q harbors one or more tumor-suppressor genes that have fundamental roles in the growth control of hematopoietic stem/progenitor cells (HSCs/HPCs). Cytogenetic mapping of commonly deleted regions (CDRs) centered on 5q31 and 5q32 identified candidate tumor-suppressor genes, including the ribosomal subunit RPS14, the transcription factor Egr1/Krox20 and the cytoskeletal remodeling protein, alpha-catenin (Eisenmann et al., Oncogene 28:3429-3441 [2009]). Cytogenetic and allelotyping studies of fresh tumours and tumour cell lines have shown that allelic loss from several distinct regions on chromosome 3p, including 3p25, 3p21-22, 3p21.3, 3p12-13 and 3p14, are the earliest and most frequent genomic abnormalities involved in a wide spectrum of major epithelial cancers of lung, breast, kidney, head and neck, ovary, cervix, colon, pancreas, esophagous, bladder and other organs. Several tumor suppressor genes have been mapped to the chromosome 3p region, and are thought that interstitial deletions or promoter hypermethylation precede the loss of the 3p or the entire chromosome 3 in the development of carcinomas (Angeloni D., Briefings Functional Genomics 6:19-39 [2007]).

Newborns and children with Down syndrome (DS) often present with congenital transient leukemia and have an increased risk of acute myeloid leukemia and acute lymphoblastic leukemia. Chromosome 21, harboring about 300 genes, may be involved in numerous structural aberrations, e.g., translocations, deletions, and amplifications, in leukemias, lymphomas, and solid tumors. Moreover, genes located on chromosome 21 have been identified that play an important role in tumorigenesis. Somatic numerical as well as structural chromosome 21 aberrations are associated with leukemias, and specific genes including RUNX1, TMPRSS2, and TFF, which are located in 21q, play a role in tumorigenesis (Fonatsch C Gene Chromosomes Cancer 49:497-508 [2010]).

In one embodiment, the method provides a means to assess the association between gene amplification and the extent of tumor evolution. Correlation between amplification and/or deletion and stage or grade of a cancer may be prognostically important because such information may contribute to the definition of a genetically based tumor grade that would better predict the future course of disease with more advanced tumors having the worst prognosis. In addition, information about early amplification and/or deletion events may be useful in associating those events as predictors of subsequent disease progression. Gene amplification and deletions as identified by the method can be associated with other known parameters such as tumor grade, histology, Brd/Urd labeling index, hormonal status, nodal involvement, tumor size, survival duration and other tumor properties available from epidemiological and biostatistical studies. For example, tumor DNA to be tested by the method could include atypical hyperplasia, ductal carcinoma in situ, stage I-III cancer and metastatic lymph nodes in order to permit the identification of associations between amplifications and deletions and stage. The associations made may make possible effective therapeutic intervention. For example, consistently amplified regions may contain an overexpressed gene, the product of which may be able to be attacked therapeutically (for example, the growth factor receptor tyrosine kinase, p185$^{HER2}$).

The method can be used to identify amplification and/or deletion events that are associated with drug resistance by determining the copy number variation of nucleic acids from primary cancers to those of cells that have metastasized to other sites." If gene amplification and/or deletion is a manifestation of karyotypic instability that allows rapid development of drug resistance, more amplification and/or deletion in primary tumors from chemoresistant patients than in tumors in chemosensitive patients would be expected. For example, if amplification of specific genes is responsible for the development of drug resistance, regions surrounding those genes would be expected to be amplified consistently in tumor cells from pleural effusions of chemoresistant patients but not in the primary tumors. Discovery of associations between gene amplification and/or deletion and the development of drug resistance may allow the identification of patients that will or will not benefit from adjuvant therapy.

Apparatus and Systems for Determining CNV

Analysis of the sequencing data and the determination derived therefrom are typically performed using various computer hardware, computer algorithms and computer programs. The methods of the invention are therefore typically computer-implemented or computer-assisted methods.

In one embodiment, the invention provides a computer program product for generating an output indicating the presence or absence of a fetal aneuploidy in a test sample. The computer product comprises a computer readable medium having a computer executable logic recorded thereon for enabling a processor to determine the presence or absence of a fetal aneuploidy comprising: a receiving procedure for receiving sequencing data from at least a portion of nucleic acid molecules from a maternal biological sample, wherein said sequencing data comprises sequence reads; computer assisted logic for analyzing a fetal aneuploidy from said received data; and an output procedure for generating an output indicating the presence, absence or kind of said fetal aneuploidy. The method of the invention can be performed using a computer-readable medium having stored thereon computer-readable instructions for carrying out a method for identifying any CNV e.g. chromosomal or partial aneuploidies. In one embodiment, the invention provides a computer-readable medium having stored thereon computer-readable instructions for identifying at least one chromosome suspected to be involved with a chromosomal aneuploidy e.g. trisomy 21, trisomy, 13, trisomy 18, or monosomy X.

In one embodiment, the invention provides a computer-readable medium having stored thereon computer-readable instructions for carrying out a method comprising the steps: (a) using sequence information obtained from fetal and maternal nucleic acids in a sample to identify a number of sequence tags for a chromosome of interest and a number of sequence tags for at least two normalizing chromosomes; (b) using the numbers of sequence tags to calculate a first normalizing value and a second normalizing value for the chromosome of interest; and (c) comparing the first normalizing value for the chromosome of interest to a first threshold value and comparing the second normalizing value for the chromosome of interest to a second threshold value to determine the presence or absence of a fetal aneuploidy in the sample. The computer-readable medium may have stored thereon computer-readable instructions for carrying out a method wherein the first normalizing value for the chromosome of interest is a first chromosome dose, the first chromosome dose being a ratio of the number of sequence tags for the chromosome of interest and a first normalizing chromosome, and wherein the second normalizing value for the chromosome of interest is a second chromosome dose, the second chromosome dose being a ratio of the number of sequence tags for the chromosome of interest and a second normalizing chromosome.

In one embodiment, the invention provides a computer-readable medium having stored thereon computer-readable instructions for carrying out a method comprising the steps: (a) using sequence information obtained from fetal and maternal nucleic acids in a sample to identify a number of sequence tags for a chromosome of interest and a number of sequence tags for at least two normalizing chromosomes; (b) using the number of sequence tags for the chromosome of interest and the number of sequence tags for a first normalizing chromosome to determine a first normalizing value for the chromosome of interest, and using the number of sequence tags for the first normalizing chromosome and the number of sequence tags for a second normalizing chromosome to determine a second normalizing value for the first normalizing chromosome; (c) comparing the first normalizing value for the chromosome of interest to a first threshold value and comparing the second normalizing value for the first normalizing chromosome to a second threshold value to determine the presence or absence of a fetal aneuploidy in the sample. The computer-readable medium may have stored thereon computer-readable instructions for carrying out a method wherein the first normalizing value for the chromosome of interest is a first chromosome dose, the first chromosome dose being a ratio of the number of sequence tags for the chromosome of interest and a first normalizing chromosome, and wherein the second normalizing value for the chromosome of interest is a second chromosome dose, the second chromosome dose being a ratio of the number of sequence tags for the first normalizing chromosome and a second normalizing chromosome.

In one embodiment, the invention provides a computer processing system which is adapted or configured to perform a method according to the invention. For example, the invention provides a computer processing system which is adapted and configured to carry out a method comprising the steps: (a) using sequence information obtained from fetal and maternal nucleic acids in a sample to identify a number of sequence tags for a chromosome of interest and a number of sequence tags for at least two normalizing chromosomes; (b) using the numbers of sequence tags to calculate a first normalizing value and a second normalizing value for the chromosome of interest; and (c) comparing the first normalizing value for the chromosome of interest to a first threshold value and comparing the second normalizing value for the chromosome of interest to a second threshold value to determine the presence or absence of a fetal aneuploidy in the sample. The computer processing system may be adapted and configured to carry out a method wherein the first normalizing value for the chromosome of interest is a first chromosome dose, the first chromosome dose being a ratio of the number of sequence tags for the chromosome of interest and a first normalizing chromosome, and wherein the second normalizing value for the chromosome of interest is a second chromosome dose, the second chromosome dose being a ratio of the number of sequence tags for the chromosome of interest and a second normalizing chromosome.

In one embodiment, the invention provides a computer processing system which is adapted and configured to carry out a method comprising the steps: (a) using sequence information obtained from fetal and maternal nucleic acids in a sample to identify a number of sequence tags for a chromosome of interest and a number of sequence tags for at least two normalizing chromosomes; (b) using the number of sequence tags for the chromosome of interest and the number of sequence tags for a first normalizing chromosome to determine a first normalizing value for the chromosome of interest, and using the number of sequence tags for the first normalizing chromosome and the number of sequence tags for a second normalizing chromosome to determine a second normalizing value for the first normalizing chromosome; (c) comparing the first normalizing value for the chromosome of interest to a first threshold value and comparing the second normalizing value for the first normalizing chromosome to a second threshold value to determine the presence or absence of a fetal aneuploidy in the sample. The computer processing system may be adapted and configured to carry out a method wherein the first normalizing value for the chromosome of interest is a first chromosome dose, the first chromosome dose being a ratio of the number of sequence tags for the chromosome of interest and a first normalizing chromosome, and wherein the second normalizing value for the chromosome of interest is a second chromosome dose, the second chromosome dose being a ratio of the number of sequence tags for the first normalizing chromosome and a second normalizing chromosome.

The invention also provides apparatus adapted or configured to perform a method according to the invention, wherein the apparatus optionally comprises a sequencing device adapted or configured to sequence fetal and maternal nucleic acid molecules in a sample. For example, the invention provides apparatus which comprises: (a) a sequencing device adapted or configured to sequence fetal and maternal nucleic acid molecules in a sample using a sequencing method as described herein, thereby generating sequence information; and (b) a computer processing system adapted or configured to use the sequence information generated by the sequencing device in a method as described herein, wherein the computer processing system is optionally directly linked to the sequencing device such that the sequence information can be automatically transferred from the sequencing device to the computer processing system. The apparatus may further comprise a transfer device adapted or configured to transfer samples to the sequencing device for sequencing.

The present invention is described in further detail in the following Examples which are not in any way intended to limit the scope of the invention as claimed. The attached Figures are meant to be considered as integral parts of the specification and description of the invention. The following examples are offered to illustrate, but not to limit the claimed invention.

EXAMPLES

Example 1

Optimal Determination of Fetal Chromosomal Abnormalities Using Massively Parallel DNA Sequencing of Cell Free Fetal DNA from Maternal Blood: Test Set 1 Independent of Training Set 1

The study was conducted by qualified site clinical research personnel at 13 US clinic locations between April 2009 and July 2010 under a human subject protocol approved by institutional review boards (IRBs) at each institution. Informed written consent was obtained from each subject prior to study participation. The protocol was designed to provide blood samples and clinical data to support development of noninvasive prenatal genetic diagnostic methods. Pregnant women, age 18 years or older were eligible for inclusion. For patients undergoing clinically indicated CVS or amniocentesis blood was collected prior to performance of the procedure, and results of fetal karyotype was also collected. Peripheral blood samples (two tubes or ~20 mL total) were drawn from all subjects in acid citrate dextrose (ACD) tubes (Becton Dickinson). All samples were de-identified and assigned an anonymous patient ID number. Blood samples were shipped overnight to the laboratory in temperature controlled shipping containers provided for the study. Time elapsed between blood draw and sample receipt was recorded as part of the sample accessioning.

Site research coordinators entered clinical data relevant to the patient's current pregnancy and history into study case report forms (CRFs) using the anonymous patient ID number. Cytogenetic analysis of fetal karyotype from invasive prenatal procedure samples was performed per local laboratories and the results were also recorded in study CRFs. All data obtained on CRFs were entered into a clinical database the laboratory. Cell free plasma was obtained from individual blood tubes utilizing at two-step centrifugation process within 24-48 hours of sample of venipuncture. Plasma from a single blood tube was sufficient for sequencing analysis. Cell-free DNA was extracted from cell-free plasma by using QIAamp DNA Blood Mini kit (Qiagen) according to the manufacturer's instructions. Since the cell free DNA fragments are known to be approximately 170 base pairs (bp) in length (Fan et al., Clin Chem 56:1279-1286 [2010]) no fragmentation of the DNA was required prior to sequencing.

For the training set samples, cfDNA was sent to Prognosys Biosciences, Inc. (La Jolla, Calif.) for sequencing library preparation (cfDNA blunt ended and ligated to universal adapters) and sequencing using standard manufacturer protocols with the Illumina Genome Analyzer IIx instrumentation. Single-end reads of 36 base pairs were obtained. Upon completion of the sequencing, all base call files were collected and analyzed. For the test set samples, sequencing libraries were prepared and sequencing carried out on Illumina Genome Analyzer IIx instrument. Sequencing library preparation was performed as follows. The full-length protocol described is essentially the standard protocol provided by Illumina, and only differs from the Illumina protocol in the purification of the amplified library: the Illumina protocol instructs that the amplified library be purified using gel electrophoresis, while the protocol described herein uses magnetic beads for the same purification step. Approximately 2 ng of purified cfDNA that had been extracted from maternal plasma was used to prepare a primary sequencing library using NEBNext™ DNA Sample Prep DNA Reagent Set 1 (Part No. E6000L; New England Biolabs, Ipswich, Mass.) for Illumina® essentially according to the manufacturer's instructions. All steps except for the final purification of the adaptor-ligated products, which was performed using Agencourt magnetic beads and reagents instead of the purification column, were performed according to the protocol accompanying the NEBNext™ Reagents for Sample Preparation for a genomic DNA library that is sequenced using the Illumina® GAII. The NEBNext™ protocol essentially follows that provided by Illumina, which is available at grcf.jhml.edu/hts/protocols/11257047_ChIP_Sample_Prep.pdf.

The overhangs of approximately 2 ng purified cfDNA fragments contained in 40 µl were converted into phosphorylated blunt ends according to the NEBNext® End Repair Module by incubating the 40 µl cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 in a 200 µl microfuge tube in a thermal cycler for 30 minutes at 20° C. The sample was cooled to 4° C., and purified using a QIAQuick column provided in the QIAQuick PCR Purification Kit (QIAGEN Inc., Valencia, Calif.) as follows. The 50 µl reaction was transferred to 1.5 ml microfuge tube, and 250 µl of Qiagen Buffer PB were added. The resulting 300 µl were transferred to a QIAquick column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 39 µl Qiagen Buffer EB by centrifugation. dA tailing of 34 µl of the blunt-ended DNA was accomplished using 16 µl of the dA-tailing master mix containing the Klenow fragment (3' to 5' exo minus) (NEBNext™ DNA Sample Prep DNA Reagent Set 1), and incubating for 30 minutes at 37° C. according to the manufacturer's NEBNext® dA-Tailing Module. The sample was cooled to 4° C., and purified using a column provided in the MinElute PCR Purification Kit (QIAGEN Inc., Valencia, Calif.) as follows. The 50 µl reaction was transferred to 1.5 ml microfuge tube, and 250 µl of Qiagen Buffer PB were added. The 300 µl were transferred to the MinElute column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 15 µl Qiagen Buffer EB by centrifugation. Ten microliters of the DNA eluate were incubated with 1 µl of a 1:5 dilution of the Illumina Genomic Adapter Oligo Mix (Part No. 1000521), 15 µl of 2× Quick Ligation Reaction Buffer, and 4 µl Quick T4 DNA Ligase, for 15 minutes at 25° C. according to the NEBNext® Quick Ligation Module. The sample was cooled to 4° C., and purified using a MinElute column as follows. One hundred and fifty microliters of Qiagen Buffer PE were added to the 30 µl reaction, and the entire volume was transferred to a MinElute column were transferred to a MinElute column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 28 µl Qiagen Buffer EB by centrifugation. Twenty three microliters of the adaptor-ligated DNA eluate were subjected to 18 cycles of PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available on the world wide web at beckmangenomics.com/products/AMPureXPProtocol_000387v001.pdf. The Agencourt AMPure XP PCR purification system removes unincorporated dNTPs, primers, primer dimers, salts and other contaminates, and recovers amplicons greater than 100 bp. The purified amplified product was eluted from the Agencourt beads in 40 µl of Qiagen EB Buffer and the size distribution of the libraries was analyzed using the Agilent DNA 1000 Kit for the 2100 Bioanalyzer (Agilent technologies Inc., Santa Clara, Calif.).

For both the training and test sample sets, single-end reads of 36 base pairs were sequenced.

Data Analysis and Sample Classification

Sequence reads 36 bases in length were aligned to the human genome assembly hg18 obtained from the UCSC database (available on the world wide web at hgdownload.cse.ucsc.edu/goldenPath/hg18/bigZips/). Alignments were carried out utilizing the Bowtie short read aligner (version 0.12.5) allowing for up to two base mismatches during alignment (Langmead et al., Genome Biol 10:R25 [2009]. Only reads that unambiguously mapped to a single genomic location were included. Genomic sites where reads mapped were counted and included in the calculation of chromosome ratios (see below). Regions on the Y chromosome where sequence tags from male and female fetuses map without any discrimination were excluded from the analysis (specifically, from base 0 to base $2 \times 10^6$; base $10 \times 10^6$ to base $13 \times 10^6$; and base $23 \times 10^6$ to the end of chromosome Y).

Intra-run and inter-run sequencing variation in the chromosomal distribution of sequence reads can obscure the effects of fetal aneuploidy on the distribution of mapped sequence sites. To correct for such variation, a chromosome dose was calculated as the count of mapped sites for a given chromosome of interest is normalized to counts observed on a predetermined normalizing chromosome or a set of normalizing chromosomes. The normalizing chromosome or set of normalizing chromosomes was first identified in a subset of samples in the training set of samples that were unaffected i.e. qualified samples having diploid karyotypes for chromosomes of interest 21, 18, 13 and X, considering each autosome as a potential denominator in a ratio of counts with our chromosomes of interest. Denominator chromosomes i.e. normalizing chromosomes were selected that minimized the variation of the chromosome ratios within and between sequencing runs. Each chromosome of interest was determined to have a distinct denominator (Table 1).

The chromosome doses for each of the chromosomes of interest in the qualified samples provides a measure of the variation in the total number of mapped sequence tags for each chromosome of interest relative to that of each of the remaining chromosomes. Thus, qualified chromosome doses can identify the chromosome or a group of chromosomes i.e. normalizing chromosome that has a variation among samples that is closest to the variation of the chromosome of interest, and that would serve as ideal sequences for normalizing values for further statistical evaluation.

Chromosome doses for all samples in the training set i.e. qualified and affected, also serve as the basis for determining threshold values when identifying aneuploidies in test samples as described in the following.

TABLE 1

Normalizing Chromosomes for Determining Chromosome Doses

| Chromosome of Interest | Chromosome of Interest - Numerator (Chr mapped counts) | Normalizing Chromosome - Denominator (Chr mapped counts) |
|---|---|---|
| 21 | Chr 21 | Chr 9 |
| 18 | Chr 18 | Chr 8 |
| 13 | Chr 13 | Sum(Chr 2-6) |
| X | Chr X | Chr 6 |
| Y | Chr Y | Sum(Chr 2-6) |

For each chromosome of interest in each sample in the test set, a normalizing value was determined and used to determine the presence or absence of an aneuploidy. The normalizing value was calculated as a chromosome dose that can be further computed to provide a normalized chromosome value (NCV).

Chromosome Doses

For the test set, a chromosome dose was calculated for each chromosome of interest, 21, 18, 13, X and Y for every sample. As provided in Table above 1, the chromosome dose for chromosome 21 was calculated as a ratio of the number of tags in the test sample that mapped to chromosome 21 in the test sample, and the number of tags in the test sample that mapped to chromosome 9; the chromosome dose for chromosome 18 was calculated as a ratio of the number of tags in the test sample that mapped to chromosome 18 in the test sample, and the number of tags in the test sample that mapped to chromosome 8; the chromosome dose for chromosome 13 was calculated as a ratio of the number of tags in the test sample that mapped to chromosome 13 in the test sample, and the number of tags in the test sample that mapped to chromosomes 2-6; the chromosome dose for chromosome X was calculated as a ratio of the number of tags in the test sample that mapped to chromosome X in the test sample, and the number of tags in the test sample that mapped to chromosome 6; and the chromosome dose for chromosome Y was calculated as a ratio of the number of tags in the test sample that mapped to chromosome Y in the test sample, and the number of tags in the test sample that mapped to chromosomes 2-6.

Normalized Chromosome Values

Using the chromosome dose for each of the chromosomes of interest in each of the test samples, and the mean of the corresponding chromosome dose determined in the qualified samples of the training set, a normalized chromosome value (NCV) was calculated using the equation:

$$NCV_{ij} = \frac{x_{ij} - \hat{\mu}_j}{\hat{\sigma}_j}$$

where $\hat{\mu}_j$ AND $\hat{\sigma}_j$ are the estimated training set mean and standard deviation respectively for the j-th chromosome ratio, and $x_{ij}$ is the observed j-th chromosome ratio for sample i. When chromosome ratios are normally distributed, the NCV is equivalent to a statistical z-score for the ratios. No significant departure from linearity is observed in a quantile-quantile plot of the NCVs from unaffected samples. In addition, standard tests of normality for the NCVs fail to reject the null hypothesis of normality. For both the Kolmogrov-Smirnov and Shapiro-Wilk tests the significance value is greater than 0.05.

For the test set, an NCV was calculated for each chromosome of interest, 21, 18, 13, X and Y for every sample. To insure a safe and effective classification scheme, conservative boundaries were chosen for aneuploidy classification. For classification of the autosomes' aneuploidy state, a NCV>4.0 was required to classify the chromosome as affected (i.e. aneuploid for that chromosome) and a NCV<2.5 to classify a chromosome as unaffected. Samples with autosomes that have an NCV between 2.5 and 4.0 were classified as "no call".

Sex chromosome classification in the test was performed by sequential application of NCVs for both X and Y as follows:
1. If NCV Y>−2.0 standard deviations from the mean of male samples, then the sample was classified as male (XY).
2. If NCV Y<−2.0 standard deviations from the mean of male samples, and NCV X>−2.0 standard deviations from the mean of female samples, then the sample was classified as female (XX).
3. If NCV Y<−2.0 standard deviations from the mean of male samples, and NCV X<−3.0 standard deviations from the mean of female samples, then the sample was classified as monosomy X, i.e. Turner syndrome.
4. If the NCVs did not fit into any of the above criteria, then the sample was classified as a "no call" for sex.

Results

Study Population Demographics

A total of 1,014 patients were enrolled between April 2009 and July 2010. The patient demographics, invasive procedure type and karyotype results are summarized in Table 2. The average age of study participants was 35.6 yrs (range 17 to 47 yrs) and gestational age ranged between 6 weeks, 1 day to 38 weeks, 1 day (mean 15 weeks, 4 days). The overall incidence of abnormal fetal chromosome karyotypes was 6.8% with T21 incidence of 2.5%. Of 946 subjects with singleton pregnancies and karyotype, 906 (96%) showed at least one clinically recognized risk factor for fetal aneuploidy prior to prenatal procedure. Even eliminating those with advanced maternal age as their sole indication, the data demonstrates a very high false positive rate for current screening modalities. Ultrasound findings of increased nuchal translucency, cystic hygroma, or other structural congenital abnormality by ultrasound were most predictive of abnormal karyotype in this cohort.

TABLE 2

Patient Demographics

| | Total Enrolled (N = 1014) | Training Set (N = 71) | Test Set (N = 48) |
|---|---|---|---|
| Dates of Enrollment | April 2009-July 2010 | April 2009-December 2009 | January 2010-June 2010 |
| Number enrolled | 1014 | 435 | 575 |
| Maternal Age, yrs | | | |
| Mean (SD) | 35.6 (5.66) | 36.4 (6.05) | 34.2 (8.22) |
| Min/Max | 17/47 | 20/46 | 18/46 |
| Not Specified, N | 11 | 3 | 0 |
| Ethnicity, N (%) | | | |
| Caucasian | 636 (62.7) | 50 (70.4) | 24 (50.0) |
| Hispanic | 167 (16.5) | 6 (8.5) | 13 (27.0) |
| Asian | 63 (6.2) | 6 (8.5) | 5 (10.4) |
| Multi, more than one | 53 (5.2) | 6 (8.5) | 1 (2.1) |
| African American | 41 (4.0) | 1 (1.3) | 3 (6.3) |
| Other | 36 (3.6) | 2 (2.8) | 1 (2.1) |
| Native American | 9 (0.9) | 0 (0.0) | 1 (2.1) |
| Not Specified | 9 (0.9) | 0 (0.0) | 0 (0.0) |
| Gestational Age, wks, days | | | |
| Mean | 15 w 4 d | 14 w 5 d | 15 w 3 d |
| Min/Max | 6 w 1 d/38 w 1 d | 10 w 0 d/23 w 1 d | 10 w 4 d/28 w 3 d |

TABLE 2-continued

Patient Demographics

| | | | |
|---|---|---|---|
| Number of Fetus, N | | | |
| 1 | 982 | 67 | 47 |
| 2 | 30 | 4 | 1 |
| 3 | 2 | 0 | 0 |
| Prenatal Procedure, N (%) | | | |
| CVS | 430 (42.4) | 38 (53.5) | 28 (58.3) |
| Amniocentesis | 571 (56.3) | 32 (45.1) | 20 (41.7) |
| Not specified | 3 (0.3) | 1 (1.4) | 0 (0.0) |
| Not performed | 10 (1.0) | 0 (0.0) | 0 (0.0) |
| Fetal Karyotype, N (%) | | | |
| 46 XX | 453* (43.9) | 22* (29.7) | 7* (14.6) |
| 46 XY | 474* (45.9) | 26* (35.1) | 14 (29.2) |
| 47, +21, both sexes | 25* (2.4) | 10* (13.5) | 13 (27.1) |
| 47, +18, both sexes | 14 (1.4) | 5 (6.8) | 8 (16.7) |
| 47, +13, both sexes | 4 (0.4) | 2 (2.7) | 1 (2.1) |
| 45, X | 8 (0.8) | 3 (4.1) | 3 (6.3) |
| Complex, other | 18* (1.7) | 6 (8.1) | 2 (4.2) |
| Karyotype not available | 36 (3.5) | 0 (0.0) | 0 (0.0) |
| Prenatal Screening Risks for Karyotyped Singletons, N (%) | Non-sequenced N = 834 | Analyzed Training N = 65 | Analyzed Test N = 47 |
| AMA only (≧35 years) | 445 (53.4) | 27 (41.5) | 21 (44.7) |
| Screen positive (trisomy)** | 149 (17.9) | 18 (27.7) | 9 (19.1) |
| Increased NT | 35 (4.2) | 3 (4.6) | 5 (10.6) |
| Cystic Hygroma | 12 (1.4) | 5 (7.7) | 4 (8.5) |
| Cardiac Defect | 14 (1.7) | 0 (0.0) | 4 (8.5) |
| Other Congenital Abnormality | 78 (9.4) | 4 (6.2) | 3 (6.4) |
| Other Maternal Risk | 64 (7.7) | 5 (7.7) | 1 (2.1) |
| None specified | 37 (4.4) | 3 (4.6) | 0 (0.0) |

*Includes results of fetuses from multiple gestations,
**Assessed and reported by clinicians
Abbreviations:
AMA = Advanced Maternal Age,
NT = nuchal translucency The distribution of diverse ethnic backgrounds represented in this study population is also shown in Table 2. Overall, 63% of the patients in this study were Caucasian, 17% Hispanic, 6% Asian, 5% multi-ethnic, and 4% African American. It was noted that the ethnic diversity varied significantly from site to site. For example, one site enrolled 60% Hispanic and 26% Caucasian subjects while three clinics all located in the same state, enrolled no Hispanic subjects. As expected, there were no discernible differences observed in our results for different ethnicities.

Training Data Set 1

The training set study selected 71 samples from the initial sequential accumulation of 435 samples that were collected between April 2009 and December 2009. All subjects with affected fetus' (abnormal karyotypes) in this first series of subjects were included for sequencing and a random selection and number of non-affected subjects with adequate sample and data. Clinical characteristics of the training set patients were consistent with the overall study demographics as shown in Table 2. The gestational age range of the samples in the training set ranged from 10 weeks, 0 days to 23 weeks 1 day. Thirty-eight underwent CVS, 32 underwent amniocentesis and 1 patient did not have the invasive procedure type specified (an unaffected karyotype 46, XY). 70% of the patients were Caucasian, 8.5% Hispanic, 8.5% Asian, and 8.5% multi-ethnic. Six sequenced samples were removed from this set for the purposes of training: 4 samples from subjects with twin gestations (further discussed below), 1 sample with T18 that was contaminated during preparation, and 1 sample with a fetal karyotype 69, XXX, leaving 65 samples for the training set.

The number of unique sequence sites (i.e. tags identified with unique sites in the genome) varied from 2.2M in the early phases of the training set study to 13.7M in the latter phases due to improvements in sequencing technology over time. In order to monitor for any potential shifts in the chromosome ratios over this 6-fold range in unique sites, different unaffected samples were run at the beginning and end of the study. For the first 15 unaffected samples run, the average number of unique sites was 3.8M and the average chromosome ratios for chromosome 21 and chromosome 18 were 0.314 and 0.528, respectively. For the last 15 unaffected samples run, the average number of unique sites was 10.7M and the average chromosome ratios for chromosome 21 and chromosome 18 were 0.316 and 0.529, respectively. There was no statistical difference between the chromosome ratios for chromosome 21 and chromosome 18 over the time of the training set study.

Figure 2:
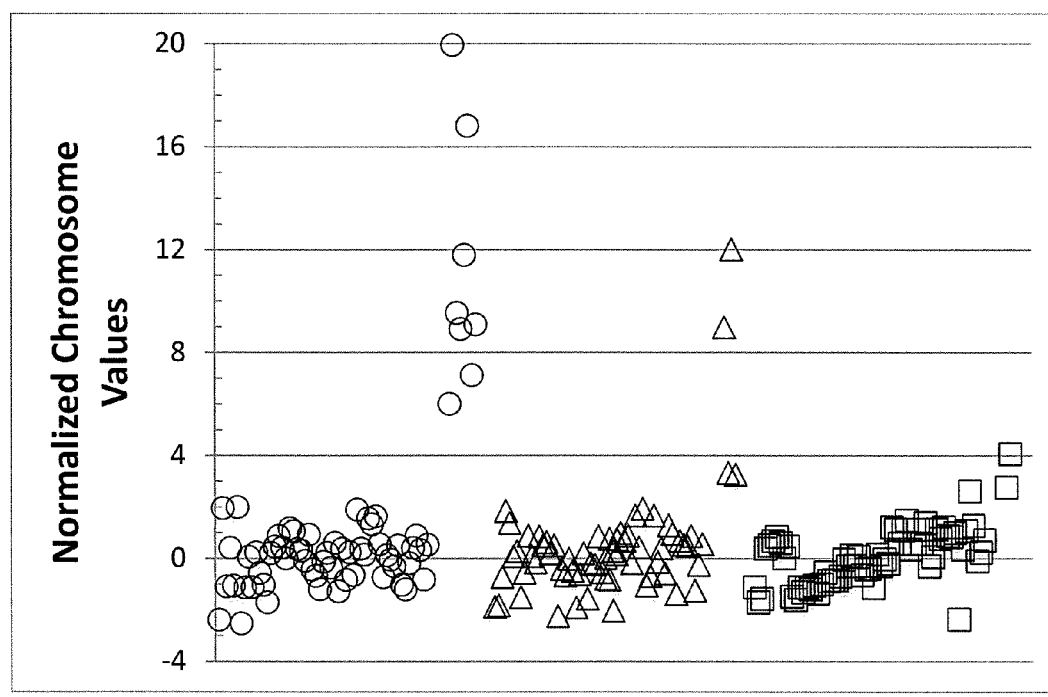
FIG. 2 shows normalized chromosome values for chromosomes 21 (○), 18 (Δ), and 13 (□) determined in samples from training set 1 (Example 1).

The training set NCVs for chromosomes 21, 18 and 13 are shown on FIG. 2. The results shown in FIG. 2 are consistent with an assumption of normality in that roughly 99% of the diploid NCVs would fall within ±2.5 standard deviations of the mean. Of this set of 65 samples, 8 samples with clinical karyotypes indicating T21 had NCVs ranging from 6 to 20. Four samples having clinical karyotypes indicative of T18 had NCVs ranging from 3.3 to 12, and the two samples having karyotypes indicative of fetal trisomy 13 (T13) had NCVs of 2.6 and 4. The spread of the NCVs in affected samples is due to their dependence on the percentage of fetal cfDNA in the individual samples.

Similar to the autosomes, the means and standard deviations for the sex chromosomes were established in the training set. The sex chromosome thresholds allowed 100% identification of male and female fetuses in the training set.

Test Data Set 1

Having established chromosome ratio means and standard deviations from the training set, a test set of 48 samples was selected from samples collected between January 2010 and June 2010 from 575 total samples. One of the samples from a twin gestation was removed from the final analysis leaving 47 samples in the test set. Personnel preparing samples for sequencing and operating the equipment were blinded to the clinical karyotype information. The gestational age range was similar to that seen in the training set (Table 2). 58% of the invasive procedures were CVS, higher than that of the overall procedural demographics, but also similar to the training set. 50% of subjects were Caucasian, 27% Hispanic, 10.4% Asian and 6.3% African American.

Figure 3:
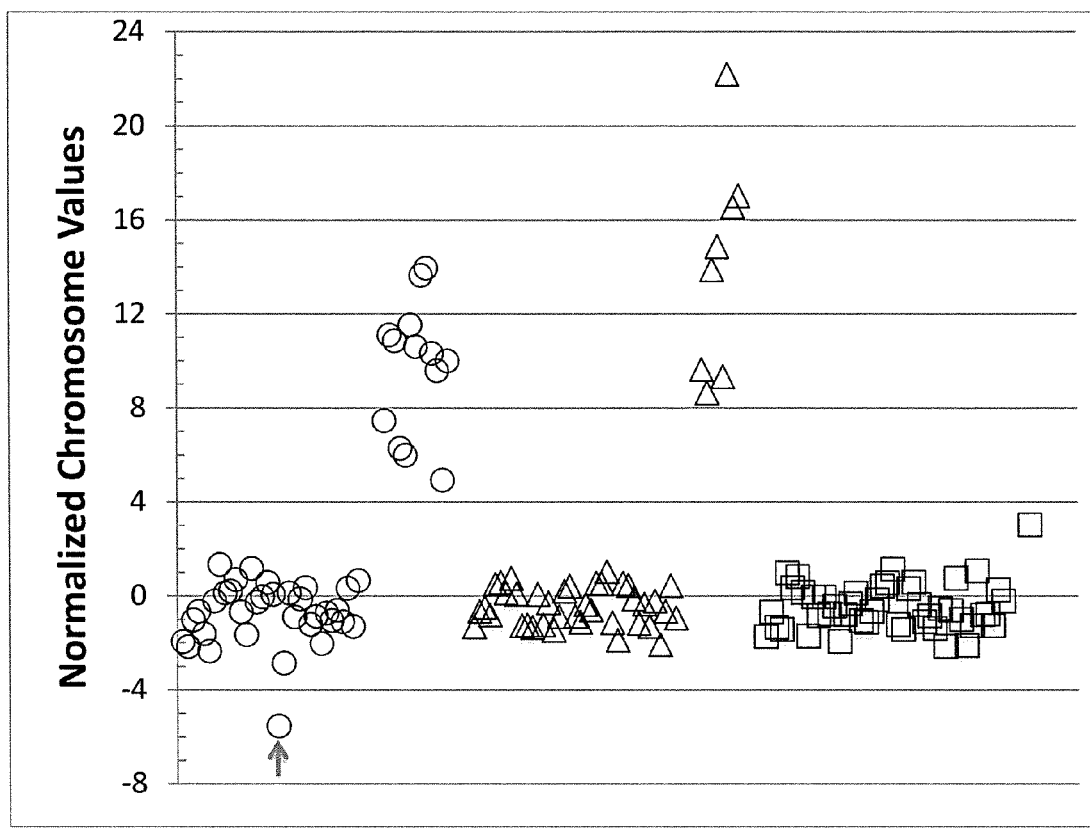
FIG. 3 shows normalized chromosome values for chromosomes 21 (○), 18 (Δ), and 13 (□) determined in samples from test set 1 (Example 1).

In the test set, the number of unique sequence tags varied from approximately 13M to 26M. For unaffected samples, the chromosome ratios for chromosome 21 and chromosome 18 were 0.313 and 0.527, respectively. The test set NCVs for chromosome 21, chromosome 18 and chromosome 13 are shown in FIG. 3 and the classifications are given in Table 3.

TABLE 3

Test Set Classification Data Test Set Classification Data

T21 classification

| Karyotype | Unaffected for T21 | T21 | No Call |
|---|---|---|---|
| Unaffected for T21 | 34 | | |
| 47,XX or XY + 21 | | 13 | |

T18 classification

| Karyotype | Unaffected for T18 | T18 | No Call |
|---|---|---|---|
| Unaffected for T18 | 39 | | |
| 47,XX or XY + 18 | | 8 | |

T13 classification

| Karyotype | Unaffected for T13 | T13 | No Call |
|---|---|---|---|
| Unaffected for T13 | 46 | | |
| 47,XX or XY + 13 | | | 1 |

Sex Chromosome Classification

| Karyotype | XY | XX | MX* | No Call |
|---|---|---|---|---|
| 46, XY | 24 | | | |
| 46, XX | | 18 | | 1 |
| 45, X | | | 2 | 1 |
| Cplx | 1 | | | |

*MX is monosomy in the X chromosome with no evidence of Y chromosome

In the test set, 13/13 subjects having clinical karyotypes that indicated fetal T21 were correctly identified having NCVs ranging from 5 to 14. Eight/eight subjects having karyotypes that indicated fetal T18 were correctly identified having NCVs ranging from 8.5 to 22. The single sample having a karyotype classified as T13 in this test set was classified as a no call with an NCV of approximately 3.

For the test data set, all male samples were correctly identified including a sample with complex karyotype, 46,XY+ marker chromosome (unidentifiable by cytogenetics) (Table 3). Nineteen of twenty female samples were correctly identified, and one female sample was categorized as a no call. For three samples in the test set with karyotype of 45,X, two of the three were correctly identified as monosomy X and 1 was classified as a no call (Table 3).

Twins

Four of the samples initially selected for the training set and one of the samples in the test set were from twin gestations. The thresholds being employed here could be confounded by the differing amount of cfDNA expected in the setting of a twin gestation. In the training set, the karyotype from one of the twin samples was monochorionic 47,XY+21. A second twin sample was fraternal and amniocentesis was carried out on each of the fetuses individually. In this twin gestation, one of the fetuses had a karyotype of 47,XY+21 while the other had a normal karyotype, 46,XX. In both of these cases the cell free classification based on the methods discussed above classified the sample as T21. The other two twin gestations in the training set were classified correctly as non-affected for T21 (all twins showed diploid karyotype for chromosome 21). For the twin gestation sample in the test set, karyotype was only established for Twin B (46,XX) and the algorithm correctly classified as non-affected for T21.

Conclusion

The data show that massively parallel sequencing can be used to determine a plurality abnormal fetal karyotypes from the blood of pregnant women. These data demonstrate that 100% correct classification of samples with trisomy 21 and trisomy 18 can be identified using independent test set data. Even in the case of fetuses with abnormal sex chromosome karyotypes, none of the samples were incorrectly classified with the algorithm of the method. Importantly, the algorithm also performed well in determining the presence of T21 in two sets of twin pregnancies having at least one affected fetus, which has never been shown previously. Furthermore, this study examined a variety of sequential samples from multiple centers representing not only the range of abnormal karyotypes that one is likely to witness in a commercial clinical setting, but showing the significance of accurately classifying pregnancies non-affected by common trisomies to address the unacceptably high false positive rates that remain in prenatal screening today. The data provide valuable insight into the vast capabilities of employing this method in the future. Analysis of subsets of the unique genomic sites showed increases in the variance consistent Poisson counting statistics.

The data build on the findings of Fan and Quake who demonstrated that the sensitivity of noninvasive prenatal determination of fetal aneuploidy from maternal plasma using massively parallel sequencing is only limited by the counting statistics (Fan and Quake, PLos One 5, e10439 [2010]). Because sequencing information was collected across the entire genome, this method is capable of determining any aneuploidy or other copy number variation including insertions and deletions. The karyotype from one of the samples had a small deletion in chromosome 11 between q21 and q23 that was observed as a ~10% decrease in the relative number of tags in a 25 Mbase region starting at q21 when the sequencing data was analyzed in 500 kbase bins. In addition, in the training set, three of the samples had complex sex karyotypes due to mosaicism in the cytogenetic analysis. These karyotypes were: i) 47,XXX[9]/45,X[6], ii) 45,X [3]/ 46, XY[17], and iii) 47,XXX[13]/45,X[7]. Sample ii, which showed some XY-containing cells was correctly classified as XY. Samples i (from CVS procedure) and iii (from amniocentesis), which both showed a mixture of XXX and X cells by cytogenetic analysis (consistent with mosaic Turner syndrome), were classified as a no call and monosomy X, respectively.

In testing the algorithm, another interesting data point was observed having an NCV between −5 and −6 for chromosome 21 for one sample from the test set (FIG. 3). Although this sample was diploid in chromosome 21 by cytogenetics, the karyotype showed mosaicism with partial triploidy for chromosome 9; 47, XX+9 [9]/46, XX [6]. Since chromosome 9 is used in the denominator to determine the chromosome dose for chromosome 21 (Table 1), this lowers the overall NCV value. The result strikingly demonstrates the ability of the method to determine fetal trisomy 9 in this case (see Example 2). Multiple chromosome ratios were determined to insure correct classification for the chromosomes of interest. In addition, normalizing chromosomes for all the autosomes were established to increase the probability of determining rare aneuploidies across the genome (See Example 5).

Figure 4:
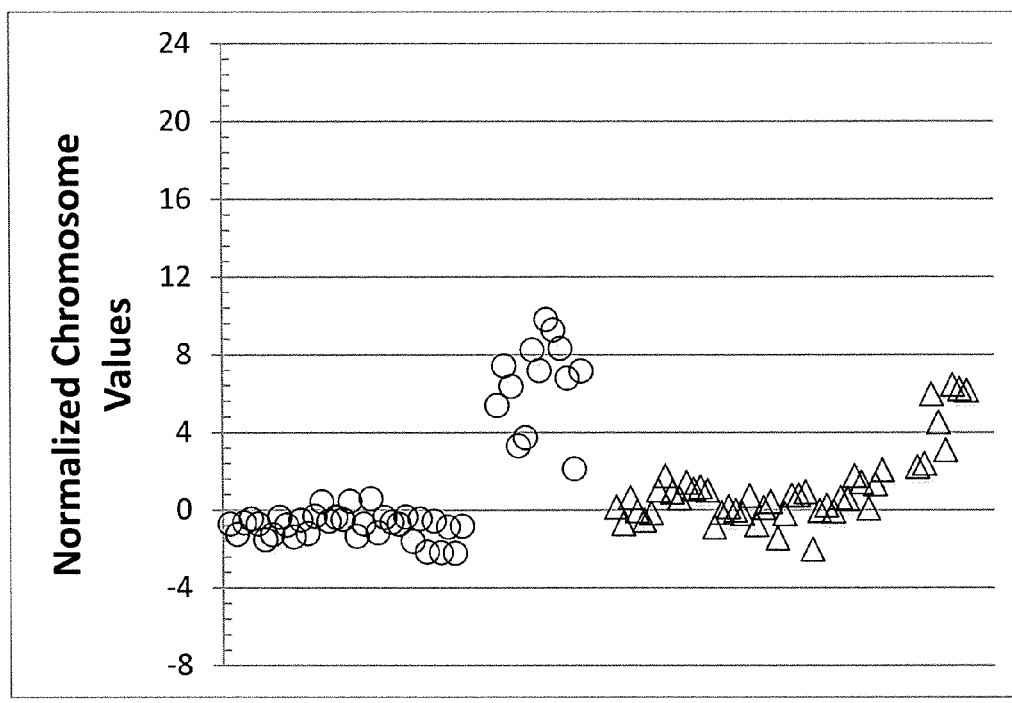
FIG. 4 shows normalized chromosome values for chromosomes 21 (○) and 18 (Δ) determined in samples from test set 1 using the normalizing method of Chiu et al. (Example 1).

The conclusion of Fan, et al regarding the sensitivity of these methods is only correct if the algorithms being utilized are able to account for any random or systematic biases introduced by the sequencing method. If the sequencing data is not properly normalized the resulting analysis will be inferior to the counting statistics. Chiu, et al noted in their recent paper that their measurement of chromosomes 18 and 13 using the massively parallel sequencing method was imprecise, and concluded that more research was necessary to apply the method to the determination of T18 and T13 (Chiu et al., BMJ 342:c7401 [2011]). The method utilized in the Chiu, et al paper simply uses the number of sequence tags on the chromosome of interest, in their case chromosome 21, normalized by the total number of tags in the sequencing run. The challenge for this approach is that the distribution of tags on each chromosome can vary from sequencing run to sequencing run, and thus increases the overall variation of the aneuploidy determination metric. In order to compare the results of the Chiu algorithm to the chromosome ratios used in this paper, the test data for chromosomes 21 and 18 was reanalyzed using the method recommended by Chiu, et al as shown in FIG. 4. Overall, a compression in the range of NCV for each of the chromosomes 21 and 18 was observed as well as a decrease in the determination rate with 10/13 T21 and 5/8 of the T18 samples correctly identified from our test set utilizing an NCV threshold of 4.0 for aneuploidy classification.

Ehrich, et al also focused only on T21 and used the same algorithm as Chiu, et al., (Ehrich et al., Am J Obstet Gynecol 204:205 e1-e11 [2011]). In addition, after observing a shift in their test set z-score metric from the external reference data i.e. training set, they retrained on the test set to establish the classification boundaries. Although in principle this approach is feasible, in practice it would be challenging to decide how many samples are required to train and how often one would need to retrain to ensure that the classification boundaries are correct. One method of mitigating this issue is to include controls in every sequencing run that measure the baseline and calibrate for quantitative behavior.

The data obtained using the present method show that massively parallel sequencing is capable of determining multiple fetal chromosomal abnormalities from the plasma of pregnant women when the algorithm for normalizing the chromosome counting data is optimized. The present method for quantification not only minimizes random and systematic variations between sequencing runs, but also allow for effective classification of aneuploidies across the entire genome, most notably T21 and T18. Larger sample collections are required to test the algorithm for T13 determination. To this end, a prospective, blinded, multi-site clinical study to further demonstrate the diagnostic accuracy of the present method is being performed.

Example 2

Use of Multiple Chromosome Ratios to Verify Determination of Aneuploidy: Normalizing Normalizing Chromosomes As described in the previous Example, the present method is based on the normalization of the number sequence tags mapped to a chromosome of interest to the number of sequence tags mapped to a chromosome that displays similar variability across samples and across sequencing runs to the chromosome of interest. To verify the classification of an aneuploidy and exclude that the normalizing chromosome used in the analysis is itself an aneuploid chromosome i.e. present in aberrant copy number, normalization of the first normalizing chromosome i.e. the chromosome used for determining a chromosome dose for classifying the common aneuploidies involving chromosomes 21, 18 and X, was determined as follows.

Using the qualifying samples from the training set 1, and the qualifying samples from test set 1 as described in Example 1, sequencing information was analyzed to identify at least one second normalizing chromosome for the first normalizing chromosome used to determine the presence or absence of a T21, T18 or chromosome X aneuploidy (see Tables 4, 5, and 6, respectively).

A. Second Normalizing Chromosome for First Normalizing Chromosome 9:

To verify the determination of a normal chromosome 21 genotype determined using first normalizing chromosome 9 as determined in Example 1, chromosome doses were calculated for chromosome 9 using each of the other chromosomes i.e. as ratios of tags mapped to chromosome 9 to tags mapped to chromosomes 1-8, and 10-22 in each of qualified samples (normal samples) in the training set 1, and in each of the qualified samples in the test set, and the % CV was calculated (Table 4). As described previously, the % CV used to identify normalizing chromosomes are CV values of chromosome doses determined in diploid samples.

TABLE 4

Determination of Second Normalizing Chromosomes for First Normalizing Chromosome 9

| Training Set 1 | | Test set 1 | |
| --- | --- | --- | --- |
| | % CV | | % CV |
| Chr22 | 9.291074 | Chr19 | 8.111788 |
| Chr19 | 8.897349 | Chr22 | 7.855368 |
| Chr4 | 5.76344 | Chr4 | 5.284925 |
| Chr17 | 5.571726 | Chr17 | 5.121887 |
| Chr16 | 4.53673 | Chr16 | 4.190157 |
| Chr20 | 4.058794 | Chr20 | 3.830602 |
| Chr5 | 3.237778 | Chr5 | 2.825374 |
| Chr6 | 3.181269 | Chr6 | 2.800885 |
| Chr3 | 2.981951 | Chr3 | 2.67343 |
| Chr8 | 2.111639 | Chr8 | 1.819142 |
| Chr2 | 1.75712 | Chr2 | 1.680979 |
| Chr7 | 1.526366 | Chr7 | 1.357402 |
| Chr12 | 1.328557 | Chr15 | 1.311336 |
| Chr15 | 1.30808 | Chr12 | 1.122218 |
| Chr14 | 0.999624 | Chr14 | 0.954458 |
| Chr10 | 0.770065 | Chr1 | 0.86791 |
| Chr1 | 0.720795 | Chr10 | 0.781235 |

TABLE 4-continued

Determination of Second Normalizing Chromosomes for First Normalizing Chromosome 9

| Training Set 1 | | Test set 1 | |
| --- | --- | --- | --- |
| | % CV | | % CV |
| Chr11 | 0.625072 | Chr11 | 0.611422 |
| Chr9 | 0 | Chr9 | 0 |

The chromosome having the lowest variability was determined to be chromosome 11 in qualified samples from both the training set and the test set.

Figure 5:
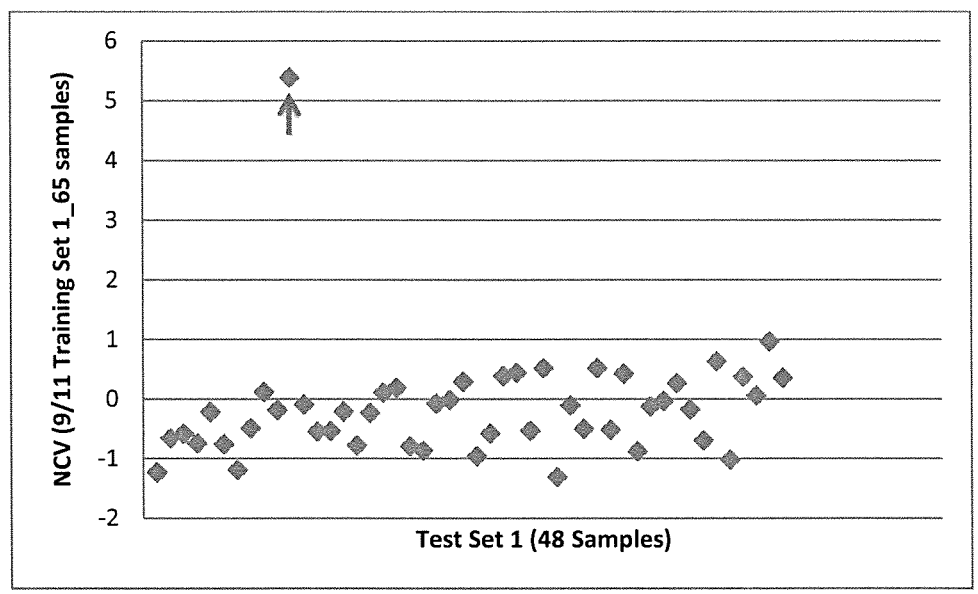
FIG. 5 shows a plot of Normalized Chromosome Values for doses of chromosome 9 determined in 48 samples in Test set 1 (Example 1) using chromosome 11 as the normalizing chromosome.

Having selected chromosome 11 as the second normalizing chromosome for the verifying the determination of aneuploidy for chromosome 21 i.e. T21, using first normalizing chromosome 9, chromosome doses for chromosome 9/chromosome 11 were calculated for each of the test samples. NCVs for each of the test samples were determined as described in Example 1 using the average chromosome dose of 0.834054±0.005213 (mean±S.D.) for chromosome 9/chromosome 11 as determined in the qualified samples of the training set (FIG. 5).

The data show that the aberrantly low NCV calculated for chromosome 21 using chromosome 9 (5-6 NCV below the mean of the remaining test samples; FIG. 3) corresponds with an aberrantly high NCV for chromosome 9 when using chromosome 11 as the second normalizing chromosome (5-6 NCV above the mean of the remaining test samples). The data indicate that the sample has a chromosome 9 aneuploidy, and verify the determination of a diploid chromosome 21 in the sample. This result is consistent with an aneuploid karyotype for the sample, which had been shown to be a trisomy 9 mosaic 47, XX+9 [9]/46, XX [6]. The karyotype of the trisomy 9 was determined using an amniotic fluid sample. In addition, these data show that the method is capable of identifying rare chromosomal aneuploidies e.g. trisomy 9.

B. Second Normalizing Chromosome for First Normalizing Chromosome 8:

Chromosome doses for chromosome 8, which is the normalizing chromosome that was used to determine the presence or absence of T18 as described in Example 1, were calculated for each of the other chromosomes i.e. as ratios of tags mapped to chromosome 8 to chromosomes 1-7, and 9-22 in each of qualified samples (normal samples) in training set 1, and in each of the qualified samples in test set 1, and the % CV was calculated (Table 5).

TABLE 5

Determination of Second Normalizing Chromosomes for First Normalizing Chromosome 8

| Training set 1 | | Test set 1 | |
| --- | --- | --- | --- |
| | % CV | | % CV |
| Chr22 | 11.46522 | Chr19 | 9.798657 |
| Chr19 | 11.047 | Chr22 | 9.563598 |
| Chr17 | 7.703968 | Chr17 | 6.814218 |
| Chr16 | 6.62974 | Chr16 | 5.872925 |
| Chr20 | 6.141408 | Chr20 | 5.520658 |
| Chr4 | 3.705126 | Chr4 | 3.528544 |
| Chr15 | 3.206262 | Chr15 | 2.863827 |
| Chr10 | 2.698991 | Chr1 | 2.340634 |
| Chr1 | 2.693637 | Chr10 | 2.249778 |
| Chr11 | 2.519884 | Chr11 | 2.03519 |
| Chr9 | 2.117622 | Chr9 | 1.808857 |
| Chr14 | 1.268471 | Chr5 | 1.046654 |

TABLE 5-continued

Determination of Second Normalizing Chromosomes for First Normalizing Chromosome 8

| Training set 1 | | Test set 1 | |
| --- | --- | --- | --- |
| | % CV | | % CV |
| Chr5 | 1.175661 | Chr6 | 1.042236 |
| Chr6 | 1.141192 | Chr14 | 1.011047 |
| Chr3 | 0.962767 | Chr3 | 0.89667 |
| Chr12 | 0.902309 | Chr12 | 0.819304 |
| Chr7 | 0.699651 | Chr7 | 0.605317 |
| Chr2 | 0.529831 | Chr2 | 0.304911 |
| Chr8 | 0 | Chr8 | 0 |

The chromosome having the lowest variability was determined to be chromosome 11 in qualified samples from both the training set and the test set.

Having selected chromosome 2 as the second normalizing chromosome for the verifying the determination of aneuploidy for chromosome 18 i.e. T18, using first normalizing chromosome 8, chromosome doses for chromosome 8/chromosome 2 were calculated for each of the test samples. NCVs for each of the test samples were determined using the average chromosome dose of 0.60102532±0.00318442 (mean±S.D.) for chromosome 8/chromosome 2 as determined in the qualified samples of the training set (FIG. 6).

Figure 6:
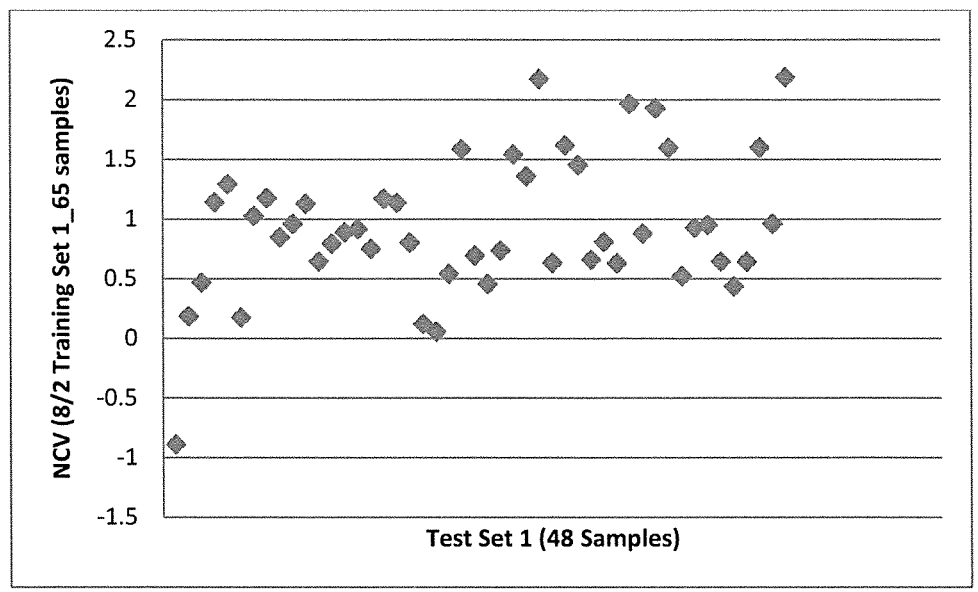
FIG. 6 shows a plot of Normalized Chromosome Values for doses of chromosome 8 determined in 48 samples in Test set 1 (Example 1) using chromosome 2 as the normalizing chromosome.

FIG. 6 shows that an aneuploidy for first normalizing chromosome 8 was absent in all the test samples, thus verifying the determination of the presence or absence of a T18 aneuploidy determined using chromosome 8 as the normalizing chromosome.

C. Second Normalizing Chromosome for First Normalizing Chromosome 6:

Chromosome doses for chromosome 6, which is the normalizing chromosome that was used to determine the presence or absence of an aneuploidy of chromosome X as described in Example 1, were calculated for each of the other chromosomes i.e. as ratios of tags mapped to chromosome 6 to chromosomes 1-5, and 7-22 in each of qualified samples (normal samples) in the training set, and in each of the qualified samples in the test set, and the % CV was calculated (Table 6).

TABLE 6

Determination of Second Normalizing Chromosomes for First Normalizing Chromosome 6

| Training set 1 | | Test set 1 | |
| --- | --- | --- | --- |
| | % CV | | % CV |
| Chr22 | 12.5071 | Chr19 | 10.78333 |
| Chr19 | 12.0931 | Chr22 | 10.54754 |
| Chr17 | 8.746929 | Chr17 | 7.786613 |
| Chr16 | 7.688881 | Chr16 | 6.870243 |
| Chr20 | 7.189759 | Chr20 | 6.517251 |
| Chr15 | 4.216819 | Chr15 | 3.828722 |
| Chr10 | 3.742112 | Chr1 | 3.301578 |
| Chr1 | 3.722392 | Chr10 | 3.229611 |
| Chr11 | 3.558687 | Chr11 | 3.025084 |
| Chr9 | 3.171762 | Chr9 | 2.791694 |
| Chr4 | 2.642087 | Chr4 | 2.563439 |
| Chr14 | 2.275682 | Chr14 | 1.962283 |
| Chr12 | 1.905575 | Chr12 | 1.774915 |
| Chr7 | 1.730526 | Chr7 | 1.534558 |
| Chr2 | 1.461087 | Chr2 | 1.147422 |

TABLE 6-continued

Determination of Second Normalizing Chromosomes for First Normalizing Chromosome 6

| Training set 1 | | Test set 1 | |
|---|---|---|---|
| | % CV | | % CV |
| Chr8 | 1.136377 | Chr8 | 1.04368 |
| Chr3 | 0.367681 | Chr5 | 0.306341 |
| Chr5 | 0.32993 | Chr3 | 0.245471 |
| Chr6 | 0 | Chr6 | 0 |

The chromosome having the lowest variability was determined to be chromosome 5 in qualified samples in the training set, and chromosome 3 in the qualified samples of the test set.

Having selected chromosome 5 as the second normalizing chromosome for verifying the determination of aneuploidy for chromosome X e.g. monosomy X using first normalizing chromosome 6, chromosome doses for chromosome 6/chromosome 5 were calculated for each of the test samples. NCVs for each of the test samples were determined using the average chromosome dose of 0.954309±0.003149 (mean±S.D.) for chromosome 6/chromosome 5 as determined in the qualified samples of the training set 1.

Figure 7:
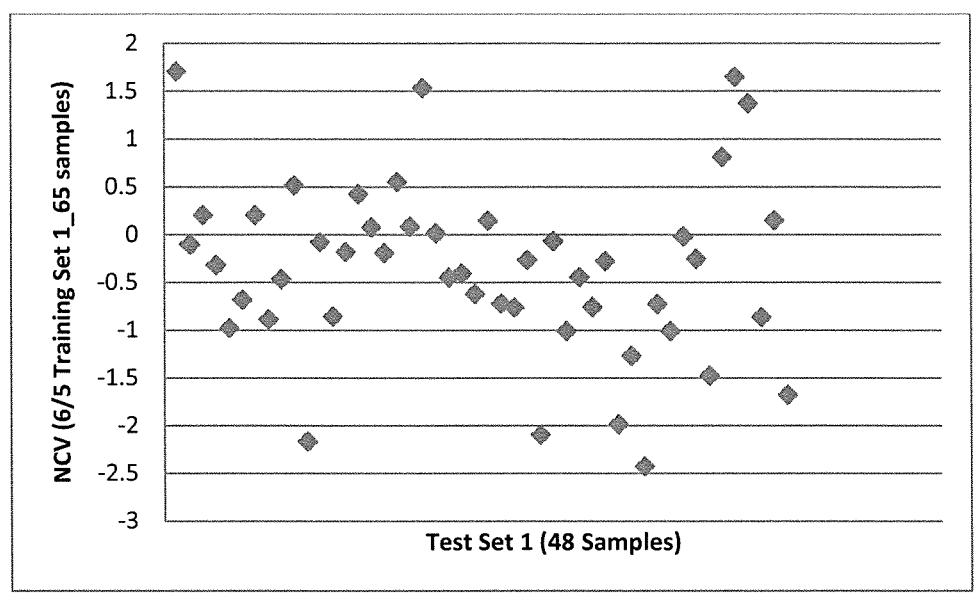
FIG. 7 shows a plot of Normalized Chromosome Values for doses of chromosome 6 determined in 48 samples in Test set 1 (Example 1) using chromosome 5 as the normalizing chromosome.

FIG. 7 shows that an aneuploidy for second normalizing chromosome 5 was absent in all the test samples, thus verifying the determination of the presence or absence of a chromosome X aneuploidy determined using chromosome 6 as the first normalizing chromosome.

These data indicate that the present method can be used to determine rare aneuploidies e.g. trisomy 9, and that the present method can be used to verify the result of a determination of the presence or absence of an aneuploidy for chromosomes of interest by normalizing the first normalizing chromosome with a second normalizing chromosome. Normalization of the first normalizing chromosome verifies the first results by confirming the presence or absence of an aneuploidy for the first normalizing chromosome, and determining the presence or absence of an aneuploidy in the first or second normalizing chromosome.

Example 3

Determination and Verification of a Chromosomal Aneuploidy Using at Least Two Normalizing Chromosomes for a Chromosome of Interest To demonstrate that the determination of a chromosomal aneuploidy can be verified by using a first and a second normalizing chromosome for a chromosome of interest, the chromosome doses for chromosome 21 in Example 1A that were computed using chromosome 9 as the first normalizing chromosome, were calculated using chromosome 10 and chromosome 14 as the second and third normalizing chromosome for chromosome of interest 21.

FIG. 8A shows a plot of NCVs for the 48 samples in test set 1 calculated using the mean and S.D. of the corresponding chromosome doses in the qualified samples of training set 1. The mean % CV of chromosome doses for chromosome 21 in training set 1 are provided in Table 7.

TABLE 7

Determination of Second Normalizing Chromosomes for Chromosome of Interest Chromosome 21

| Training Set 1 | | Test Set 1 | |
|---|---|---|---|
| | % CV | | % CV |
| ChrY | 81.98064 | ChrY | 82.78696 |
| Chr22 | 8.096499 | Chr19 | 8.646585 |
| Chr19 | 7.657979 | Chr22 | 8.445861 |
| ChrX | 5.651177 | Chr17 | 5.671588 |
| Chr4 | 5.408138 | ChrX | 5.586468 |
| Chr17 | 4.958059 | Chr4 | 4.920301 |
| Chr13 | 4.65324 | Chr16 | 4.793311 |
| Chr16 | 4.148073 | Chr20 | 4.476581 |
| Chr20 | 3.803907 | Chr13 | 4.071612 |
| Chr5 | 3.124174 | Chr18 | 3.570399 |
| Chr6 | 3.059323 | Chr5 | 2.398359 |
| Chr3 | 2.897794 | Chr6 | 2.37894 |
| Chr18 | 2.550919 | Chr3 | 2.268173 |
| Chr8 | 2.052522 | Chr15 | 1.862794 |
| Chr2 | 1.784604 | Chr8 | 1.400578 |
| Chr7 | 1.532462 | Chr1 | 1.3214 |
| Chr12 | 1.488691 | Chr2 | 1.303358 |
| Chr15 | 1.445682 | Chr10 | 1.232134 |
| Chr14 | 1.212778 | Chr11 | 0.959397 |
| Chr1 | 1.090117 | Chr7 | 0.956681 |
| Chr10 | 1.089907 | Chr12 | 0.851336 |
| Chr11 | 1.037469 | Chr9 | 0.772917 |
| Chr9 | 0.747884 | Chr14 | 0.741307 |
| Chr21 | 0 | Chr21 | 0 |

The test sample identified in FIG. 3 for having an unusually low NCV of between −5 and −6 NCV and having been classified correctly as a diploid for chromosome 21 when using chromosome 9 as a first normalizing chromosome is indicated in FIG. 8A by the arrow. In addition to using chromosome 9 as the first normalizing chromosome, the presence or absence of trisomy 21 was determined in all tests samples of test set 1 using chromosome 10 and using chromosome 14 as additional normalizing chromosomes. An average of 0.259070±0.002823 S.D. was used for second normalizing chromosome 10, and an average 0.409420±00.4965 S.D. was used for second normalizing chromosome 14 to calculate the NCVs shown in FIGS. 8B and 8C, respectively.

The data shown in FIGS. 8 B and C show that the sample previously classified as diploid for chromosome 21 when chromosome 9 was used as a first normalizing chromosome (FIGS. 3 and 8A), was confirmed to be diploid for chromosome 21 when chromosome 10 (FIG. 8B) or chromosome 14 (FIG. 8C) were used as the normalizing chromosomes.

Therefore, determination of the presence or absence of a chromosomal aneuploidy can be verified by using at least two different chromosomes as normalizing chromosomes for a chromosome of interest.

Example 4

Determination of a Chromosomal Aneuploidy in Second Normalizing Chromosome for First Normalizing Chromosome 8

To demonstrate that in addition to determining the presence of rare chromosomal abnormalities other than the trisomy 9 as determined in Examples 1 and 2, sequence information was obtained from a second training set and a second test set, and NCVs for all chromosome doses for each of chromosomes 1-22 were calculated as described above.

Determinations of the presence or absence of aneuploidies involving chromosome 18 in samples from Test set 2 were made using chromosome 8 as the first normalizing chromosome. To verify that the determinations of the presence or absence of trisomy 18 in the test samples, chromosome doses for chromosome 8 were calculated for each of the other chromosomes i.e. as ratios of tags mapped to chromosome 8 to chromosomes 1-7, and 9-22 in each of qualified samples (normal samples) in training set 2, and in each of the qualified samples in test set 2, and the % CV was calculated (Table 8).

TABLE 8

Determination of Second Normalizing Chromosomes for First Normalizing Chromosome 8

| Training set 2 | | Test set 2 | |
|---|---|---|---|
| | % CV | | % CV |
| Chr19 | 5.904815 | Chr22 | 8.770626 |
| Chr22 | 5.556697 | Chr19 | 8.562072 |
| Chr17 | 4.25183 | Chr17 | 6.237912 |
| Chr16 | 3.279849 | Chr16 | 4.900381 |
| Chr20 | 3.077099 | Chr20 | 4.681362 |
| Chr15 | 2.022277 | Chr4 | 2.787432 |
| Chr4 | 1.717953 | Chr15 | 2.565708 |
| Chr1 | 1.631726 | Chr1 | 2.305568 |
| Chr11 | 1.400395 | Chr11 | 2.024559 |
| Chr10 | 1.371933 | Chr10 | 2.022278 |
| Chr9 | 1.234463 | Chr9 | 1.757622 |
| Chr14 | 0.899747 | Chr14 | 1.163575 |
| Chr12 | 0.733874 | Chr6 | 0.860914 |
| Chr7 | 0.66061 | Chr5 | 0.852043 |
| Chr6 | 0.520435 | Chr7 | 0.818984 |
| Chr5 | 0.502611 | Chr12 | 0.801362 |
| Chr3 | 0.484482 | Chr3 | 0.764795 |
| Chr2 | 0.400574 | Chr2 | 0.525098 |
| Chr8 | 0 | Chr8 | 0 |

The chromosome having the lowest variability was determined to be chromosome 2 in qualified samples from both the training set and the test set, and was use as the second normalizing chromosome for verifying the determination of the presence or absence of an aneuploidy for chromosome 18. Using first normalizing chromosome 8, chromosome doses for chromosome 8/chromosome 2 were calculated for each of the test samples. NCVs for each of the test samples were determined using the average chromosome dose of 0.601163±0.002408 (mean±S.D.) for chromosome 8/chromosome 2 as determined in the qualified samples of training set 2 (FIG. 9A). FIG. 9A shows an aneuploidy in a test sample that was analyzed for T18 using first normalizing chromosome 8. The abnormally low NCV of about −10 for the chromosome 8 dose when using chromosome 2 as the second normalizing chromosome indicates the presence of an aneuploidy for chromosome 2 in the test sample. To verify that the aneuploidy rests with chromosome 2 and not chromosome 8, NCVs for each of the test samples were determined using the average chromosome dose of 0.953953±0.006302 (mean±S.D.) for chromosome 8/chromosome 7 as determined in the qualified samples of training set 2 (FIG. 9B). FIG. 9B shows that none of the test samples contained an aneuploid chromosome 8 when chromosome 7 was used as second normalizing chromosome to calculate doses and NCVs for first normalizing chromosome 8.

These data confirm that the present method can be used to determine rare aneuploidies, and that the present method can be used to verify the result of a determination of the presence or absence of an aneuploidy by determining that the first normalizing chromosome used as the numerator used to calculate the dose of a chromosome of interest is itself not present in aberrant copy numbers i.e. it is not an aneuploid chromosome. As shown in Examples 2 and 3, the determination of the presence or absence of an aneuploidy can be made by using at least two different normalizing chromosomes. The different normalizing chromosomes can be used as separate numerators when calculating the chromosome dose and NCV for a chromosome of interest, and comparing the results to ascertain the same outcome. Alternatively, the first of the two different normalizing chromosomes can be used to calculate the dose and NCV for a chromosome of interest, and the second normalizing chromosome can be used to calculate the dose and NCV of the first normalizing chromosome to verify that the first normalizing chromosome is devoid of an aneuploidy.

Example 5

Determination of First and Second Normalizing Chromosomes for the Determination of Chromosomal Aneuploidies To identify normalizing chromosomes for each of chromosomes 1-2, X and Y, sequencing information obtained from sequencing all samples i.e. qualified and affected, from each of training set 1, test set 1, and training set 2, was used to compute percent NCVs for each chromosome using all chromosomes as described in the previous Examples.

The data shown in Table 9, provides four normalizing chromosomes for each of all 1-22, X and Y chromosomes that were determined to have the lowest CVs for the respective doses in the 3 sample sets provided.

Normalizing chromosomes having the lowest four % CVs are provided. The second lowest variability for chromosome 13 was determined to result from the average of the sum of chromosome doses for chromosomes 2-6. The variability of the chromosome dose for chromosome Y is smallest when the average of the sum of chromosome doses for chromosomes 2-6 is used.

TABLE 9

Normalizing Chromosomes for all Chromosomes

| Chromosome | Normalizing chromosomes - Training set 1 n = 65 | Normalizing chromosomes - Test set 1 n = 48 | Normalizing chromosomes - Training set 2 n = 48 |
|---|---|---|---|
| 1 | 11, 10, 9, 15 | 11, 10, 15, 9 | 10, 11, 9, 15 |
| 2 | 8, 12, 18, 7 | 8, 12, 7, 14 | 7, 8, 12, 14 |
| 3 | 6, 5, 18, 8 | 6, 5, 8, 18 | 6, 5, 8, 18 |
| 4 | 13, 5, 3, 6 | 13, 5, 6, 3, | 13, 5, 6, 3 |
| 5 | 3, 6, 18, 8 | 3, 6, 8, 18 | 6, 3, 8, 18 |
| 6 | 3, 5, 18, 8 | 3, 5, 8, 18 | 5, 3, 8, 18 |
| 7 | 12, 14, 2, 8 | 12, 14, 2, 8 | 12, 2, 8, 14 |
| 8 | 2, 3, 5, 6, | 2, 3, 12, 7 | 2, 7, 12, 3 |
| 9 | 1, 10, 11, 7 | 11, 10, 1, 14 | 11, 1, 10, 14 |
| 10 | 11, 9, 1, 14 | 11, 1, 9, 15 | 1, 11, 9, 15 |
| 11 | 9, 10, 1, 21 | 9, 10, 1, 15 | 1, 10, 9, 15 |
| 12 | 14, 7, 2, 9, | 7, 14, 2, 8 | 7, 14, 2, 8 |
| 13 | 4, 2-6, 5, 6 | 4, 2-6, 5, 6 | 4, 5, 2-6, 3 |
| 14 | 12, 7, 9, 21 | 12, 7, 9, 2 | 12, 7, 2, 9 |
| 15 | 1, 11, 10, 9 | 1, 10, 11, 9, | 1, 10, 11, 9, |
| 16 | 20, 17, 15, 1 | 20, 17, 15, 1 | 20, 17, 15, 10 |
| 17 | 16, 20, 22, 19 | 12, 20, 19, 22 | 16, 20, 19, 22 |
| 18 | 8, 3, 6, 2, | 8, 5, 6, 8 | 8, 3, 2, 6 |
| 19 | 22, 17, 16, 20 | 22, 17, 16, 20 | 22, 17, 16, 20 |
| 20 | 16, 17, 15, 1 | 16, 17, 15, 1 | 16, 17, 15, 10 |
| 21 | 9, 11, 10, 1 | 14, 9, 12, 7 | 14, 9, 11, 7 |
| 22 | 19, 17, 16, 20 | 19, 17, 16, 20 | 19, 17, 16, 20 |
| X | 4, 13, 5, 3 | 4, 13, 5, 3 | 5, 13, 3, 6 |
| Y | 2-6, 4, 7, 5 | 2-6, 13, 5, 4 | 2-6, 5, 4, 3 |

Based on the results, normalizing chromosomes can be selected whether the second normalizing chromosome is one of two selected normalizing chromosomes for a chromosome of interest, or the second normalizing chromosome is a normalizing chromosome for the first normalizing chromosome, which is the first normalizing chromosome for a chromosome of interest.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining the presence or absence of a fetal chromosomal aneuploidy in a maternal test sample obtained from a pregnant human, said sample comprising a mixture of fetal and maternal nucleic acid molecules, said method comprising:
   (a) preparing a sequencing library from said mixture of fetal and maternal nucleic acids in said maternal sample;
   (b) massively parallel sequencing said fetal and maternal nucleic acids in said sequencing library to obtain sequence information for said fetal and maternal nucleic acids in said sample;
   (c) receiving said sequence information in a computer-readable medium;
   (d) using computer-readable instructions:
      (i) identifying from said sequence information a number of sequence tags for a chromosome of interest and a number of sequence tags for at least two normalizing chromosomes;
      (ii) using said numbers of sequence tags to calculate a first normalizing value and a second normalizing value for said chromosome of interest; and
      (iii) comparing said first normalizing value for said chromosome of interest to a first threshold value and comparing said second normalizing value for said chromosome of interest to a second threshold value to determine the presence or absence of a fetal aneuploidy in said sample.

2. The method of claim 1, wherein said first normalizing value for said chromosome of interest is a first chromosome dose, said first chromosome dose being a ratio of the number of sequence tags for said chromosome of interest and a first normalizing chromosome, and wherein said second normalizing value for said chromosome of interest is a second chromosome dose, said second chromosome dose being a ratio of the number of sequence tags for said chromosome of interest and a second normalizing chromosome.

3. A method for determining the presence or absence of a fetal chromosomal aneuploidy in a maternal test sample obtained from a pregnant human, said sample comprising a mixture of fetal and maternal nucleic acid molecules, said method comprising:
   (a) preparing a sequencing library from said mixture of fetal and maternal nucleic acids in said maternal sample;
   (b) massively parallel sequencing said fetal and maternal nucleic acids in said sequencing library to obtain sequence information for said fetal and maternal nucleic acids in said sample;
   (c) receiving said sequence information in a computer-readable medium;
   (d) using computer-readable instructions:
      (i) identifying from said sequence information a number of sequence tags for a chromosome of interest and a number of sequence tags for at least two normalizing chromosomes;
      (ii) using said number of sequence tags for said chromosome of interest and the number of sequence tags for a first normalizing chromosome for said chromosome of interest to determine a first normalizing value for said chromosome of interest, and using said number of sequence tags for said first normalizing chromosome and the number of sequence tags for a second normalizing chromosome to determine a second normalizing value for said first normalizing chromosome; and
      (iii) comparing said first normalizing value for said chromosome of interest to a first threshold value and comparing said second normalizing value for said first normalizing chromosome to a second threshold value to determine the presence or absence of a fetal aneuploidy in said sample.

4. The method of claim 3, wherein said first normalizing value for said chromosome of interest is a first chromosome dose, said first chromosome dose being a ratio of the number of sequence tags for said chromosome of interest and a first normalizing chromosome, and wherein said second normalizing value for said chromosome of interest is a second chromosome dose, said second chromosome dose being a ratio of the number of sequence tags for said first normalizing chromosome and a second normalizing chromosome.

5. The method of any one of claim 1 or claim 3, further comprising determining a first and a second normalized chromosome value (NCV), wherein said first NCV relates said first chromosome dose to the mean of the corresponding first chromosome dose in a set of qualified samples, and wherein said second NCV relates said second chromosome dose to the mean of the corresponding second chromosome dose in a set of qualified samples as:

$$NCV_{ij} = \frac{x_{ij} - \hat{\mu}_j}{\hat{\sigma}_j}$$

where $\hat{\mu}_j$ AND $\hat{\sigma}_j$ are the estimated mean and standard deviation, respectively, for the j-th chromosome dose in a set of qualified samples, and $x_{ij}$ is the observed j-th chromosome dose for test sample i.

6. The method of any one of claim 1 or claim 3, wherein said normalizing chromosomes are used to normalize chromosome 21, and said normalizing chromosomes are selected from chromosomes 9, 11, 14, and 1.

7. The method of any one of claim 1 or claim 3, wherein said normalizing chromosomes are used to normalize chromosome 18, and said normalizing chromosomes are selected from chromosomes 8, 3, 2, and 6.

8. The method of any one of claim 1 or claim 3, wherein said normalizing chromosomes are used to normalize chromosome 13, and said normalizing chromosomes are selected from chromosome 4, the group of chromosomes 2-6, chromosome 5, and chromosome 6.

9. The method of any one of claim 1 or claim 3, wherein said normalizing chromosomes are used to normalize chromosome X, and said normalizing chromosomes are selected from chromosomes 6, 5, 13, and 3.

10. The method of any one of claim 1 or claim 3, wherein said normalizing chromosomes are used to normalize chromosome 1, and said normalizing chromosomes are selected from chromosomes 10, 11, 9 and 15.

11. The method of any one of claim 1 or claim 3, wherein said normalizing chromosomes are used to normalize chromosome 2, and said normalizing chromosomes are selected from chromosomes 8, 7, 12, and 14.

12. The method of any one of claim 1 or claim 3, wherein said normalizing chromosomes are used to normalize chromosome 3, and said normalizing chromosomes are selected from chromosomes 6, 5, 8, and 18.

13. The method of any one of claim 1 or claim 3, wherein said normalizing chromosomes are used to normalize chromosome 4, and said normalizing chromosomes are selected from chromosomes 3, 5, 6, and 13.

14. The method of any one of claim 1 or claim 3, wherein said normalizing chromosomes are used to normalize chromosome 5, and said normalizing chromosomes are selected from chromosomes 6, 3, 8, and 18.

15. The method of any one of claim 1 or claim 3, wherein said normalizing chromosomes are used to normalize chromosome 6, and said normalizing chromosomes are selected from chromosomes 5, 3, 8, and 18.

16. The method of any one of claim 1 or claim 3, wherein said normalizing chromosomes are used to normalize chromosome 7, and said normalizing chromosomes are selected from chromosomes 12, 2, 14 and 8.

17. The method of any one of claim 1 or claim 3, wherein: said normalizing chromosomes are used to normalize chromosome 8, and said normalizing chromosomes are selected from chromosomes 2, 7, 12, and 3.

18. The method of any one of claim 1 or claim 3, wherein said normalizing chromosomes are used to normalize chromosome 9, and said normalizing chromosomes for chromosome 9 are selected from chromosomes 11, 10, 1, and 14.

19. The method of any one of claim 1 or claim 3, wherein said normalizing chromosomes are used to normalize chromosome 10, and said normalizing chromosomes are selected from chromosomes 1, 11, 9, and 15.

20. The method of any one of claim 1 or claim 3, wherein said normalizing chromosomes are used to normalize chromosome 11, and said normalizing chromosomes are selected from chromosomes 1, 10, 9, and 15.

21. The method of any one of claim 1 or claim 3, wherein said normalizing chromosomes are used to normalize chromosome 12, and said normalizing chromosomes are selected from chromosomes 7, 14, 2, and 8.

22. The method of any one of claim 1 or claim 3, wherein said normalizing chromosomes are used to normalize chromosome 14, and said normalizing chromosomes are selected from chromosomes 12, 7, 2, and 9.

23. The method of any one of claim 1 or claim 3, wherein said normalizing chromosomes are used to normalize chromosome 15, and said normalizing chromosomes are selected from chromosomes 1, 10, 11, and 9.

24. The method of any one of claim 1 or claim 3, wherein said normalizing chromosomes are used to normalize chromosome 16, and said normalizing chromosomes are selected from chromosomes 20, 17, 15, and 1.

25. The method of any one of claim 1 or claim 3, wherein said normalizing chromosomes are used to normalize chromosome 17, and said normalizing chromosomes are selected from chromosomes 16, 20, 19 and 22.

26. The method of any one of claim 1 or claim 3, wherein said normalizing chromosomes are used to normalize chromosome 19, and said normalizing chromosomes are selected from 22, 17, 16, and 20.

27. The method of any one of claim 1 or claim 3, wherein said normalizing chromosomes are used to normalize chromosome 20, and said normalizing chromosomes are selected from chromosomes 16, 17, 15, and 1.

28. The method of any one of claim 1 or claim 3, wherein said normalizing chromosomes are used to normalize chromosome 22, and said normalizing chromosomes are selected from chromosomes 19, 17, 16, and 20.

29. The method of any one of claim 1 or claim 3, further comprising repeating the steps of claim 1 or claim 3 for at least two chromosomes of interest to determine the presence or absence of said different fetal chromosomal aneuploidies.

30. The method of claim 29, wherein the method comprises repeating the method of claim 1 or claim 3 for all chromosomes to determine the presence or absence of different fetal chromosomal aneuploidies.

31. The method of claim 1 or claim 3, wherein said fetal chromosomal aneuploidy is selected from T21, T13, T18, and monosomy X.

32. The method of claim 1 or claim 3, wherein obtaining sequence information for the fetal and maternal nucleic acids in the sample comprises sequencing fetal and maternal nucleic acid molecules in the sample.

33. The method of claim 1 or claim 3, wherein:
obtaining said sequence information comprises sequencing-by-synthesis using reversible dye terminators;
obtaining said sequence information comprises sequencing-by-ligation; or
obtaining said sequence information comprises single molecule sequencing.

34. The method of claim 1 or claim 3, wherein said chromosomal aneuploidy is a partial or complete chromosomal aneuploidy.

35. The method of claim 1 or claim 3, wherein said maternal test sample is a plasma sample obtained from a pregnant woman and said nucleic acid molecules are cfDNA molecules.

* * * * *